(12) United States Patent
GuhaThakurta et al.

(10) Patent No.: US 10,261,091 B2
(45) Date of Patent: Apr. 16, 2019

(54) HUMORAL IMMUNE RESPONSE AGAINST TUMOR ANTIGENS AFTER TREATMENT WITH A CANCER ANTIGEN SPECIFIC ACTIVE IMMUNOTHERAPY AND ITS ASSOCIATION WITH IMPROVED CLINICAL OUTCOME

(71) Applicant: Dendreon Corporation, Seattle, WA (US)

(72) Inventors: Debraj GuhaThakurta, Sammamish, WA (US); James Trager, Seattle, WA (US); Nadeem Sheikh, Seattle, WA (US)

(73) Assignee: Dendreon Corporation, Seattle, WA (US)

( * ) Notice: Subject to any disclaimer, the term of this patent is extended or adjusted under 35 U.S.C. 154(b) by 0 days.

(21) Appl. No.: 14/479,084

(22) Filed: Sep. 5, 2014

(65) Prior Publication Data

US 2015/0064210 A1 Mar. 5, 2015

Related U.S. Application Data

(60) Provisional application No. 61/874,279, filed on Sep. 5, 2013, provisional application No. 61/892,373, filed on Oct. 17, 2013.

(51) Int. Cl.
| | | |
|---|---|---|
| *G01N 33/574* | (2006.01) | |
| *G01N 33/68* | (2006.01) | |
| *A61K 39/00* | (2006.01) | |
| *G01N 33/564* | (2006.01) | |
| *G16H 50/50* | (2018.01) | |
| *G16H 50/70* | (2018.01) | |

(52) U.S. Cl.
CPC ...... *G01N 33/6854* (2013.01); *A61K 39/0011* (2013.01); *G01N 33/564* (2013.01); *G01N 33/57434* (2013.01); *A61K 2039/5154* (2013.01); *A61K 2039/575* (2013.01); *G01N 2500/00* (2013.01); *G01N 2800/52* (2013.01); *G16H 50/50* (2018.01); *G16H 50/70* (2018.01); *Y02A 90/26* (2018.01)

(58) Field of Classification Search
None
See application file for complete search history.

(56) References Cited

U.S. PATENT DOCUMENTS

| | | |
|---|---|---|
| 2004/0161413 A1 | 8/2004 | Laus et al. |
| 2010/0136019 A1 | 6/2010 | Vignali et al. |
| 2010/0150946 A1 | 6/2010 | Jooss et al. |
| 2010/0233691 A1 | 9/2010 | Bankaitis-Davis et al. |
| 2011/0177059 A1 | 7/2011 | Chang |
| 2011/0306514 A1 | 12/2011 | Hewitt et al. |
| 2013/0016140 A1 | 1/2013 | Oniki |
| 2013/0116140 A1* | 5/2013 | Watson ............... G01N 33/6893 506/9 |
| 2013/0156813 A1 | 6/2013 | Gildersleeve et al. |
| 2015/0309036 A1* | 10/2015 | Abate-Shen ......... C12Q 1/6886 506/9 |

OTHER PUBLICATIONS

Smith et al, J Biomed Biotech, 2010; 2011:ID 454861.*
Cheever et al, Clin Cancer Res, 2011, 17:3520-3526.*
McNeel, J Clin Oncol, 2009, 27:4047-4054.*
Aragon-Ching et al., "Angiogenesis inhibition in prostate cancer: current uses and future promises", Journal of Oncology, vol. 2010, pp. 361836 (2010).
Arencibia et al., "Gene expression profiling reveals overexpression of TSPAN13 in prostate cancer", *International Journal of Oncology*. vol. 34, No. 2, pp. 457-463 (2009).
Balan et al., "Tyrosine-phosphorylated Galectin-3 Protein Is Resistant to Prostate-specific Antigen (PSA) Cleavage", *J Biol Chem*, vol. 287, pp. 5192-5198 (2012).
Butterfield et al., "Determinant Spreading Associated with Clinical Response in Dendritic Cell-based Immunotherapy for Malignant Melanoma", *Clin Cancer Res*, vol. 9, No. 3, pp. 998-1008 (2003).
Califice et al., "Dual activities of galectin-3 in human prostate cancer: tumor suppression of nuclear galectin-3 vs tumor promotion of cytoplasmic galectin-3", *Oncogene*, vol. 23, No. 45, pp. 7527-7536 (2004).
Carducci et al., "Effect of endothelin-A receptor blockade with atrasentan on tumor progression in men with hormone-refractory prostate cancer: a randomized, phase II, placebo-controlled trial", *Journal of clinical Oncology*, vol. 21, No. 4, pp. 679-689 (2003).
Corbiere et al., "Antigen spreading contributes to MAGE vaccination-induced regression of melanoma metastases", *Cancer research*, vol. 71, No. 4, pp. 1253-1262 (2011).
Dai et al., "Vascular endothelial growth factor contributes to the prostate cancer-induced osteoblast differentiation mediated by bone morphogenetic protein", *Cancer research*, vol. 64, No. 3, pp. 994-999 (2004).
Darson et al., "Human glandular kallikrein 2 expression in prostate adenocarcinoma and lymph node metastases", *Urology*, vol. 53, No. 5, pp. 939-944 (1999).
Dawson et al., "Expression and localization of endothelin-converting enzyme-1 in human prostate cancer", *Exp Biol Med (Maywood)*, vol. 231, No. 6, pp. 1106-1110 (2006).
Disis et al., "Humoral Epitope-Spreading Following Immunization with a HER-2/neu Peptide Based Vaccine in Cancer Patients", *J Clin Immunol.*, vol. 24, No. 5, pp. 571-578 (2004).
Elad-Sfadia et al., "Galectin-3 Augments K-Ras Activation and Triggers a Ras Signal That Attenuates ERK but Not Phosphoinositide 3-Kinase Activity", *J Biol Chem.*, vol. 279, pp. 34922-34930 (2004).
Fukasawa et al., "Aminopeptidase N (APN/CD13) is selectively expressed in vascular endothelial cells and plays multiple roles in angiogenesis", *Cancer letters.*, vol. 243, No. 1, pp. 135-143 (2006).

(Continued)

*Primary Examiner* — Mark Halvorson
(74) *Attorney, Agent, or Firm* — Kilpatrick Townsend & Stockton LLP

(57) ABSTRACT

Compositions and methods are provided herein for predicting therapeutic outcome by measuring patient response to cellular antigen specific active immunotherapy (CASAI) using predetermined biomarkers.

11 Claims, 9 Drawing Sheets

(56) References Cited

OTHER PUBLICATIONS

Guzman-Rojas et al., "Cooperative effects of aminopeptidase N (CD13) expressed by nonmalignant and cancer cells within the tumor microenvironment", *Proc Natl Acad Sci U S A.*, vol. 109, No. 5, pp. 1637-1642.
Hardwick et al., "Epitope spreading contributes to effective immunotherapy in metastatic melanoma patients", *Immunotherapy*, vol. 3, No. 6, pp. 731-733.
Herrmann et al., "The endothelin axis in urologic tumors: mechanisms of tumor biology and therapeutic implications", *Expert review of anticancer therapy*, vol. 6, No. 1, pp. 73-81 (2006).
Kantoff et al., "Sipuleucel-T immunotherapy for castration-resistant prostate cancer", *N Engl J Med.*, vol. 363, No. 5, pp. 411-422 (2010).
Kopetz et al., "Endothelin-1 as a target for therapeutic intervention in prostate cancer, *Investigational New Drugs*", vol. 20, No. 2, pp. 173-182 (2002).
Kubota et al., "Role of ES Cell-Expressed Ras (ERas) in Tumorigenicity of Gastric Cancer", *Am J Pathol*, vol. 177, pp. 955-963 (2010).
Kwek et al., "Diversity of antigen-specific responses induced in vivo with CTLA-4 blockade in prostate cancer patients", *J Immunol.*, vol. 189, No. 7, pp. 3759-3766 (2012).
Laderach et al., "A Unique Galectin Signature in Human Prostate Cancer Progression Suggests Galectin-1 as a Key Target for Treatment of Advanced Disease", *Cancer research*, vol. 73, No. 1, pp. 86-96 (2013).
Lambert et al., "Isoforms of endothelin-converting enzyme-1 (ECE-1) have opposing effects on prostate cancer cell invasion", *Br J Cancer*, vol. 99, No. 7, pp. 1114-1120 (2008).
Larkin et al., "Identification of markers of prostate cancer progression using candidate gene expression", *Br J Cancer*, vol. 106, No. 1, pp. 157-165 (2012).
Larsen et al, "T cell responses affected by aminopeptidase N (CD13)-mediated trimming of major histocompatibility complex class II-bound peptides", *J Exp Med*, vol. 184, pp. 183-189 (1996).
Liu et al., "Sex-determining region Y box 4 is a transforming oncogene in human prostate cancer cells", *Cancer research*, vol. 66, No. 8, pp. 4011-4019.
Maecker et al., "The tetraspanin superfamily: molecular facilitators", *FASEB J*, vol. 11, pp. 428-442,(1997).
Magklara et al., "Decreased concentrations of prostate-specific antigen and human glandular kallikrein 2 in malignant versus nonmalignant prostatic tissue", *Urology*, vol. 56, No. 3, pp. 527-532 (2000).
Markowska et al., "Galectin-3 is an important mediator of VEGF- and bFGF-mediated angiogenic response", *The Journal of experimental medicine*, vol. 207, No. 9, pp. 1981-1993 (2010).
Merseburger et al., "Involvement of decreased Galectin-3 expression in the pathogenesis and progression of prostate cancer", *The Prostate*, vol. 68, No. 1, pp. 72-77 (2008).
Mittendorf et al., "Vaccination with a HER2/neu peptide induces intra- and inter-antigenic epitope spreading in patients with early stage breast cancer", *Surgery*, vol. 139, No. 3, pp. 407-418 (2006).
Nam et al., Variants of the hK2 protein gene (KLK2) are associated with serum hK2 levels and predict the presence of prostate cancer at biopsy, *Clin Cancer Res.*, vol. 12, No. 21, pp. 6452-6458 (2006).
Nam et al., "Single nucleotide polymorphism of the human kallikrein-2 gene highly correlates with serum human kallikrein-2 levels and in combination enhances prostate cancer detection", *Journal of clinical oncology*, vol. 21, No. 12, pp. 2312-2319 (2003).
Nelson et al., "Identification of endothelin-1 in the pathophysiology of metastatic adenocarcinoma of the prostate", *Nature medicine*, vol. 1, No. 9, pp. 944-949 (1995).
Nelson et al., "Endothelin-1 inhibits apoptosis in prostate cancer", *Neoplasia*, vol. 7, No. 7, pp. 631-637 (2005).
Nesslinger et al., "Standard treatments induce antigen-specific immune responses in prostate cancer", *Clin Cancer Res*, vol. 13, No. 5, pp. 1493-1502.
Nesslinger et al., "A viral vaccine encoding prostate-specific antigen induces antigen spreading to a common set of self-proteins in prostate cancer patients", *Clin Cancer Res*, vol. 16, No. 15, pp. 4046-4056 (2010).
Newlaczyl et al., "Galectin-3—a jack-of-all-trades in cancer", *Cancer Lett.*, vol. 313, pp. 123-128 (2011).
Nguyen et al., "Antibody responses to galectin-8, TARP and TRAP1 in prostate cancer patients treated with a GM-CSF-secreting cellular immunotherapy", *Cancer immunology, immunotherapy*, vol. 59, No. 9, pp. 1313-1323 (2010).
Pasqualini et al., "Aminopeptidase N is a receptor for tumor-homing peptides and a target for inhibiting angiogenesis", *Cancer research*, vol. 60, No. 3, pp. 722-727 (2000).
Perillo et al., "Galectins: versatile modulators of cell adhesion, cell proliferation, and cell death", *J Mol Med (Berl)*, vol. 76, pp. 402-412 (1998).
Powers et al., "Molecular characterization of the gene encoding the gamma subunit of the human skeletal muscle 1,4-dihydropyridine-sensitive Ca2+ channel (CACNLG), cDNA sequence, gene structure, and chromosomal location", *J Biol Chem*, vol. 268, pp. 9275-9279 (1993).
Raaijmakers et al., "hK2 and free PSA, a prognostic combination in predicting minimal prostate cancer in screen-detected men within the PSA range 4-10 ng/ml", *European urology*, vol. 52, No. 5, pp. 1358-1364 (2007).
Ribas et al., "Determinant spreading and tumor responses after peptide-based cancer immunotherapy", *Trends Immunol*, vol. 24, No. 2, pp. 58-61 (2003).
Rittenhouse et al., "Human Kallikrein 2 (hK2) and prostate-specific antigen (PSA): two closely related, but distinct, kallikreins in the prostate", *Critical reviews in clinical laboratory sciences*, vol. 35, No. 4, pp. 275-368 (1998).
Sano et al., "Human galectin-3 is a novel chemoattractant for monocytes and macrophages", *J Immunol*, vol. 165, pp. 2156-2164 (2000).
Santegoets et al., "The Induction of Autoantibodies to PSMA, PNPO and NRP2 Correlates with Clinical Outcome in Patients Treated with Prostate GVAX/Anti-CTLA-4 Immunotherapy", Keystone Symposium: Cancer Control by Tumor Suppressors and Immune Effectors (J8); *Workshop 3: Perspectives on Breaking Tolerance in Cancer Immunotherapy* (2011).
Scanlan et al., "The cancer/testis genes: review, standardization, and commentary", *Cancer immunity*, vol. 4, No. 1 (2004).
Shalom-Feuerstein et al., "Galectin-3 regulates a molecular switch from N-Ras to K-Ras usage in human breast carcinoma cells", *Cancer Res*, vol. 6565, pp. 7292-7300 ( 2005).
Sheikh et al., "Sipuleucel-T immune parameters correlate with survival: an analysis of the randomized phase 3 clinical trials in men with castration-resistant prostate cancer", *Cancer Immunol Immunother*, vol. 62, pp. 137-147 (2013).
Sorensen et al., "Prognostic significance of aberrantly silenced ANPEP expression in prostate cancer", *Br J Cancer*, vol. 108, pp. 420-428 (2013).
Su et al., "Surface-epitope masking and expression cloning identifies the human prostate carcinoma tumor antigen gene PCTA-1 a member of the galectin gene family", *Proc Natl Acad Sci U S A.*, 93(14): 7252-7257 (1996).
Takahashi et al., Role of ERas in promoting tumour-like properties in mouse embryonic stem cells, *Nature*, vol. 423, pp. 541-545 (2003).
Harding et al., "Identification of antibody responses induced in patients with biochemically recurrent and castration-resistant prostate cancer (CRPC) receiving GVAX immunotherapy for prostate cancer", *ASCO Meeting*, #18: *2008 Meeting on Molecular Markers* (2008).
Taylor et al., "Integrative genomic profiling of human prostate cancer", *Cancer cell*, vol. 18, No. 1, pp. 11-22 (2010).
Thakkar et al., "Endothelin receptor antagonists: rationale, clinical development, and role in prostate cancer therapeutics", *Current oncology reports*, vol. 8, No. 2, pp. 108-113 (2006).
Tomlins et al., "Integrative molecular concept modeling of prostate cancer progression", *Nat Genet*, vol. 39, No. 1, pp. 41-51 (2007).

(56) References Cited

OTHER PUBLICATIONS

Van Den Brule et al., Alteration of the cytoplasmic/nuclear expression pattern of galectin-3 correlates with prostate carcinoma progression, *International journal of cancer Journal international du cancer*, vol. 89, No. 4, ppp. 361-7 (2000).
Vanderlugt et al., "Epitope spreading in immune-mediated diseases: implications for immunotherapy", *Nat Rev Immunol.*, vol. 2, No. 2, pp. 85-95.
Wallace et al., "Tumor immunobiological differences in prostate cancer between African-American and European-American men", *Cancer research*, vol. 68, No. 3, pp. 927-936 (2008).
Wang et al., "Regulation of prostate cancer progression by galectin-3", *The American journal of pathology*, vol. 174, No. 4, pp. 1515-1523 (2009).
Whyteside et al., "ECE-1 influences prostate cancer cell invasion via ET-1-mediated FAK phosphorylation and ET-1-independent mechanisms", *Canadian journal of physiology and pharmacology*, vol. 88, No. 8, pp. 850-854 (2010).
Williams et al., "Prostate-specific antigen (PSA) is activated by KLK2 in prostate cancer ex vivo models and in prostate-targeted PSA/KLK2 double transgenic mice", *The Prostate*, vol. 70, No. 7, pp. 788-796 (2010).

Yang et al., "Aminopeptidase N/CD13 induces angiogenesis through interaction with a pro-angiogenic protein, galectin-3", *Biochemical and Biophysical Research Communications*, vol. 363, No. 2, pp. 336-341 (2007).
Zhang et al., "The F box protein Fbx6 regulates Chk1 stability and cellular sensitivity to replication stress", *Molecular cell*, vol. 35, No. 4, pp. 442-453.
International Search Report and Written Opinion dated Feb. 19, 2015 issued for International Patent Application No. PCT/US14/54413, 15 pages.
Chinese Office Action issued in connection with corresponding Chinese Application No. 201480057668.8, dated Feb. 14, 2017, 5 pages.
Disis et al., "Cellular immune parameters associated with improved long-term survival in advanced stage breast cancer patients after active immunization with a HER2-specific vaccine", Journal of Clinical Oncology, 2008 ASCO Meeting, vol. 26, No. 15S, May 20, 2008:3015.
EP14842529.1, "Extended European Search Report", dated Feb. 21, 2017, 6 pages.
PCT/US2014/054413, "International Preliminary Report on Patentability", dated Mar. 17, 2016, 10 pages.
PCT/US2014/054413, "Invitation to Pay Add'l Fees and Partial Search Report", dated Dec. 12, 2014, 2 pages.

\* cited by examiner

HUMORAL IMMUNE RESPONSE AGAINST TUMOR ANTIGENS AFTER TREATMENT WITH A CANCER ANTIGEN SPECIFIC ACTIVE IMMUNOTHERAPY AND ITS ASSOCIATION WITH IMPROVED CLINICAL OUTCOME

CROSS-REFERENCES TO RELATED APPLICATIONS

This application claims the benefit of priority to U.S. Provisional Application No. 61/874,279, filed on Sep. 5, 2013, and 61/892,373, filed on Oct. 17, 2013, each of which is hereby incorporated by reference in its entirety for all purposes.

BACKGROUND OF THE INVENTION

The immune system is comprised of many different cell types, biomolecules and organs. These include lymphocytes, monocytes and polymorphonuclear leukocytes, numerous soluble chemical mediators (cytokines and growth factors), the thymus, postnatal bone marrow, lymph nodes, liver and spleen. All of these components work together through a complex communication system to fight against microbial invaders such as bacteria, viruses, fungi and parasites, and tumor cells. Together, these components recognize specific molecular antigens as foreign or otherwise threatening, and initiate an immune response against cells or viruses that contain the foreign antigen. The immune system also functions to eliminate damaged or cancerous cells through active surveillance using the same mechanisms used to recognize microbial or viral invaders. The immune system recognizes the damaged or cancerous cells via antigens that are not strictly foreign, but are aberrantly expressed or mutated in the targeted cells.

The human prostatic acid phosphatase (PAP) is predominantly expressed in the prostate gland. Elevated serum levels of PAP are often observed in patients with prostate cancer or other prostate conditions, with the highest serum levels of PAP found in patients with metastasized prostate cancer. (Kirchenbaum *Annals. of the New York Academy of Sciences* 1237 (2011) 64-70). PAP expression is also observed at very low levels in a limited set of normal, non-prostate tissues (including pancreatic islet cells and pilosebaceous units of the skin), as well as in other tumor settings (including breast and colon). The level of PAP expression in these tissues can be at least 1-2 orders of magnitude lower than that detected in the prostate of patients with prostate cancer or another prostate condition. (Graddis et al., Prostatic acid phosphatase expression in human tissues. *Int J Clin Exp Pathol.* 2011 March 31; 4(3): 295-306).

Over 95% of prostate cancer cells express PAP. Therefore several immunotherapeutic strategies for prostate cancer have been devised using PAP as a target. For instance, *Cancer Biology and Therapy* (March 2005, vol. 4, issue 3) reports promising results from a clinical study in which a patient's own immune cells were collected, stimulated to become immunoreactive to PAP, and then returned to the patient by intravenous injection. These new immunological approaches rely on methods that can effectively induce a PAP-specific immunity, including T cell-mediated immunity.

One consequence of an effective immunotherapy may be antigen spread which can result from tumor cell death during the initial response to an immunotherapy which can lead to the release of tumor-associated antigens and the priming of self-reactive T and/or B lymphocytes specific to these antigens. Antigen spread can subsequently promote more efficient tumor killing and can occur with a higher frequency in clinical responders, therefore providing avenues for the identification of novel, mechanism-based, biomarkers of clinical outcome. See, e.g., Ribas, A. et al., Determinant spreading and tumor responses after peptide-based cancer immunotherapy. Trends Immunol, 24, 58-61 (2003).

BRIEF SUMMARY OF THE INVENTION

In some embodiments, the present invention provides, systems, methods, or compositions for measuring antigen spread to: predict therapeutic outcomes of patients undergoing cancer immunotherapy; or identify promising targets for cancer immunotherapy.

In one aspect, the invention provides a method of determining a cancer patient's therapeutic response to cancer immunotherapy, the method comprising the steps of: i. obtaining a baseline antibody level reactive to one or more non-target predetermined biomarker antigens; ii. treating the cancer patient with immunotherapy (e.g., IL2, a CTLA-4 inhibitor, or a IDO inhibitor); iii. obtaining a post-treatment antibody level reactive to the one or more predetermined biomarker antigens from a patient blood sample after treating with immunotherapy; and iv. measuring differences between the baseline and post-treatment antibody levels reactive to the one or more predetermined biomarker antigens, where an increase in the antibody level reactive to the one or more predetermined biomarker antigens over their baseline level predicts a positive therapeutic response. In some cases, the cancer is prostate cancer. In some cases, the predetermined biomarker antigens include one or more (e.g., two or more) antigens selected from the group consisting of ERAS, KRAS, KLK2, PSA, LGALS3, LGALS8, PSA, PSMA, and prostatic acid phosphatase (PAP). In some cases, the predetermined biomarker antigens are one or more (e.g., two or more) antigens selected from the group consisting of ERAS, KRAS, KLK2, PSA, LGALS3, and LGALS8.

In one aspect, the invention provides a method of determining a cancer patient's therapeutic response to cancer antigen specific active immunotherapy (CASAI) treatment with a target cancer antigen, the method comprising the steps of: i. obtaining a baseline antibody level reactive to one or more non-target predetermined biomarker antigens; ii. treating the cancer patient with CASAI using the target cancer antigen; iii. obtaining a post-treatment antibody level reactive to the one or more non-target predetermined biomarker antigens from a patient blood sample after treating with CASAI; and iv. measuring differences between the baseline and post-treatment antibody levels reactive to the one or more non-target predetermined biomarker antigens, where an increase in the antibody level reactive to the one or more non-target predetermined biomarker antigens over their baseline level predicts a positive therapeutic response.

In some embodiments, the method further comprises: i. obtaining baseline and post-treatment levels of antibodies reactive to the target cancer antigen and one or more non-target predetermined biomarker antigens; and ii. measuring the differences between the baseline and post-treatment levels reactive to the target cancer antigen, wherein an increase in the post-treatment antibody level reactive to the target cancer antigen and the increase in the post-treatment antibody level reactive to the one or more non-target predetermined biomarker antigens over their baseline level predicts a positive therapeutic response.

In some cases, the post-treatment increase in the antibody level reactive to the one or more non-target predetermined biomarker antigens is more predictive of a positive therapeutic response than the post-treatment increase in the antibody level reactive to the target cancer antigen. In some cases, the combination of the post-treatment increase in the antibody level reactive to the one or more non-target predetermined biomarker antigens and the post-treatment increase in the antibody level reactive to the target cancer antigen is more predictive of a positive therapeutic response than the post-treatment increase in the antibody level reactive to the target cancer antigen alone. In some cases, the combination of the post-treatment increase in the antibody level reactive to the one or more non-target predetermined biomarker antigens and the post-treatment increase in the antibody level reactive to the target cancer antigen is more predictive of a positive therapeutic response than the post-treatment increase in the antibody levels reactive to the target cancer antigen and one or more other biomarker antigens that are not ERAS, KRAS, KLK2, PSA, LGALS3, or LGALS8.

In one aspect, the invention provides a method of determining a cancer patient's therapeutic response to cancer antigen specific active immunotherapy (CASAI) treatment with a target cancer antigen, the method comprising the steps of: i. obtaining a baseline antibody level reactive to one or more predetermined biomarker antigens, wherein the one or more predetermined biomarker antigens are selected from the group consisting of: a. a biomarker antigen comprising the target cancer antigen and one or more other biomarker antigens; and b. one or more biomarker antigens that do not comprise the target cancer antigen; ii. treating the cancer patient with CASAI using the target cancer antigen; iii. obtaining a post-treatment antibody level reactive to the one or more predetermined biomarker antigens from a patient blood sample after treating with CASAI; and, iv. measuring differences between the baseline and post-treatment antibody levels reactive to the one or more predetermined biomarker antigens, where an increase in the antibody level reactive to the one or more predetermined biomarker antigens over their baseline level predicts a positive therapeutic response.

In some cases, a baseline and a post-treatment reactive antibody level to at least two predetermined biomarker antigens (e.g., non-target predetermined biomarker antigens) are determined.

In some cases, the baseline reactive antibody levels or the post-treatment reactive antibody levels from the patient are reactive IgG levels.

In some cases, the CASAI treatment includes the step of activating patient blood cells under ex vivo conditions.

In some cases, the CASAI treatment uses a target cancer antigen selected from the group consisting of prostatic acid phosphatase (PAP) and a PAP fusion protein.

In some cases, the CASAI treatment uses a PAP-GM-CSF as a target cancer antigen.

In some cases, the patient suffers from a cancer selected from the group consisting of prostate cancer, melanoma, glioma, bladder cancer, urothelial cancer, kidney cancer, lung cancer, breast cancer, liver cancer, pancreatic cancer and colorectal cancer. In some cases, the patient suffers from prostate cancer.

In some cases, the reactive antibody levels are measured using a solid support surface and a fluorescent or enzymatic label.

In some cases, CASAI uses an immunomodulator. For example, the CASAI can use an immunomodulator selected from the group consisting of GM-CSF, an agonists of toll-like receptor (TLR)-2, 3, 4, 5, 7, 8 or 9; a checkpoint inhibitor; a cytokine; and an inhibitor of interleukin (IL)-12, IL-12p70, IL-10, IL-35, transforming growth factor (TGF)β, or indolamine-pyrrole-2,3-dioxygenase. The cytokine can be selected from the group consisting of IL-1, IL-2, IL-4, IL-7, IL-12, IL-15, and IL-21. The inhibitor of IL-12, IL-12p70, IL-10, IL-35, TGFβ, or IDO can be an antibody that binds to IL-12, IL-12p70, IL-10, IL-35, TGFβ, or IDO. In some cases, the immunomodulator is fused to the target cancer antigen utilized in the CASAI treatment.

In some cases, the one or more predetermined biomarker antigens are PSA and one or more other biomarker antigens. For example, the one or more predetermined biomarker antigens can be PSA and one or more of KLK2, KRAS, ERAS, LGALS8, and LGALS3.

In some cases, the target cancer antigen is not PSA and the predetermined biomarker antigens (e.g., non-target predetermined biomarker antigens) include PSA. In some cases, the target cancer antigen is not PSA and the predetermined biomarker antigen is PSA. In some cases, the target cancer antigen is not PAP and the predetermined biomarker antigens (e.g., non-target predetermined biomarker antigens) include PAP.

In some cases, the predetermined biomarker antigens (e.g., non-target predetermined biomarker antigens) include ERAS plus any 1, 2, 3, 4 or 5 markers selected from the group consisting of KLK2, KRAS, PSA, LGALS3, and LGALS8. In other cases, the predetermined biomarker antigens (e.g., non-target predetermined biomarker antigens) include KRAS plus any 1, 2, 3, 4 or 5 markers selected from the group consisting of KLK2, ERAS, PSA, LGALS3, and LGALS8. In still other cases, the predetermined biomarker antigens (e.g., non-target predetermined biomarker antigens) include LGALS3 plus 1, 2, 3, 4, or 5 markers selected from the group consisting of KLK2, KRAS, ERAS, PSA, and LGALS8. In yet other cases, the predetermined biomarker antigens (e.g., non-target predetermined biomarker antigens) include KLK2 plus 1, 2, 3, 4, or 5 markers selected from the group consisting of KRAS, ERAS, PSA, LGALS3, and LGALS8. In yet other embodiments, the predetermined biomarker antigens (e.g., non-target predetermined biomarker antigens) include LGALS8 plus 1, 2, 3, 4, or 5 markers selected from the group consisting of KLK2, KRAS, ERAS, PSA, and LGALS3. In yet other cases, the predetermined biomarker antigens (e.g., non-target predetermined biomarker antigens) include PSA plus 1, 2, 3, 4, or 5 markers selected from the group consisting of KLK2, KRAS, ERAS, LGALS3, and LGALS8.

In some embodiments, the present invention provides a method of determining therapeutic response in prostate cancer patients undergoing sipuleucel-T treatment, the method comprising the steps of: i. obtaining a baseline level of antibody reactive to one or more predetermined biomarker antigens (e.g., non-target predetermined biomarker antigens), said predetermined biomarker antigens, for example, selected from the group consisting of KLK2, KRAS, ERAS, LGALS8, LGALS3, and PSA; ii. administering to the cancer patient T cells activated ex vivo using a protein comprising a PAP amino acid sequence; iii. obtaining a post-treatment antibody level reactive to the one or more predetermined biomarker antigens (e.g., non-target predetermined biomarker antigens) from a patient blood sample after treating with the activated T cells; and, iv. measuring differences between the baseline and post-treatment reactive antibody levels to the one or more predetermined biomarker antigens (e.g., non-target predetermined biomarker antigens) where an increase in antibody level for the predetermined biomarker antigens (e.g., non-target predetermined biomarker antigens) over their baseline level predicts a positive therapeutic response.

In some cases, the method further comprises: i. obtaining a baseline and post-treatment antibody level reactive to the target cancer antigen (e.g., an antigen comprising PAP) and one or more non-target predetermined biomarker antigens; and ii. measuring the differences between the baseline and post-treatment antibody levels reactive to the target cancer antigen, wherein an increase in the post-treatment antibody level reactive to the target cancer antigen (e.g., an antigen comprising PAP) and the increase in the post-treatment antibody level reactive to the one or more non-target predetermined biomarker antigens over their baseline level predicts a positive therapeutic response.

In some cases, the post-treatment increase in the antibody level reactive to the one or more non-target predetermined biomarker antigens is more predictive of a positive therapeutic response than the post-treatment increase in the antibody level reactive to the target cancer antigen (e.g., an antigen comprising PAP). In some cases, the combination of the post-treatment increase in the antibody level reactive to the one or more non-target predetermined biomarker antigens and the post-treatment increase in the antibody level reactive to the target cancer antigen (e.g., an antigen comprising PAP) is more predictive of a positive therapeutic response than the post-treatment increase in the antibody level reactive to the target cancer antigen alone (e.g., an antigen comprising PAP), or the post-treatment increase in the antibody levels reactive to the target cancer antigen (e.g., an antigen comprising PAP) and one or more other biomarker antigens that are not ERAS, KRAS, KLK2, PSA, LGALS3, or LGALS8.

In some cases, the protein comprising the PAP amino acid sequence is a PAP-GM-CSF fusion protein.

In some cases, the baseline reactive antibody levels or the post-treatment reactive antibody levels from the patient are reactive IgG levels.

In some cases, the sipuleucel-T treatment is ex vivo.

In some cases, the reactive antibody levels are measured using a solid support surface and a fluorescent or enzymatic label.

In some cases, one of the markers is ERAS. In other cases, one of the markers is KLK2.

In yet other cases, one of the markers is PSA.

In some embodiments, the present invention provides a method of identifying target antigens for cancer treatment with improved patient survival, the method comprising: i. obtaining baseline level of antibody reactive to one or more biomarker antigens; ii. treating a patient suffering from cancer with cancer immunotherapy; iii. obtaining a post-treatment level of antibody reactive to the one or more biomarker antigens from a patient blood sample after treating with the cancer immunotherapy; iv. comparing the baseline and post-treatment reactive antibody levels to determine one or more biomarker antigens in which the reactive antibody level is increased; v. correlating the increase in the one or more biomarker antigen reactive antibody levels to an increase in survival; and vi. identifying the one or more biomarker antigens in which the increase in reactive antibody levels are correlated with survival as target antigens for cancer treatment with improved patient survival.

In some embodiments, the present invention provides a system for determining a cancer patient's therapeutic response to cancer antigen specific active immunotherapy (CASAI) treatment with a target cancer antigen, the system comprising: i. a processor; ii. a memory coupled with the processor via an interconnect; iii. a communications interface coupled with the interconnect and adapted to: a. receive a first set of electronic data signals representing a set of pre-treatment interrelated values, each value indicative of a baseline antibody level reactive to one or more non-target predetermined biomarker antigens before CASAI treatment; b. receive a second set of electronic data signals representing a set of post-treatment interrelated values corresponding to the set of pre-treatment values, each of the second set of values indicating an antibody level reactive to the one or more non-target predetermined biomarker antigens from a patient blood sample after treating with CASAI, and; iv. a comparison engine coupled with the processor and configured to compare the set of pre-treatment values with the set of post-treatment values to determine which of the set of post-treatment values have changed from the set of pre-treatment values; and v. an output module configured to provide output data signals representing which of the set of post-treatment values have changed from the set of pre-treatment values, wherein an increase in the antibody level reactive to the one or more non-target predetermined biomarker antigens over their baseline level predicts a positive therapeutic response.

In some embodiments, the present invention provides a system for determining a cancer patient's therapeutic response to cancer antigen specific active immunotherapy (CASAI) treatment with a target cancer antigen, the system comprising: i. a processor; ii. a memory coupled with the processor via an interconnect; iii. a communications interface coupled with the interconnect and adapted to: a. receive a first set of electronic data signals representing a set of pre-treatment interrelated values, each value indicative of a baseline antibody level reactive to one or more predetermined biomarker antigens before CASAI treatment, wherein the one or more predetermined biomarker antigens are selected from the group consisting of: 1. a biomarker antigen comprising the target cancer antigen and one or more other predetermined biomarker antigens; and 2. one or more biomarker antigens that do not comprise the target cancer antigen; b. receive a second set of electronic data signals representing a set of post-treatment interrelated values corresponding to the set of pre-treatment values, each of the second set of values indicating an antibody level reactive to the one or more predetermined biomarker antigens from a patient blood sample after treating with CASAI, and; iv. a comparison engine coupled with the processor and configured to compare the set of pre-treatment values with the set of post-treatment values to determine which of the set of post-treatment values have changed from the set of pre-treatment values; and v. an output module configured to provide output data signals representing which of the set of post-treatment values have changed from the set of pre-treatment values, wherein an increase in the antibody level reactive to the one or more predetermined biomarker antigens over their baseline level predicts a positive therapeutic response.

In some cases, the processor is further configured to determine a reference set of values to serve as a baseline antibody level for the patient from the set of pre-treatment values indicative of a baseline antibody level reactive to one or more predetermined biomarker antigens (e.g., non-target predetermined biomarker antigens) before CASAI treatment. In some cases, the one or more predetermined biomarker antigens (e.g., non-target predetermined biomarker antigens) are selected from the group consisting of ERAS, KRAS, KLK2, PSA, LGALS3, and LGALS8.

In some cases, the iii. the system communication interface is further adapted to: c. receive values for pre- and post-treatment levels of antibodies reactive to a CASAI target antigen; the iv. system comparison engine is further configured to compare pre- and post-treatment values to determine the presence, absence or the magnitude of increase in antibody levels reactive to the target antigen; and the v system output module is further configured to provide output data signals representing the presence absence or magnitude of increase in antibody level reactive to the target antigen, wherein an increase in the antibody levels reactive to one or more non-target predetermined biomarker antigens in combination with the increase in antibody level reactive to target cancer antigen predicts a positive therapeutic response.

In some cases the target cancer antigen used in CASAI treatment is not PSA and the one or more predetermined biomarker antigens (e.g., non-target predetermined biomarker antigens) include PSA. In some cases the target cancer antigen used in CASAI treatment is PSA and the one or more predetermined biomarker antigens include the target biomarker antigen PSA and one or more other non-target predetermined biomarker antigens.

In some cases, the reactive antibody levels are reactive IgG levels.

In some case, the target cancer antigen is PAP or a PAP fusion protein.

In some embodiments, the present invention provides a method of determining therapeutic response in prostate cancer patients undergoing immunomodulatory treatment, the method comprising the steps of: i. obtaining a baseline level of antibody reactive to one or more non-target predetermined biomarker antigens, said non-target predetermined biomarker antigens selected from the group consisting of ERAS, KRAS, KLK2, PSA, LGALS3, and LGALS8; ii. administering to the prostate cancer patient an immunomodulatory agent and a prostate cancer antigen (e.g., PAP or PSA); iii. obtaining a post-treatment level of antibody reactive to one or more non-target predetermined biomarker antigens from a patient blood sample after treating with the immunomodulatory agent, said non-target predetermined biomarker antigens selected from the group consisting of ERAS, KRAS, KLK2, PSA, LGALS3, and LGALS8; and iv. comparing differences between the baseline and post-treatment reactive antibody levels to the one or more non-target predetermined biomarker antigens, wherein an increase in antibody level for the non-target predetermined biomarker antigens over their baseline level predicts a positive therapeutic response.

In some embodiments, the method further comprises: i. obtaining baseline and post-treatment levels of antibodies reactive to the target cancer antigen and one or more non-target predetermined biomarker antigens; and ii. measuring the differences between the baseline and post-treatment levels reactive to the target cancer antigen, wherein an increase in the post-treatment antibody level reactive to the target cancer antigen and the increase in the post-treatment antibody level reactive to the one or more non-target predetermined biomarker antigens over their baseline level predicts a positive therapeutic response.

In some cases, the post-treatment increase in the antibody level reactive to the one or more non-target predetermined biomarker antigens is more predictive of a positive therapeutic response than the post-treatment increase in the antibody level reactive to the target cancer antigen. In some cases, the combination of the post-treatment increase in the antibody level reactive to the one or more non-target predetermined biomarker antigens and the post-treatment increase in the antibody level reactive to the target cancer antigen is more predictive of a positive therapeutic response than the post-treatment increase in the antibody level reactive to the target cancer antigen alone, or the post-treatment increase in the antibody levels reactive to the target cancer antigen and one or more other biomarker antigens that are not ERAS, KRAS, KLK2, PSA, LGALS3, or LGALS8.

DETAILED DESCRIPTION OF THE INVENTION

I. Introduction

Figure 1:
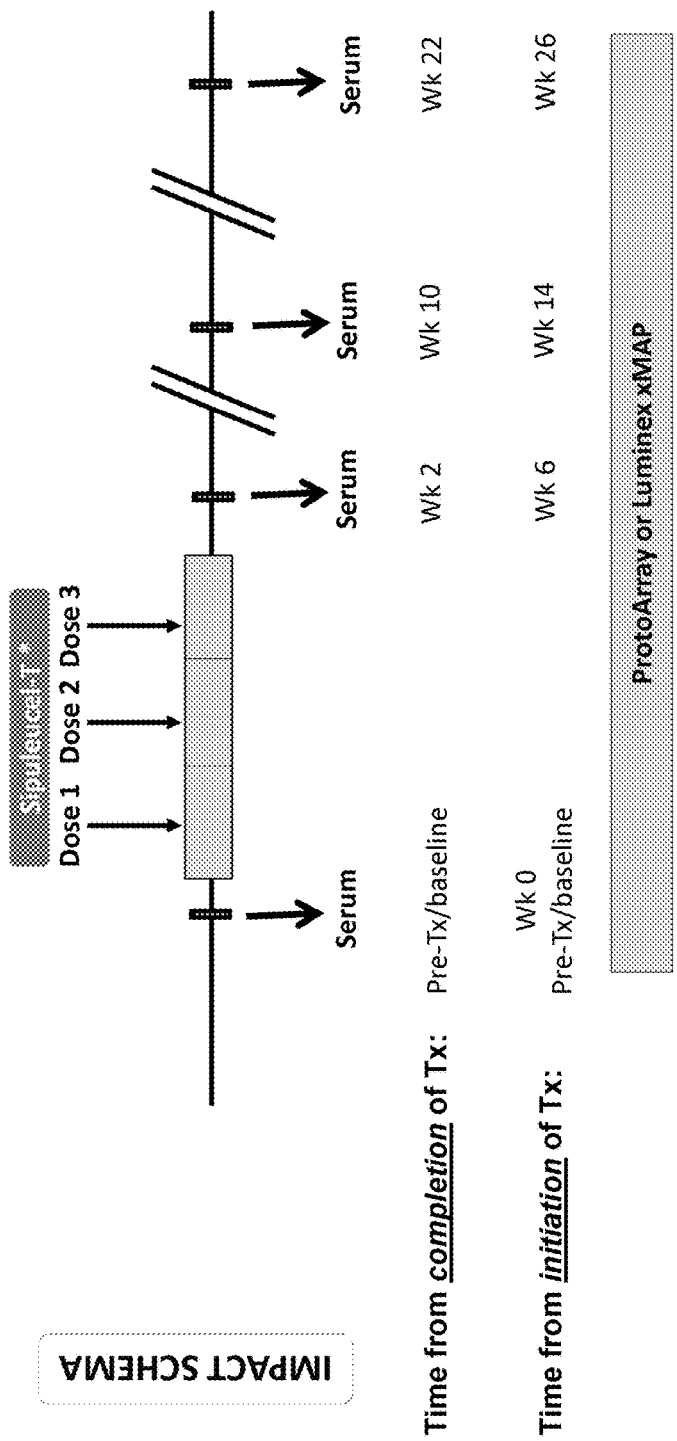
FIG. 1: study design with immune monitoring time points indicated with arrows (Kantoff et al., 2010). The three treatment cycles (or doses) of sipuleucel-T and post treatment follow-up time-points after completion of treatment, week 2, week 10, and week 22/post-progression follow-up, are indicated as Wk 2, Wk-10, Wk-22/PPFU (post-progression follow-up) respectively.

Tumor tissue destruction by cancer immunotherapy may lead to immune responses to non-targeted tumor associated antigens, a phenomenon referred to as antigen spread, determinant spread, or epitope spread (Vanderlugt et al., 2002). Methods and compositions for cancer immunotherapy are described in further detail below.

There are reports from studies with small numbers of patients suggesting the extent of antigen spread may be indicative of survival benefit post-treatment with cancer immunotherapies (Santegoets, 2011; Butterfield, et al., 2003; T. C. Harding M N, et al., 2008; Mittendorf, et al., 2006). Measuring the extent of antigen spread may be important for: (i) understanding the immune response and mechanism of action in vivo, (ii) for identifying early, post-treatment biomarkers of effective clinical response, and (iii) for identifying antigens that may themselves be therapeutic targets for future product development.

It is suggested that tumor cell death or tissue damage during the initial response to a cancer immunotherapy may lead to the release and priming of self-reactive T and/or B lymphocytes specific to antigens that are not directly targeted by the therapy (Vanderlugt et al., 2002). The broadened immune response may subsequently promote more efficient killing of tumor cells (Hardwick, et al., 2011; Corbiere, et al., 2011), including those that may not express the tumor antigen targeted by the immunotherapy (Santegoets, 2011). Early studies in this area have suggested that a broadened antibody response to a cancer immunotherapy may be observed at a higher frequency in clinical responders compared to non-responders (Santegoets, 2011; Butterfield, et al., 2003; T. C. Harding M N, et al., 2008; Mittendorf, et al., 2006). Antigen spread (i.e., antibody responses to antigen/s that are not contained in the immunotherapy) has been observed in response to target-specific cancer vaccines and immunotherapy treatments such as PSA immunotherapy for prostate cancer (Nesslinger, et al., 2010), and Her2/neu vaccination for breast cancer (Disis, et al., 2004), and MAGE-A3 vaccination (Hardwick, et al., 2011; Corbiere, et al., 2011). Antigen spread has also been observed in response to immunotherapy treatment with a non-target-specific immunomodulator. For example, treatment of prostate cancer with the immunomodulator anti-CTLA4 (ipilimumab), which suppresses an immune system checkpoint can result in a broadened immune response (Kwek, et al., 2012).

Accordingly, methods and compositions for measuring the extent of antigen spread in a patient undergoing immunotherapy such as CASAI, treatment with a cancer cell or a mixture of antigens derived therefrom, or treatment with an immunomodulator are provided herein. Methods and compositions for predicting a positive therapeutic response to treatment are also provided. Such methods and compositions can include utilizing measurements of antigen spread. Such methods and compositions can also include measurements of the level of antibodies reactive to one or more predetermined biomarker antigens, such as the biomarker antigens provided herein. Such methods and compositions can further include measurements of the change in the level of antibodies reactive to one or more predetermined biomarker antigens, such as the biomarker antigens provided herein, in response to cancer treatment with an immunomodulator, treatment with a cancer cell or a mixture of antigens derived therefrom, or CASAI. Moreover, methods and compositions for identifying new cancer antigens for development of additional CASAI therapies are provided herein.

II. Definitions

The abbreviations used herein have their conventional meaning within the chemical and biological arts.

As used herein, the term "determining" in the context of determining a therapeutic response refers to predicting, identifying, estimating, quantifying, calculating or otherwise deriving the therapeutic response of a patient to cancer antigen specific immunotherapy (e.g., CASAI). In some cases, determining refers to providing a prognosis, estimate, or prediction regarding the likelihood of a positive therapeutic response (e.g., based on an increase in reactive antibodies to one or more predetermined biomarker antigens). In some cases, the likelihood of a positive therapeutic response is relative. For example, the likelihood can be increased or decreased relative to the general population of patients receiving the same or similar immunotherapy. In some cases, the likelihood is increased or decreased relative to a matched population, e.g., a population of patients with one or more similar risk factors (e.g., Gleason Score, PSA level, LDH, bone lesions, or bisphosphonate usage). In some cases, the likelihood is absolute.

As used herein, the term "antigen" refers to a molecule such as a protein, hapten, carbohydrate, lipid, etc., that evokes an immune response. For example, an antigen can evoke T-cell activation, B-cell activation, or T and B-cell activation. Antigens in general, or a portion thereof, bind the major histocompatibility complex (MHC) and are presented to T-cell receptors by antigen presenting cells. Antigens are recognized by, and can bind to, antibodies.

As used herein, the term "cancer antigen" refers to an antigen that is aberrantly expressed in, mutated in, or specific to, a cancer cell. Exemplary cancer antigens include, but are not limited to prostatic acid phosphatase (PAP), alpha-fetoprotein (AFP), carcinoembryonic antigen (CEA), CA-125, MUC-1, epithelial tumor antigen (ETA), tyrosinase, melanoma associated antigen (MAGE), carbonic anhydrase IX, HER-2/neu, cytotoxic T-lymphocyte antigen 4, prostate specific antigen (PSA), hepatitis B surface antigen, telomerase reverse transcriptase (TERT), survivin, EGFRvIII, melanocyte derived peptide, multiple melanoma-associated peptides, and the cervical carcinoma antigen HPV-16-E7. Cancer antigens can also include the antigens identified herein as eliciting an elevated immune response due to antigen spread subsequent to, or during, cellular immunotherapy (e.g., PSA, KLK2, KRAS, ERAS, LGALS8, or LGALS3). Cancer antigens can include compositions derived from or containing allogenic or autologous tumor cells. In some cases, the cancer antigens are packaged in a virus, a virus like particle, or a lipid membrane. In some cases, cancer antigens are encoded for in one or more recombinant expression cassettes.

As used herein, the term "immunomodulator" refers to compositions or formulations that modulate the immune system. Immunomodulators can include compositions or formulations that activate the immune system (e.g., adjuvants or activators), or downregulate the immune system. Adjuvants can include aluminum-based compositions, as well as compositions that include bacterial or mycobacterial cell wall components. Activators can include molecules that activate antigen presenting cells to stimulate the cellular immune response. Activators can include, but are not limited to, agonists of toll-like receptors TLR-2, 3, 4, 6, 7, 8, or 9; granulocyte macrophage colony stimulating factor (GM-CSF); TNF; CD40L; CD28; FLT-3 ligand; or cytokines such as IL-1, IL-2, IL-4, IL-7, IL-12, IL-15, or IL-21. Activators can also include compounds that inhibit the activity of an immune suppressor, such as an inhibitor of the immune suppressors IL-10, IL-35, TGFβ, IDO, or cyclophosphamide, or inhibit the activity of a an immune checkpoint such as an antibody against CTLA4, PD-1, or PD-L1. Activators can also include costimulatory molecules such as CD40, CD80, or CD86. Immunomodulators can also include agents that downregulate the immune system such as antibodies against IL-12p70, antagonists of toll-like receptors TLR-2, 3, 4, 5, 6, 8, or 9, or general suppressors of immune function such as cyclophosphamide, cyclosporin A or FK506. These agents (e.g., adjuvants, activators, or downregulators) can be combined to shape an optimal immune response.

Immunomodulators can be provided as fusion peptides that are physically linked to one or more cancer antigens. In some cases, the cancer antigen and immunomodulator are present on one or more expression cassettes, e.g. to induce expression of a cancer antigen-immunomodulator fusion protein, for introduction into a patient or cells derived from a patient. In other cases, the immunomodulators are expressed or provided to the patient or contacted with the patients cells ex vivo in temporal and/or spatial proximity to the cancer antigen.

As used herein, the term "cancer immunotherapy" refers to any therapy that is designed to provoke or enhance an immune response against cancer cells in a patient. For example, cancer immunotherapy includes, but is not limited to, cancer antigen specific active immunotherapy, treatment with an immunomodulator (e.g., an activator or an inhibitor of an immune suppressor or an inhibitor of a checkpoint inhibitor), or treatment with a cancer cell or a mixture of antigens derived therefrom (e.g., treatment with antigens derived from a cancer cell line).

As used herein, the term "cancer antigen specific active immunotherapy" (CASAI) refers to the immunization of a patient against one or more target cancer antigens. CASAI can refer to ex vivo treatment in which peripheral blood mononuclear cells, such as T-cells, B-cells, NK cells, and/or antigen presenting cells, are removed from a patient and contacted with one or more target cancer antigens. The cells can then be re-introduced into the patient. CASAI can also refer to in vivo CASAI in which the target cancer antigens are introduced into the patient and the immune response occurs therein. In some cases, CASAI utilizes one or more target cancer antigens fused to, or in the presence of, an immunomodulator such as an adjuvant or an activator. Exemplary CASAI methods include contacting the antigen presenting cells of a patient with one or more target cancer antigens, either in vivo or ex vivo, in the presence of one or more immunomodulators such as GM-CSF, TNF; CD40L; CD28; or FLT-3 ligand; an agonist of toll-like receptors TLR-2, 3, 4, 5, 6, 8, or 9; a checkpoint inhibitor such as an antibody against CTLA4, PD-1, or PD-L1; a cytokine such as IL-1, IL-4, IL-7, IL-12, IL-15 or IL-21; or an inhibitor of IL-10, IL-35, TGFβ, or IDO. Exemplary CASAI methods also include contacting the antigen presenting cells of a patient, either in vivo or ex vivo, with one or more cancer antigens fused to an immunomodulator such as GM-CSF, TNF; CD40L; CTLA4; CD28; FLT-3 ligand; an agonist of toll-like receptors TLR-2, 3, 4, 5, 6, 8, or 9; a checkpoint inhibitor such as an antibody against CTLA4, PD-1, or PD-L1; a cytokine such as IL-1, IL-4, IL-7, IL-12, IL-15 or IL-21; or an inhibitor of an immune suppressor, such as cyclophosphamide, IL-10, IL-35, TGFβ, or IDO. Exemplary CASAI methods also include contacting the antigen presenting cells of a patient, either in vivo or ex vivo, which one or more cancer antigens fused to a costimulatory molecule such as CD40, CD80, or CD86.

As used herein, the term "cell specific active immunotherapy" refers to the immunization of a patient with a syngenic or allogenic cancer cell, or antigens derived therefrom, (e.g., treatment with antigens derived from a cancer cell line such as LnCAP or PC-3 cells) in order to induce an immune response against one or more cancer antigens present in the cancer cell and activate or increase immune surveillance of a patient's own tumor cells.

As used herein, the term "immune checkpoint inhibitors," "checkpoint inhibitors," and the like refers to compounds that inhibit the activity of control mechanisms of the immune system. Immune system checkpoints, or immune checkpoints, are inhibitory pathways in the immune system that generally act to maintain self-tolerance or modulate the duration and amplitude of physiological immune responses to minimize collateral tissue damage. Checkpoint inhibitors can inhibit an immune system checkpoint by inhibiting the activity of a protein in the pathway. Immune system check point proteins include, but are not limited to, cytotoxic T-lymphocyte antigen 4 (CTLA4), programmed cell death 1 protein (PD1), and programmed cell death 1 ligand 1 (PD-L1). As such, checkpoint inhibitors include antagonists of CTLA4, PD1, or PD-L1. For example, antibodies that bind to CTLA4, PD-1, or PD-L1 and antagonize their function are checkpoint inhibitors. Moreover, any molecule (e.g., peptide, nucleic acid, small molecule, etc.) that inhibits the inhibitory function of an immune system checkpoint is a checkpoint inhibitor.

As used herein, the term "biomarkers" refers to an indicator of a biological state of an organism. The level of a biomarker can be measured to determine the biological state of the organism. Exemplary biomarkers include metabolites and macromolecules such as proteins, carbohydrates and lipids. Biomarkers can indicate the presence of a disease, such as cancer, or the severity of a disease or condition. For example, the presence or absence of a biomarker can be indicative of malignancy, metastasis, or lack thereof. In some cases, the level of one or more biomarkers, or a combination thereof, can indicate disease prognosis, therapeutic response, or predict therapeutic outcome. In other cases, the biomarker is an antigen and the level of antibodies (e.g., IgA, IgD, IgE, IgG, IgM, or their subclasses, such as $IgG_1$, $IgG_2$, $IgG_3$, or $IgG_4$) reactive to one or more biomarker antigens, or a combination thereof can indicate disease prognosis, therapeutic response, or predict therapeutic outcome.

As used herein, the term "predetermined biomarker antigens" refers to one or more biomarker antigens, or combinations thereof, that are known indicators of a particular biological state. For example, one or more predetermined biomarker antigens might be detected and/or measured to obtain a disease prognosis or determine a therapeutic response. Alternatively, or additionally, the level of antibodies reactive to one or more predetermined biomarker antigens, or a combination thereof, can indicate a particular biological state. For example, the levels of reactive antibodies (e.g., IgA, IgD, IgE, IgG, IgM, or their subclasses, such as $IgG_1$, $IgG_2$, $IgG_3$, or $IgG_4$) that bind to one or more predetermined biomarker antigens, or a combination thereof, might be detected and/or measured to obtain a disease prognosis or determine a therapeutic response.

Predetermined biomarker antigens include, but are not limited to, PSA, LGALS3, KRAS, ERAS, KLK2, LGALS8/PCTA-1, PAP, or PAP-GM-CSF, individually or in any combination. In some cases, the predetermined biomarker antigens are selected from the group consisting of ERAS, KRAS, KLK2, PSA, LGALS3, LGALS8 and a target cancer antigen. Consequently, in some embodiments, the level of antibodies reactive to one or more of PSA, LGALS3, KRAS, ERAS, KLK2, LGALS8, PAP, or PAP-GM-CSF, individually or in any combination, can be detected and/or measured to obtain a disease prognosis or determine a therapeutic response. In some cases, the levels of antibodies reactive to predetermined biomarker antigens can be determined relative to a pretreatment control.

In some embodiments, the level of antibodies reactive to predetermined biomarker antigens includes antibodies reactive to one or more antigens that are not a target cancer antigen. Similarly, in some embodiments, the level of antibodies reactive to predetermined biomarker antigens do not include antibodies reactive to a target cancer antigen. As such, predetermined biomarker antigens herein include non-target predetermined biomarker antigens.

"Non-target predetermined biomarker antigens" as used herein, refer to predetermined biomarker antigens that, for a particular subject, are not a target cancer antigen used in a CASAI treatment that has been administered to the subject. Thus, since the target cancer antigen can vary, e.g., depending on the CASAI treatment employed, the number and identity of non-target predetermined biomarker antigens can also vary. In some cases, the non-target predetermined biomarker antigens are any combination of one or more antigens selected from the group consisting of ERAS, KRAS, KLK2, PSA, LGALS3, and LGALS8. Consequently, in some embodiments, the level of antibodies reactive to one or more of ERAS, KRAS, KLK2, PSA, LGALS3, and LGALS8, individually or in any combination, can be detected and/or measured to obtain a disease prognosis or determine a therapeutic response. For example, in some cases, CASAI treatment is performed with a target cancer antigen and therapeutic outcome or therapeutic response is determined by measuring the level of antibodies reactive to one or more non-target predetermined biomarker antigens.

In some cases, the level antibodies reactive to one or more non-target predetermined biomarker antigens in combination with the level of antibodies reactive to the target cancer antigen can be detected and/or measured to obtain a disease prognosis or determine a therapeutic response. For example, in some embodiments, CASAI treatment is performed with a target cancer antigen and therapeutic outcome or therapeutic response is determined by measuring the level of antibodies reactive to one or more predetermined biomarker antigens that include the target cancer antigen and one or more other biomarker antigens.

As used herein, the term "reactive antibody" refers to an antibody that binds to a target cancer antigen, or a biomarker antigen. For example a PAP reactive antibody refers to an antibody that binds to PAP. Furthermore, "antibody level reactive to," "reactive antibody level," "level of antibody reactive to," or the like refers to the level, e.g., serum concentration, of antibody that reacts with, or binds to, a specific antigen. For example, an "antibody level reactive to LGALS8" refers the serum concentration of antibodies that bind to LGALS8. As another example, determining an antibody level reactive to one or more of LGALS8 or KRAS, refers to determining the serum concentration of antibodies that bind to LGALS8, determining the serum concentration of antibodies that bind to KRAS, or determining both the serum concentration of antibodies that bind to LGALS8 and the serum concentration of antibodies that bind to KRAS. Antibody levels can be determined on an absolute or relative basis.

As used herein, the term "baseline antibody level" refers to a level or concentration of antibody specific for one or more pre-determined biomarker antigens that is measured prior to the start of a round of cancer immunotherapy treatment, or measured from a sample obtained prior to the start of a round of cancer immunotherapy treatment. Baseline antibody levels can include baseline IgA, IgD, IgE, IgG, or IgM, levels or baseline levels of one or more immunoglobulin subclasses, such as $IgG_1$, $IgG_2$, $IgG_3$, or $IgG_4$. For example, a patient may be identified as in need of cancer therapy and a baseline level of IgG reactive against one or more pre-determined biomarker antigens determined for that patient prior to the onset of treatment, or determined from a sample obtained prior to the onset of treatment. Additionally, or alternatively, a patient may have received cancer immunotherapy treatment (e.g., treatment with an immunomodulatory agent, treatment with cell specific active immunotherapy, or CASAI treatment) in the past, and a baseline antibody level may be determined prior to the onset of additional treatment, or determined from a sample obtained prior to the onset of treatment.

Alternatively, the "baseline antibody level" can refer to a generally accepted level or range that is expected of a patient whose immune system has not been activated, or has not recently been activated, to attack tumor cells. For example, the baseline antibody level can be a concentration of antibodies reactive to one or more predetermined biomarker antigens that is not indicative of a robust anti-cancer immune response or indicates a lack of a robust anti-cancer immune response. As another example, the baseline antibody level can be a concentration of antibodies reactive to one or more predetermined biomarker antigens that is generally found in an individual who does not suffer from cancer. Consequently, such baseline antibody levels can be obtained from a reference source, such as a book, a publication, a journal article, a database, a chart, a spreadsheet, or from the world-wide web. In some cases, the baseline antibody levels can be determined from a population of individuals that do not suffer from cancer.

Baseline antibody levels reactive to one or more predetermined antigens can be determined on an absolute or relative basis. For example, baseline antibody levels reactive to one or more predetermined antigens can be compared against a standard. In some cases, baseline antibody levels reactive to one or more predetermined antigens can be determined to be below the standard, above the standard, or significantly below or above the standard. In some embodiments, baseline antibody levels reactive to one or more predetermined biomarker antigens are expected to be low as the predetermined biomarker antigens are self-antigens.

As used herein, the term "post-treatment antibody level" refers to a level or concentration of antibody specific for one or more biomarker antigens that is determined after the start of a round of cancer immunotherapy treatment. Post-treatment antibody levels reactive to one or more predetermined antigens can be determined on an absolute or relative basis. Post-treatment antibody levels include post-treatment IgA, IgD, IgE, IgG, or IgM, levels or post-treatment levels of one or more immunoglobulin subclasses, such as $IgG_1$, $IgG_2$, $IgG_3$, or $IgG_4$. For example, a cancer therapy can be administered to a patient and a post-treatment level of IgG reactive against one or more pre-determined biomarker antigens determined for that patient after the onset of treatment.

Post-treatment antibody levels reactive to one or more pre-determined biomarker antigens can be obtained at any time after the onset of cancer immunotherapy. For example, one or more post-treatment levels of antibodies reactive to pre-determined biomarker antigens can be determined after about 2 days subsequent to the onset of cancer immunotherapy treatment. As another example, post-treatment antibody levels can be determined after about 1 week subsequent to the onset of cancer immunotherapy treatment. As another example, post-treatment antibody levels can be determined after at least about 1, 2, 3, 4, 5, 6, 7, 8, 9, 10, 11, 12, 13, 14, 15, 16, 17, 18, 19, 20, 21, 22, 23, 24, 25, or 26 weeks or more subsequent to the onset of cancer immunotherapy treatment. In some cases the samples can be stored and then analyzed to determine post-treatment antibody levels.

As used herein, the term "target cancer antigen" can refer to an antigen that is therapeutically administered to a cancer patient. In some cases, the target cancer antigen activates the immune system, or a component thereof, to recognize, bind to, attack, opsonize, phagocytose, or neutralize the antigen. For example, a patient can produce antibodies that bind to the target cancer antigen in response to treatment. Alternatively, the "target cancer antigen" can refer to an antigen that binds to an antibody that is therapeutically administered to a cancer patient.

III. Methods

In some embodiments, the present invention provides a method of determining a cancer patient's therapeutic response to CASAI treatment. The CASAI treatment includes the steps of:
i. obtaining a baseline antibody level reactive to one or more predetermined biomarker antigens (e.g., non-target predetermined biomarker antigens);
ii. treating the cancer patient with CASAI using the target cancer antigen;
iii. obtaining a post-treatment antibody level reactive to the one or more predetermined biomarker antigens (e.g., non-target predetermined biomarker antigens) from a patient blood sample after treating with CASAI; and,
iv. measuring differences between the baseline and post-treatment antibody levels reactive to the one or more predetermined biomarker antigens (e.g., non-target predetermined biomarker antigens) where an increase in the antibody level for the one or more predetermined biomarker antigens (e.g., non-target predetermined biomarker antigens) over their baseline level predicts a positive therapeutic response.

In some cases, the one or more predetermined biomarker antigens are selected from the group consisting of a) a biomarker antigen comprising the target cancer antigen and one or more other predetermined biomarker antigens; and b) one or more biomarker antigens that do not comprise the target cancer antigen.

A. Obtaining a Baseline Antibody Level

A baseline antibody level can be obtained in any way known in the art. For example, a baseline level of antibodies can be measured by enzyme-linked immunosorbant assay (ELISA). In some cases, one or more predetermined biomarker antigens can be immobilized on a solid support surface, and blood, serum, or a composition derived therefrom may be contacted with the immobilized biomarker antigens to allow binding of reactive antibodies, such as reactive IgA, IgD, IgE, IgG, IgM, or their subclasses, such as $IgG_1$, $IgG_2$, $IgG_3$, or $IgG_4$. An enzyme-labeled secondary antibody can then be bound to the reactive antibodies by contacting the surface with the secondary antibody labeled with a fluorophore or an enzyme such as horseradish peroxidase or alkaline phosphatase). The level of reactive antibodies can then be detected or measured by measuring the amount of fluorophore or enzyme bound to the surface.

Variations on the ELISA format for detection of reactive antibodies will be apparent to those of skill in the art. For example, detectable labels other than an enzyme such as a fluorophore, a radionuclide, or a chromophore can be linked to the secondary antibody. Similarly, alternative secondary detection reagents can be utilized. For example, protein A, protein G, or any other agent that binds IgG can be used to detect reactive IgG bound to a solid support surface upon which biomarker antigens are immobilized. As another example, reactive antibodies can be detected and measured in a label free manner. For example, biomarker antigens can be bound to a solid support surface and a sample of blood, serum, or a composition derived therefrom can be passed over the immobilized biomarker antigen. Binding of reactive antibody to the biomarker antigens can then be detected by interferometry or by measuring the change in refraction due to surface plasmon resonance.

Biomarker antigens can be immobilized for detection of a single biomarker in a single well, e.g. in a 24, 48, 96, or 384 well plate. Alternatively, biomarker antigens can be immobilized on a bead, e.g. a fluorescent bead as in, for example, the Luminex xMAP technology (www.luminexcorp.com/TechnologiesScience/xMAPTechnology/), or as a microarray, e.g. as in the ProtoArray platform (www.invitrogen.com/protoarray). In some cases, the fluorescent bead is spectrally distinguishable, which enables the use of multiplexed antigen-coupled beads for high-throughput parallel monitoring of multiple biomarker antigen-reactive antibody levels in sera. Biomarker antigens can be immobilized by non-specific adsorption to a support surface, by chemical reaction with the surface (e.g., reaction with lysine or N-terminal primary amine of the biomarker antigen), or by the use of a capture reagent such as a capture antibody.

In other embodiments, the baseline reactive antibody level can be determined without immobilizing the biomarker antigens on a surface. For example, antibodies in sera can be immobilized on a surface and one or more biomarker antigens can be contacted with the immobilized antibodies.

The biomarker antigens bound to the surface via the reactive antibodies can be detected through a label conjugated to the biomarker antigen or to a secondary detection reagent (e.g. a secondary antibody). Alternatively, the biomarker antigens bound to the surface via the reactive antibodies can be detected in a label free manner such as via interferometry or as a change in refractive index. The level of biomarker antigen bound to the surface is proportional to the level of reactive antibody.

In still other embodiments, the baseline reactive antibody level can be determined by observing the change in size as a reactive antibody is bound to a biomarker antigen. For example, the size of a labeled biomarker antigen can be measured by fluorescence anisotropy or using a size exclusion column. The biomarker antigen can be contacted with blood, serum, or a composition derived therefrom and an increase in the size of the labeled biomarker antigen can indicate the presence of reactive antibodies.

In some embodiments, baseline levels of antibody reactive to one or more of the following predetermined biomarker antigens are determined: PSA, KLK2, KRAS, ERAS, LGALS8, LGALS3, PAP, or PAP-GM-CSF, either individually or in any combination. In some cases, the predetermined biomarkers are one or more of, two or more of, three or more of, four or more of, five or more of, six or more of, seven or more of, any one of, any two of, any three of, any four of, any five of, any six of, any seven of, or the eight biomarker antigens selected from the group consisting of PSA, LGALS3, KRAS, ERAS, KLK2, LGALS8, PAP, and PAP-GM-CSF.

In some cases, the predetermined biomarker antigens are ERAS and any one of, any two of, any three of, any four of, any five of, any six of, or the seven biomarker antigens selected from the group consisting of PSA, LGALS3, KRAS, KLK2, LGALS8, PAP, and PAP-GM-CSF. In other cases, the predetermined biomarker antigens are KRAS and any one of, any two of, any three of, any four of, any five of, any six of, or the seven biomarker antigens selected from the group consisting of PSA, LGALS3, ERAS, KLK2, LGALS8, PAP, and PAP-GM-CSF. In other cases, the predetermined biomarker antigens are PSA and any one of, any two of, any three of, any four of, any five of, any six of, or the seven biomarker antigens selected from the group consisting of LGALS3, KRAS, ERAS, KLK2, LGALS8, PAP, and PAP-GM-CSF.

In some cases, the predetermined biomarker antigens are KLK2 and any one of, any two of, any three of, any four of, any five of, any six of, or the seven biomarker antigens selected from the group consisting of PSA, LGALS3, KRAS, ERAS, LGALS8, PAP, and PAP-GM-CSF. In some cases, the predetermined biomarker antigens are LGALS8 and any one of, any two of, any three of, any four of, any five of, any six of, or the seven biomarker antigens selected from the group consisting of PSA, LGALS3, KRAS, ERAS, KLK2, PAP, and PAP-GM-CSF. In yet other cases, the predetermined biomarker antigens are LGALS3 and any one of, any two of, any three of, any four of, any five of, any six of, or the seven biomarker antigens selected from the group consisting of PSA, LGALS8, KRAS, ERAS, KLK2, PAP, and PAP-GM-CSF. In some cases, the predetermined biomarker antigens include PAP or PAP-GM-CSF and any one of, any two of, any three of, any four of, any five of, or all of: PSA, KLK2, KRAS, ERAS, LGALS8, and LGALS3. In some cases, the predetermined biomarker antigens include any one or more of PSA, LGALS3, KRAS, ERAS, KLK2, or LGALS8, but not PAP, a fusion protein containing PAP, or PAP-GM-CSF.

In some embodiments, the target cancer antigen is, or contains, PSA and the predetermined biomarker antigens are the target cancer antigen (PSA) and one or more of the following non-target predetermined biomarker antigens: LGALS3, KRAS, ERAS, KLK2, or LGALS8. In some cases, the target cancer antigen is not PSA and the non-target predetermined biomarker antigens include PSA and one or more of LGALS3, KRAS, ERAS, KLK2, or LGALS8. In some cases, the predetermined biomarker antigens include a target cancer antigen used in CASAI treatment of a subject and one or more of the following non-target predetermined biomarker antigens: PSA, LGALS3, KRAS, ERAS, KLK2, or LGALS8.

In some cases, baseline levels of antibody reactive to one or more of the following non-target predetermined biomarker antigens are determined: PSA, KLK2, KRAS, ERAS, LGALS8, or LGALS3, either individually or in any combination. In some cases, the non-target predetermined biomarkers are one or more of, two or more of, three or more of, four or more of, five or more of, six of, or any one of, any two of, any three of, any four of, or any five of the non-target predetermined biomarker antigens selected from the group consisting of PSA, KLK2, KRAS, ERAS, LGALS8, and LGALS3.

In some cases, the non-target predetermined biomarker antigens are ERAS and any one of, any two of, any three of, any four of, or any five of the biomarkers antigens selected from the group consisting of PSA, KLK2, KRAS, LGALS8, and LGALS3. In other cases, the non-target predetermined biomarker antigens are KRAS and any one of, any two of, any three of, any four of, or any five of the biomarkers antigens selected from the group consisting of PSA, KLK2, ERAS, LGALS8, and LGALS3. In some cases, the non-target predetermined biomarker antigens are KLK2 and any one of, any two of, any three of, any four of, or any five of the biomarkers antigens selected from the group consisting of PSA, ERAS, KRAS, LGALS8, and LGALS3. In some cases, the non-target predetermined biomarker antigens are LGALS3 and any one of, any two of, any three of, any four of, or any five of the biomarkers antigens selected from the group consisting of PSA, KLK2, KRAS, LGALS8, and ERAS. In some cases, the non-target predetermined biomarker antigens are LGALS8 and any one of, any two of, any three of, any four of, or any five of the biomarkers antigens selected from the group consisting of PSA, KLK2, KRAS, ERAS, and LGALS3. In some cases, the non-target predetermined biomarker antigens are PSA and any one of, any two of, any three of, any four of, or any five of the biomarkers antigens selected from the group consisting of KLK2, KRAS, ERAS, LGALS8, and LGALS3.

In some cases, the prediction of a positive therapeutic outcome is determined by measuring antigen spread rather than measuring response to the cancer antigen to be utilized in CASAI treatment. In such cases, the cancer antigen utilized in the cancer treatment is not utilized as a biomarker antigen to determine baseline reactive antibody levels. For example, in some cases, the baseline levels of antibody reactive to a target cancer antigen (e.g., PAP or PAP-GM-CSF) are not measured, not utilized, or not required, to obtain a predicted therapeutic response.

B. Treating a Cancer Patient with CASAI, Cell Specific Active Immunotherapy, or an Immunomodulator Methods are provided herein for treating cancer patients with cancer immunotherapy. The treatment can be performed in vivo or ex vivo. In general, CASAI is performed by immunizing the patient against one or more cancer antigens. This immunization induces the immune system to attack tumor cells bearing the antigen. Methods of the present invention are useful for the treatment of any cancer type, for the prediction of treatment outcomes for any cancer type, or for the identification of additional targets suitable for use as a cancer vaccine antigen. For example, the present invention can be useful for a patient suffering from prostate cancer, melanoma, glioma, bladder cancer, urothelial cancer, lung cancer, breast cancer, or colorectal cancer.

In vivo CASAI includes methods in which one or more target cancer antigens are used to stimulate immune responses inside the patient. For example, one or more target cancer antigens can be injected into a patient to stimulate an immune response. In some cases, the target cancer antigens are purified polypeptides. For example, one or more purified target cancer antigens can be mixed with a pharmaceutical excipient and injected into a patient. In some cases, the polypeptides are fused to an immunomodulator such as GM-CSF, TNF; CD40L; CTLA4; CD28; FLT-3 ligand; an agonist of toll-like receptors TLR-2, 3, 4, 5, 6, 8, or 9; a checkpoint inhibitor such as an antibody against CTLA4, PD-1, or PD-L1; a cytokine such as IL-1, IL-4, IL-7, IL-12, IL-15 or IL-21; or an inhibitor of an immune suppressor, such as IL-10, IL-35, TGFβ, or IDO; or conjugated to an immunogenic carrier protein such as keyhole limpet hemocyanin (KLH). In some cases, the polypeptides are fused to a costimulatory molecule such as CD40, CD80, or CD86. In some cases, the cancer antigens are mixed with an adjuvant or other immunomodulator and injected into the patient to enhance the immune reaction. In some embodiments, the polypeptide cancer antigen is PAP or a PAP fusion protein. In some cases, the polypeptide cancer antigen is a PAP fusion protein consisting of PAP fused to GM-CSF.

Alternatively, in some cases, the target cancer antigens are not purified polypeptides. For example, the cancer antigens can be encoded by one or more expression cassettes. The expression cassettes can then be introduced into the body to stimulate an immune response. In some cases, the expression cassettes are packaged into a vector, such as a viral vector to ensure adequate transfection and expression. In some cases, the vector itself is the cancer antigen. For example, a virus (e.g., HEV, HPV, HBV, HCV, or a virus-like particle (VLP) made from capsid proteins derived therefrom) can be introduced into a patient. In some cases, the virus or VLP targets tumor cells (e.g. it binds to a cell surface protein found on or near tumor cells). The vector can elicit an immune response to cells that have taken up the vector. In some cases, the VLP can include a capsid fusion protein that includes a capsid protein, or a portion thereof, and a target antigen, or a portion thereof. In some cases, a virus or other package can carry an additional expression cassette encoding an immunomodulator. In some embodiments, the expression cassette encodes a fusion protein consisting of a target cancer antigen fused to GM-CSF, such as PAP-GM-CSF.

In some cases, CASAI treatment is performed under ex vivo conditions. Ex vivo CASAI includes methods in which antigen presenting cells (APCs) are extracted from the patient, contacted with antigen in vitro to produce activated APCs, and the activated APCs are then re-introduced into the patient. In some cases, the antigen presenting cells are expanded in vitro to provide a sufficient number of cells to induce a robust immune response. In some cases, the activated APCs are used to activate T-Cells, B-cells, or NK-cells in vitro, and the activated APCs, T-Cells, B-Cells, and/or NK-cells are then re-introduced into the patient.

In one embodiment, the invention provides a method of inducing a cytotoxic cell-mediated immune response in a human subject comprising the steps of (a) isolating APCs from the subject; (b) exposing the APCs in vitro to a protein conjugate comprising GM-CSF covalently linked to PAP, under conditions effective to activate APCs; (c) administering the activated APCs to the subject; and (d) repeating steps (a)-(c) at least once with each cycle beginning at least 10 days after step (c) has occurred. In another embodiment, steps (a)-(c) are repeated one time with step (a) occurring 14 days after step (c).

In another embodiment, a patient can be treated with cell specific active immunotherapy. For example, a patient can be treated with target cancer antigens that are a mixture of antigens derived from the patient's own tumor cells or allogenic tumor cells For example, one or more of the tumor cell lines, such as the prostate tumor LnCAP or PC-3 cell lines, can be killed, and a mixture of antigens (e.g., proteins) can be extracted therefrom. The mixture can be mixed with a pharmaceutical excipient and introduced into a patient. In some cases, the mixture is also combined with an adjuvant or an immunomodulator. In some cases, the treatment with syngenic or allogenic tumor cells can stimulate an immune response against (e.g., recognize, bind to, attack, opsonize, induce apoptosis or necrosis, phagocytose, etc.) the patient's cancer cells. In some embodiments, an increase in one or more predetermined biomarker antigens as a result of treatment with a mixture of antigens derived from the patient's own tumor cells or allogenic tumor cells can predict a positive therapeutic outcome.

In yet another embodiment, a patient can be treated with an immunomodulator, such as one or more immunomodulators described herein. In some cases, treatment with an immunomodulator that activates the immune system or inhibits a suppressor (e.g., a checkpoint) of the immune system can result in increased immune surveillance or activity (e.g., recognition, binding to, opsonization of, induction of apoptosis or necrosis, phagocytosis, etc.) against a patient's cancer cells. In some cases, an increase in one or more predetermined biomarker antigens as a result of treatment with an immunomodulator can predict a positive therapeutic outcome.

In yet another embodiment, self-antigen reactive antibody levels of a patient or population of patients suffering from cancer can be measured and correlated with overall survival. Levels of antibodies that are reactive to a particular biomarker antigen or group of biomarker antigens that correlate with improved overall survival can then identify that antigen or group of antigens as target antigens for cancer immunotherapy. In some cases, an increase in the levels of antibodies reactive to one or more biomarker antigens that correlates with improved overall survival can identify those one or more biomarker antigens as target antigens for cancer immunotherapy. In some cases, the increase in the levels of antibodies reactive to one or more biomarker antigens is an increase from pre-treatment levels to post-treatment levels. In some cases, the biomarker antigens include, or are, any one or more of PSA, KLK2, KRAS, ERAS, LGALS8, LGALS3, PAP, or PAP-GM-CSF, individually or in any combination, such as any of the foregoing combinations described herein. In some cases, non-target predetermined biomarker antigens are measured and compared to determine the presence, absence, or degree of increase in reactive antibodies. In some cases, the non-target predetermined biomarker antigens include, or are, any one or more of KLK2, KRAS, ERAS, LGALS8, LGALS3, or PSA, individually or in any combination, such as any of the foregoing combinations described herein.

C. Measuring the Difference Between Baseline Antibody Levels and Antibody Levels Induced by CASAI Treatment, Cell Specific Active Immunotherapy, or Treatment with an Immunomodulator Differences between baseline antibody levels and the levels of antibodies induced by cancer immunotherapy treatment that are reactive to one or more predetermined biomarker antigens can be utilized to identify patients that are responding to the treatment, identify additional antigens suitable for use as a target cancer antigen, or predict therapeutic outcomes. For example, patients that increase reactive antibodies to certain predetermined biomarker antigens (e.g., non-target predetermined biomarker antigens) in response to CASAI treatment, cell specific active immunotherapy, or treatment with an immunomodulator can exhibit prolonged overall survival, decreased recurrence, greater reduction in tumor load, or a lack of disease progression as compared to patients in which reactive antibody levels are not increased or are not substantially increased by treatment. As such, it can be desirable to identify patients in which the levels of antibody reactive to one or more predetermined biomarker antigens (e.g., non-target predetermined biomarker antigens) are increased in response to treatment.

The pre and post-treatment levels of antibody reactive to predetermined biomarker antigens can be determined using any methods known in the art. Detection and measurement of pretreatment antibody levels (i.e. baseline antibody levels) are described above. Compositions and methods for detecting and measuring antibody levels induced by cancer immunotherapy treatment (e.g., CASAI, cell specific active immunotherapy, or treatment with an immunomodulator) are identical except that the antibodies are obtained from blood, serum, or a composition derived therefrom after treatment has begun, including after treatment has been completed, or after a round of treatment has been completed. In some cases, blood or sera are collected during treatment and used for comparison to baseline antibody levels to predict therapeutic outcome. Blood or sera can be collected and analyzed for reactive antibodies at any time point after the start of treatment. For example, blood or sera may be collected 1 week into the treatment regime, or 2, 3, 4, 5, 6, 7, 8, 9, 10, 11, 12, 13, 14, 15, 16, 17, 18, 19, 20, 22, 24, or 26 weeks or more after the start of treatment.

For example, the baseline level of antibodies reactive to one or more predetermined biomarker antigens (e.g., one or more of PSA, KLK2, KRAS, ERAS, LGALS8, LGALS3, PAP, or PAP-GM-CSF) can be determined by ELISA using serum obtained from a patient before the onset of treatment. As another example, the baseline level of antibodies reactive to one or more non-target predetermined biomarker antigens (e.g., one or more of PSA, KLK2, KRAS, ERAS, LGALS8, or LGALS3) can be determined by ELISA using serum obtained from a patient before the onset of treatment. As yet another example, the baseline level of antibodies reactive to a target cancer antigen and one or more non-target predetermined biomarker antigens (e.g., one or more of PSA, KLK2, KRAS, ERAS, LGALS8, or LGALS3) can be determined by ELISA using serum obtained from a patient before the onset of treatment. In some cases, the baseline level can be a predetermined reference or threshold value for pretreatment reactive antibody levels.

The patient can then undergo cancer immunotherapy treatment (e.g., CASAI treatment such as sipuleucel-T treatment, cell specific active immunotherapy, or treatment with an immunomodulator), and blood or serum obtained after the onset of the treatment regime. The serum concentration of antibodies reactive to the one or more predetermined biomarker antigens (e.g., non-target pre-determined biomarker antigens) in the post-treatment samples thus obtained can then be determined and compared to the baseline levels. In some cases, patients exhibiting post-treatment levels of antibodies reactive to one or more predetermined biomarker antigens above a threshold can then be identified as responding to the treatment and/or likely to have a positive therapeutic outcome.

In some cases, patients exhibiting a post-treatment increase above a baseline level of antibodies reactive to one or more predetermined biomarker antigens (e.g., non-target predetermined biomarker antigens) can be identified as responding to the treatment and/or likely to have a positive therapeutic outcome. In some cases, the increase in reactive antibody levels can indicate a probability of prolonged overall survival, decreased recurrence, greater reduction in tumor load, or a lack of disease progression. In some cases, patients can be segregated into non-responders and responders on the basis of a measured increase of the level of antibodies reactive to one or more predetermined biomarker antigens over a baseline value. In some cases, the responders are predicted to have a better therapeutic outcome (e.g., a higher likelihood of remission or non-progression) as compared to the non-responders.

In some embodiments, the methods provide for measuring cancer immunotherapy treatment induced elevation of the levels of antibodies (e.g., in comparison to the baseline levels) reactive to one or more of the following predetermined biomarker antigens: PSA, KLK2, KRAS, ERAS, LGALS8, LGALS3, PAP, and PAP-GM-CSF. In some cases, the predetermined biomarker antigens are one or more of, two or more of, three or more of, four or more of, five or more of, any two of, any three of, any four of, any five of, any six of, any seven of, or the eight following biomarker antigens: PSA, LGALS3, KRAS, ERAS, KLK2, LGALS8, PAP, and PAP-GM-CSF. In some cases, the predetermined biomarker antigens include one or more of, two or more of, three or more of, four or more of, five or more of, any two of, any three of, any four of, any five of, or the six following non-target predetermined biomarker antigens: PSA, LGALS3, KRAS, ERAS, KLK2, and LGALS8. In some cases, the method provide for measuring cancer immunotherapy treatment induced elevation of the levels of antibodies (e.g., in comparison to the baseline levels) reactive to a target cancer antigen and one or more of the following non-target predetermined biomarker antigens: PSA, KLK2, KRAS, ERAS, LGALS8, and LGALS3. In some cases, the predetermined biomarker antigens include a target cancer antigen and one or more of, two or more of, three or more of, four or more of, five or more of, any two of, any three of, any four of, any five of, or the six following non-target predetermined biomarker antigens: PSA, LGALS3, KRAS, ERAS, KLK2, and LGALS8.

In some cases, the predetermined biomarker antigens are ERAS and any one of, any two of, any three of, any four of, any five of, any six of, or the seven following biomarker antigens: PSA, LGALS3, KRAS, KLK2, LGALS8, PAP, or PAP-GM-CSF. In other cases, the predetermined biomarker antigens are KRAS and any one of, any two of, any three of, any four of, any five of, any six of, or the seven following biomarker antigens: PSA, LGALS3, ERAS, KLK2, LGALS8, PAP, or PAP-GM-CSF. In other cases, the predetermined biomarker antigens are KLK2 and any one of, any two of, any three of, any four of, any five of, any six of, or the seven following biomarker antigens: PSA, LGALS3, ERAS, KRAS, LGALS8, PAP, or PAP-GM-CSF. In other cases, the predetermined biomarker antigens are PSA and any one of, any two of, any three of, any four of, any five of, any six of, or the seven following biomarker antigens: KRAS, LGALS3, ERAS, KLK2, LGALS8, PAP, or PAP-GM-CSF. In other cases, the predetermined biomarker antigens are LGALS3 and any one of, any two of, any three of, any four of, any five of, any six of, or the seven following biomarker antigens: PSA, KRAS, ERAS, KLK2, LGALS8, PAP, or PAP-GM-CSF. In other cases, the predetermined biomarker antigens are LGALS8 and any one of, any two of, any three of, any four of, any five of, any six of, or the seven following biomarker antigens: PSA, LGALS3, ERAS, KLK2, KRAS, PAP, or PAP-GM-CSF.

In some cases, the predetermined biomarker antigen is PSA. In some cases, the target cancer antigen is not PSA and the predetermined biomarker antigen is, or includes, PSA. In some cases, the target cancer antigen is PSA and the predetermined biomarker antigens are PSA and one or more of LGALS3, KRAS, ERAS, KLK2, LGALS8, PAP, and PAP-GM-CSF. In some cases, the target cancer antigen is PSA and the non-target predetermined biomarker antigens are one or more of LGALS3, KRAS, ERAS, KLK2, LGALS8, PAP, and PAP-GM-CSF. In some cases, the target cancer antigen is PAP or PAP-GM-CSF and the non-target predetermined biomarker antigens are one or more of PSA, LGALS3, KRAS, ERAS, KLK2, and LGALS8.

In some embodiments, the methods provide for measuring cancer immunotherapy treatment induced elevation of the levels of antibodies (e.g., in comparison to the baseline levels) reactive to one or more of the following non-target predetermined biomarker antigens: PSA, KLK2, KRAS, ERAS, LGALS8, or LGALS3. In some cases, the non-target predetermined biomarker antigens are one or more of, two or more of, three or more of, four or more of, five or more of, six of, any two of, any three of, any four of, or any five of the following non-target predetermined biomarker antigens: PSA, LGALS3, KRAS, ERAS, KLK2, or LGALS8.

In some cases, the prediction of a positive therapeutic outcome is determined by measuring antigen spread rather than measuring response to the target cancer antigen to be utilized in CASAI treatment. In some cases, the target cancer antigen utilized in the cancer treatment is therefore not utilized as a biomarker to determine baseline antibody levels, not used as a biomarker to predict therapeutic outcome, or is only used as a biomarker to predict therapeutic response in combination with other biomarkers. For example, in some cases, levels of antibody reactive to PAP or PAP-GM-CSF induced by sipuleucel-T treatment are not measured, are not compared to a baseline IgG level, or are not utilized to obtain a predicted therapeutic response. For example, in some cases, the predetermined biomarker antigens are, or include, any one or more of PSA, LGALS3, ERAS, KRAS, KLK2, or LGALS8 but do not include the target cancer antigen, e.g., do not include PAP, a fusion protein containing PAP, or PAP-GM-CSF. As another example, in some cases, the predetermined biomarker antigens are, or include, any one or more of PSA, LGALS3, ERAS, KRAS, KLK2, LGALS8, but do not include the target cancer antigen, e.g., do not include PAP, a fusion protein containing PAP, or PAP-GM-CSF.

Alternatively, in some cases, immune response to the target cancer antigen is measured in conjunction with one or more additional predetermined biomarker antigens. For example, the predetermined biomarker antigens can be, or include a target cancer antigen such as PAP or PAP-GM-CSF and any one or more non-target cancer antigens such as PSA, KLK2, KRAS, ERAS, LGALS8, or LGALS3.

An increase of at least about 1.2-200-fold in the level of IgG reactive to one or more biomarkers over the baseline reactive antibody level in response to treatment can indicate a positive therapeutic outcome. For example, an increase in reactive antibody levels above the baseline value by at least about 1.2-fold, 1.5-fold, 1.75-fold, 2-fold, 2.5-fold, 3-fold, 4-fold, 5-fold, 7.5-fold, 10-fold, 15-fold, 20-fold, 25-fold, 30-fold, 40-fold, 50-fold, or higher can be indicative of a positive therapeutic outcome. One of skill in the art will recognize that different antibody level detection techniques exhibit different sensitivities and dynamic ranges and thus the threshold for identifying an increase can depend on the method employed for antibody measurement.

Similarly, the threshold for identifying an increase in response to cancer immunotherapy treatment that is predictive of a positive therapeutic outcome can depend on the biomarker antigen. By way of example only, an increase in the level of antibody reactive to one biomarker antigen of at least 1.5-fold can be predictive of a positive therapeutic outcome. However, in this example, an increase in the level of IgG reactive to a different biomarker antigen must be at least 2-fold to be predictive of a positive therapeutic outcome. Similarly, the threshold for identifying an increase in response to cancer immunotherapy that is predictive of a positive therapeutic outcome can depend on the antibody isotype measured.

In some cases, measuring the increase of reactive antibody levels for more than one biomarker can increase the predictive power of the method. For example, a patient in which two or more predetermined biomarker reactive antibody levels are elevated in response to treatment can suggest a greater degree of antigen spread or an increased probability of having a positive therapeutic outcome as compared to a patient in which only one predetermined biomarker reactive antibody level is elevated or a patient which exhibits no response. For example, a patient in which antibodies reactive to both ERAS and KLK2 are elevated in response to treatment can be identified as having an increased likelihood of a positive therapeutic outcome. Similarly, reactive antibody levels for additional biomarkers (e.g., more than two biomarkers, more than three biomarkers, more than four biomarkers, more than five biomarkers, etc.) can be measured to further increase the predictive power of the method. For example, a patient in which antibodies reactive to ERAS, KLK2, and KRAS are increased relative to baseline values can be identified as having an increased likelihood of a positive therapeutic outcome. As another example, a patient in which antibodies reactive to PSA and one or more additional predetermined biomarker antigens are increased relative to baseline values can be identified as having an increased likelihood of a positive therapeutic outcome.

In some cases, post-treatment increases in antibody levels reactive to any one of a group of predetermined biomarker antigens can be indicative of a positive therapeutic outcome. For example, patients that exhibit a substantial (e.g., 1.2, 1.3, 1.4, 1.5, 2, 2.5, 3, 4, 5, 6, 7.5, 10, 15, 20, 25, 30, 40, or 50 fold or higher) increase in antibody levels reactive to any one of 2, 3, 4, 5, 6, 7, 8, 9, or 10 different predetermined biomarker antigens relative to a baseline level can be identified as likely to have a positive therapeutic outcome. For example, a patient may be identified as likely to have a positive therapeutic outcome if they exhibit an increase relative to a baseline level of antibody reactive to any one of PSA, KLK2, ERAS, KRAS, LGALS8, or LGALS3.

As yet another example, a patient may be identified as likely to have a positive therapeutic outcome if they exhibit an increase relative to a baseline level of antibody reactive to PSA and any one of KLK2, KRAS, ERAS, LGALS8, or LGALS3. As yet another example, a patient may be identified as likely to have a positive therapeutic outcome if they exhibit an increase relative to a baseline level of antibody reactive to KLK2 and any one or more of PSA, KRAS, ERAS, LGALS8, or LGALS3. As yet another example, a patient may be identified as likely to have a positive therapeutic outcome if they exhibit an increase relative to a baseline level of antibody reactive to KRAS and any one or more of PSA, KLK2, ERAS, LGALS8, or LGALS3. As yet another example, a patient may be identified as likely to have a positive therapeutic outcome if they exhibit an increase relative to a baseline level of antibody reactive to LGALS3 and any one or more of PSA, KRAS, ERAS, LGALS8, or KLK2. As yet another example, a patient may be identified as likely to have a positive therapeutic outcome if they exhibit an increase relative to a baseline level of antibody reactive to LGALS8 and any one or more of PSA, KRAS, ERAS, KLK2, or LGALS3. As yet one more example, a patient may be identified as likely to have a positive therapeutic outcome if they exhibit an increase relative to a baseline level of antibody reactive to a target cancer antigen and any one or more non-target predetermined biomarker antigens such as PSA, KLK2, KRAS, ERAS, LGALS8, or LGALS3.

Similarly, improved predictive power can be obtained by identifying patients that exhibit an increased level of antibodies reactive to at least any two of 3, 4, 5, 6, or more different predetermined biomarker antigens in response to cancer immunotherapy treatment. For example, a patient may be identified as likely to have a positive therapeutic outcome if they exhibit an increase relative to a baseline level of antibodies reactive to at least two of ERAS, KRAS, LGALS8, LGALS3, PSA, or KLK2. As another example, a patient may be identified as likely to have a positive therapeutic outcome if they exhibit an increase relative to a baseline level in IgG reactive to at least two of ERAS, KRAS, LGALS8, LGALS3, PSA, or KLK2. Similarly, a patient may be identified as likely to have a positive therapeutic outcome if they exhibit an increase relative to a baseline level in IgG reactive to at least three of ERAS, KRAS, LGALS8, LGALS3, PSA, or KLK2.

As yet another example, a patient may be identified as likely to have a positive therapeutic outcome if they exhibit an increase relative to a baseline level of antibodies reactive to at least four of ERAS, KRAS, LGALS8, LGALS3, PSA, or KLK2. As yet another example, a patient may be identified as likely to have a positive therapeutic outcome if they exhibit an increase relative to a baseline level of antibodies reactive to at least five of PSA, ERAS, KRAS, LGALS8, KLK2, or LGALS3. As yet another example, a patient may be identified as likely to have a positive therapeutic outcome if they exhibit an increase relative to a baseline level of antibodies reactive to the following predetermined biomarker antigens PSA, ERAS, KRAS, LGALS8, KLK2, and LGALS3. As yet another example, a patient may be identified as likely to have a positive therapeutic outcome if they exhibit an increase relative to a baseline level of antibodies reactive to a target cancer antigen and at least one of, two of, three of, four of, five of, or all six of the following non-target predetermined biomarker antigens: PSA, ERAS, KRAS, LGALS8, KLK2, or LGALS3.

In some cases, the level of antibodies reactive to the target cancer antigen are not utilized, or are only utilized in combination with the level of antibodies reactive to one or more other predetermined biomarker antigens to predict therapeutic outcome. For example, in some cases, PAP, PAP-GM-CSF, or both PAP and PAP-GM-CSF reactive antibody levels are not measured or are not utilized to predict therapeutic outcome. In other cases, PAP, PAP-GM-CSF, or both PAP and PAP-GM-CSF reactive antibody levels are measured and compared to baseline levels and one or more non-target predetermined biomarker antigen reactive antibody levels are also measured and compared to baseline to predict therapeutic outcome.

In some embodiments, methods are provided for predicting therapeutic outcome, or patient response by measuring baseline and treatment induced levels of antibodies reactive to one or more biomarker antigens or combinations thereof, and combining that information with other parameters identified as predictors of patient health or response to arrive at a final prediction of therapeutic outcome. Additional parameters include, but are not limited to overall patient health, tumor size, tumor stage or grade (e.g., Gleason score, AJCC TNM stage, Whitmore-Jewett stage, Nottingham Grading System); PSA level, presence of bone lesions, bisphosphonate usage, lactate dehydrogenase level, hematocrit level, age, nutrition, mobility, strength, energy, physical activity, mood, cognition, or the presence of comorbidities in a particular patient. Additional parameters can also include measures of immune response to the target cancer antigen utilized in a CASAI, or cell specific active immunotherapy, treatment. For example, CD54 upregulation, or the level of antibodies reactive to the target cancer antigen utilized in the treatment, e.g., PAP-GM-CSF reactive IgG level or PAP reactive IgG level.

One of skill in the art will appreciate that additional combinations of reactive antibody levels and/or additional parameters other than those explicitly taught herein can be useful for prediction of patient therapeutic outcome, identification of patients that are responding to treatment, or identification of antigens suitable for use as a cancer vaccine antigen. Moreover, it is understood that the present invention is not limited to those combinations that are explicitly taught.

IV. Biomarker Antigens

Biomarker antigens are provided herein that predict the therapeutic outcome of cancer immunotherapy treatment in patients. For example, patients in which a robust immune response is generated against the resident tumor cells by CASAI treatment can exhibit antigen spread. Such patients can exhibit increased levels of antibodies in their sera that are reactive to both the specific antigen utilized in the CASAI therapy (e.g., PAP-GM-CSF) and to other determinants such as other antigens present in the tumors. Detection of increased levels of antibody that are reactive to the antigen utilized in the CASAI therapy and/or other antigens present in the tumors can be indicative of a positive therapeutic response. Similarly, high levels, or increased levels relative to baseline, of antibodies reactive to such biomarker antigens can be predictive of a positive therapeutic response in patients who are treated with an immunomodulator. Moreover, reactive antibody levels that increase in response to cancer immunotherapy and are correlated with a positive therapeutic response can indicate that the biomarker antigen bound by such a reactive antibody is a good target cancer antigen for cancer immunotherapy, e.g., CASAI, in the same or a different patient.

Biomarker antigens include any antigen to which patients develop reactive IgGs in response to cancer immunotherapy treatment. Biomarker antigens further include those in which a change in reactive antibody levels in response to cancer immunotherapy treatment is predictive of therapeutic outcome. For example, biomarker antigens can be identified by obtaining baseline levels of antibodies reactive to any endogenous or heterologous protein or other antigen; treating the patient with any cancer immunotherapy method known in the art, measuring the change in antibodylevels reactive to the antigens tested in response to the treatment; recording patient therapeutic outcomes; and determining whether any change in antibody level reactive to a particular biomarker antigen or combination of biomarker antigens is predictive of therapeutic outcome. In some cases, candidate biomarkers can be determined in a high-throughput fashion, e.g., using a protein microarray or fluorscent bead technology, and validated using a lower throughput assay, such as ELISA. Validation can include the use of standard statistical methods as known in the art, including those described herein.

In some cases, the predetermined biomarker antigens are chosen by reference to an established cancer pathway map. For example, the Kyoto Encyclopedia of Genes and Genomes (KEGG) provides a resource of genes involved in colorectal cancer, pancreatic cancer, glioma, thyroid cancer, acute myeloid leukema, basal cell carcinoma, bladder cancer, prostate cancer, endometrial cancer, small cell lung cancer, and non small cell lung cancer. Similarly, Ingenuity provides a database of cancer signalling pathways that identifies gene products important for development of various types of cancer. One or more gene products, or a combination thereof, identified in these maps or pathways as relevant to a particular cancer pathway can be used as biomarker antigens for monitoring therapeutic response to or predicting therapeutic outcome from cancer immunotherapy treatment for that cancer type.

Alternatively, candidate biomarker antigens can be identified using high-throughput measurement of mRNA expression of cancer cells. For example, Taylor et al., 2010 reports genes overexpressed in prostate cancer cells. The corresponding gene products can be used as candidate targets for comparing baseline antibody levels reactive to one or more of these candidates, or a combination thereof, in comparison to the antibody levels in response to cancer immunotherapy treatment for prostate cancer.

As provided herein, predictive non-target biomarker antigens include one or more of the following non-target predetermined biomarkers: PSA, KLK2, KRAS, ERAS, LGALS8, or LGALS3, either individually, or in any combination, such as any of the foregoing combinations described herein. Such antigens are, in some cases, identified by testing a set of candidate antigens to determine if measurement of an increase in reactive antibody level of one or more of the candidate antigens can predict a positive response to active immunotherapy. A brief description of exemplary candidate antigens LGALS3, KRAS, ERAS, KLK2, and LGALS8 and their reported roles in cancer is provided herein:

LGALS3: Lectin, Galactoside-Binding, Soluble, 3 (Galectin-3):

LGALS3, a multifunctional lectin with diverse expression (Newlaczyl, et al., 2011; Perillo, et al., 1998), is known to have roles in cell adhesion, migration (San, et al., 2000) and prostate cancer progression (Newlaczyl, et al., 2011; Califice, et al., 2004). It is highly expressed in prostate tumors with expression decreasing in hormone-resistant tumors (Laderach, et al, 2013). Alterations in the cytoplasmic/nuclear expression pattern of LGALS3 correlate with prostate carcinoma progression (van den Brule, et al., 2000). LGALS3 knock-down leads to reduced cell migration, invasion, cell proliferation, and tumor growth in the prostates of nude mice (Wang, et. al., 2009). It is reported to be a pro-angiogenic molecule and a mediator of vascular endothelial growth factor (VEGF)- and basic fibroblast growth factor (bFGF)-mediated angiogenic responses (Markowska, et al., 2010). LGALS3 is a binding partner of K-Ras and activates K-Ras-mediated signaling (Elad, et al., 2004; Shalom-Feuerstein, et al., 2005). It is phosphorylated by c-Abl, a process that is modulated by PTEN (Balan, et al., 2012); the native but not the phosphorylated form of LGALS3 is cleaved by PSA (Balan, et al., 2012), potentially altering receptor-mediated signaling.

KRAS: v-Ki-ras2 Kirsten Rat Sarcoma Viral Oncogene Homolog:

K-Ras is a member of the mammalian Ras protein family. Oncogenic activating mutations in or aberrant expression of K-Ras is implicated in various malignancies, including prostate carcinomas. Among metastatic prostate tumors, 32% exhibit K-Ras mutation or over-expression (Taylor, et al., 2010) and 90% exhibit activation of the Ras/Raf signaling pathway (Taylor, et al., 2010).

ERAS: Embryonic Stem-Cell Expressed Ras:

E-Ras is a member of the small GTPase Ras protein family. Initially found only in embryonic stem (ES) cells, E-Ras plays a crucial role in the transformation of transplanted ES cells to teratomas (Takahashi, et al., 2003). In gastric carcinomas, it is expressed (as determined by immunohistochemistry) in about 40% of the tumors; expression was found to be significantly associated with metastasis to the liver (p<0.0001) and lymph nodes (p<0.05) (Kubota, et al., 2010). E-Ras is not yet characterized in the context of prostate cancer.

KLK2/hK2: Kallikrien Related Peptidase 2:

KLK2 is primarily expressed in prostatic tissue (Darson, et al., 1999) and is responsible for cleaving pro-prostate-specific antigen (PSA) into its enzymatically active form (Williams, et al., 2010). It is highly expressed in prostate tumor cells and may be a marker for prostate cancer risk and detection (Nam, et al., 2006; Nam, et al., 2003; Magklara, et al., 2000; Helo, et al., 2009; Raaijmakers, et al., 2007). Both PSA and KLK2 are produced by the same secretory epithelial cells in the prostate, and KLK2 is highly expressed in poorly differentiated cancer cells (Rittenhouse, et al., 1998).

1.1.9 LGALS8 (Galectin-8): Lectin, Galactoside-Binding, Soluble, 8 (Galectin-8, Prostate Carcinoma Tumor Antigen 1 [PCTA-1]:

LGALS8 was originally identified as a prostate carcinoma tumor antigen by surface epitope mapping and expression cloning (Su, et al., 1996). It is widely expressed in tumor tissues, including all the TNM (tumor-node-metastasis) stages of prostate tumors (Laderach, et al., 2013). Antibody responses to LGALS8 were observed in metastatic prostate cancer patients post-treatment with GVAX therapy (a whole cell prostate cancer vaccine comprised of two allogeneic prostate carcinoma cell lines, LNCaP and PC-3, modified to secrete GM-CSF) (Nguyen, et al., 2010).

In some cases, predetermined biomarker antigens can include any 1, 2, 3, 4, 5, 6, 7, or 8 of PSA, KLK2, KRAS, ERAS, LGALS8, LGALS3, PAP, or PAP-GM-CSF. In some cases, predetermined biomarker antigens can include PSA and any 1, 2, 3, 4, 5, 6, or 7 of KLK2, KRAS, ERAS, LGALS8, LGALS3, PAP, or PAP-GM-CSF. In some cases, predetermined biomarker antigens can include ERAS and any 1, 2, 3, 4, 5, 6, or 7 of PSA, KLK2, KRAS, LGALS8, LGALS3, PAP, PAP-GM-CSF. In some cases, predetermined biomarker antigens can include KRAS and any 1, 2, 3, 4, 5, 6, or 7 of PSA, KLK2, ERAS, LGALS8, LGALS3, PAP, or PAP-GM-CSF. In some cases, the predetermined biomarker antigens can include at least two of PSA, ERAS, KRAS, LGALS8, LGALS3, PSA, PAP, or PAP-GM-CSF.

In some embodiments, the predetermined biomarker antigens are non-target predetermined biomarker antigens. In some cases, the predetermined biomarker antigens are a combination of the target cancer antigen and one or more non-target predetermined biomarker antigens. In some cases, the non-target predetermined biomarker antigens are selected from the group consisting of KLK2, KRAS, ERAS, PSA, LGALS3, and LGALS8. In some cases, the non-target predetermined biomarker antigens are one or more of, two or more of, three or more of, four or more of, five or more of, six of, any two of, any three of, any four of, or any five of the following non-target predetermined biomarker antigens: PSA, LGALS3, KRAS, ERAS, KLK2, or LGALS8.

V. Statistical Methods

Statistical methods are provided herein for identifying and validating biomarkers useful in (i.) identifying patients that respond to CASAI treatment, (ii.) predicting positive therapeutic outcomes, and (iii.) additional CASAI treatment methods. Statistical methods are also provided herein for utilizing measured changes in reactive IgG levels to generate a predicted therapeutic outcome.

A. Statistical Methods for Identifying and Validating Biomarkers and Predicting Therapeutic Outcome Measured reactive antibody levels from the protein microarrays (e.g., the ProtoArray) or Luminex xMAP platforms in response to cancer immunotherapy treatment can be compared to baseline antibody levels using a paired t-test (parametric or non-parametric) or a variation thereof (such as the moderated paired t-test implemented in 'Limma' R/Bioconductor) as described in (Smyth, et al., 2004; Smyth G K, 2005) to generate a t-statistic and a p-value that indicates the statistical confidence that the measured change is significant. In some cases, the results of such tests can be filtered by applying certain thresholds or heuristics, e.g., by removing measured IgG levels that do not exceed a threshold background level, or do not meet a threshold of statistical confidence (e.g., do not have a p-value at or below 0.05). Similarly, biomarker antigens that are poorly annotated (i.e., there is little or no information regarding the protein product or the function of the gene) can be removed from further follow-up. In some cases, a Benjamini and Hochberg procedure can be performed on statistical confidence measures to obtain multiple-testing adjustment of p-values and an estimated false discover rate (FDRs, percent false discoveries estimated at a certain p-value) (Benjamini, 1995).

In some embodiments, signal intensities (e.g., $\log_2$) of pre- and post-treatment reactive IgG levels for one or more biomarker antigens can be obtained by Luminex xMAP and compared using a one-sided paired Wilcoxon signed rank test. In some cases, fold-changes in reactive IgG levels after treatment can be compared using a one-sided Wilcoxon rank sum test. In some cases, an antigen response can be defined using an ad hoc threshold to filter out changes that are not statistically significant, or are not likely to be statistically significant. For example, in some cases, an "IgG response" to an antigen can be defined as an increase in the reactive antibody level from pre- to post-treatment of at least about 1.2-fold, 1.5-fold, 2-fold, 2.5-fold, 3-fold, or higher.

The association between biomarkers and therapeutic outcome such as overall survival (OS) can be observed via the use of Kaplan-Meier analysis. Kaplan-Meier analysis allows estimation of survival over time even when patients drop out or are studied for different lengths of time. In Kaplan-Meier analysis, the probability of surviving to a given point in time is estimated from the cumulative probability of surviving each of the preceding time intervals. In some cases, variables that affect the cumulative probability of survival as shown via Kaplan-Meier analysis can then be clustered to identify whether any particular groups (e.g., those with particular changes in biomarker reactive IgG levels) are associate with a greater positive therapeutic outcome (e.g. associated with longer overall survival).

Alternatively, or in addition, if there are an adequate number of data points, the association between a reactive antibody level or a combination of reactive antibody levels and a positive therapeutic outcome can be examined using a Cox proportional hazard model. In some cases, a Cox proportional hazard model analysis can be performed using all known variables, i.e. using a "full model" (e.g., reactive antibody response (e.g., high, low, or no response), PSA level, lactate dehydrogenase level, bone lesions, Gleason score, bisphosphonate usage, etc.). This full model can provide a p-value for rejecting the null hypothesis (e.g., p-value for rejecting the hypothesis that the antibody response is not associated with increased overall survival). The full model can also provide a hazard ratio estimate. A hazard ratio below 1 indicates the explanatory variable (e.g., reactive antibody response to treatment) is associated with longer overall survival.

A Cox proportional hazard model analysis can also be performed without the antibody response status, i.e. using a "base model", which includes prognostic and clinical factors (e.g., PSA level, lactate dehydrogenase level, Gleason score, etc.), without the variable indicating antibody response. The base model can be compared to the full model with a likelihood ratio test using a chi-square statistic with 1 degree of freedom. This can provide a p-value which indicates whether the explanatory variable (e.g., reactive antibody response to treatment) provides a statistically significant improvement in the predicted outcome.

In some embodiments, the association between pre- and post-treatment changes in IgG-levels, or IgG responses, with overall survival (OS) can be analyzed using a two-sided Wald test on the basis of a Cox proportional hazard model. Associations can, for example, be evaluated using (i) the fold-change ($\log_2$) in serum IgG level from pre- to post-treatment; and (ii) IgG response status (yes/no), using univariate or multivariate models adjusted for baseline risk factors, such as PSA and lactate dehydrogenase (LDH) levels. Baseline PSA ($\log_{10}$) and LDS ($\log_{10}$) values can be selected for use in multivariate models following the modeling approach used in other analyses of cancer antigen specific active immunotherapy (CASAI) (Kantoff, et al., 2010; Sheikh, et al., 2013).

VI. Systems

Provided below are descriptions of some devices (and components of those devices) that may be used in the systems and methods described above. These devices may be used, for instance, to communicate, process, and/or store data related to any of the functionality described above. As will be appreciated by one of ordinary skill in the art, the devices described below may have only some of the components described below, or may have additional components.

Figure 6A:
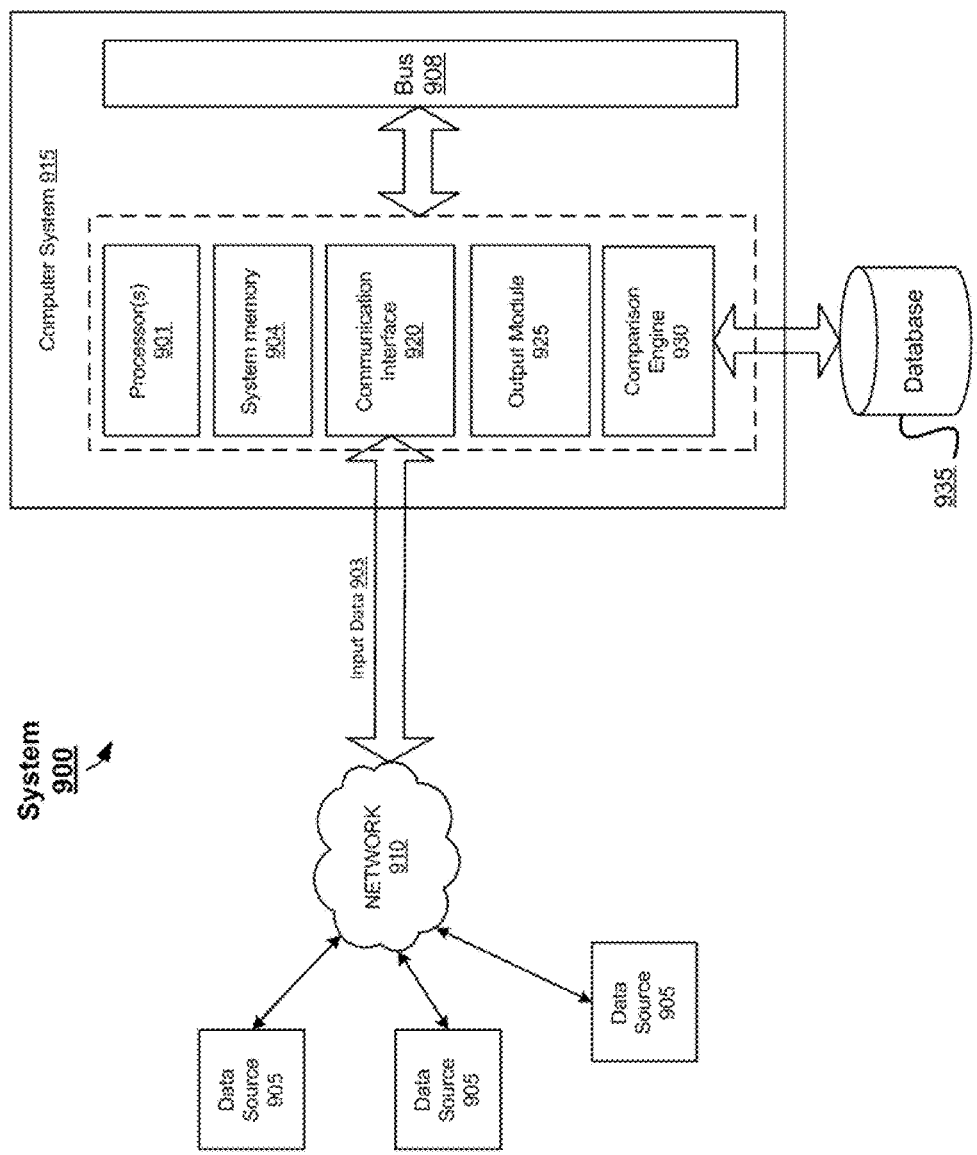
FIG. 6: (A): Depicts an example block diagram of a management system configured to determine a cancer patient's therapeutic response to cancer antigen specific active immunotherapy (CASAI) treatment with a target cancer antigen according to one embodiment. (B): Depicts an example flowchart of a process for determining a cancer patient's therapeutic response to cancer antigen specific active immunotherapy (CASAI) treatment with a target cancer antigen according to one embodiment.

FIG. 6A depicts an example block diagram of a management system configured to determine a cancer patient's therapeutic response to cancer immunotherapy, such as cancer antigen specific active immunotherapy (CASAI) treatment with a target cancer antigen, according to one embodiment. In the illustrated embodiment, system 900 includes a computer system 915 coupled to a plurality of data sources 905 over a network 910. The techniques described herein are not limited to any particular type of computer system or computer network. For instance, network 915 can be a local area network (LAN), a wide-area network (WAN), a wireless network, a bus connection, an interconnect, or any other means of communicating data or control information across one or more transmission lines or traces in an electronic system. For instance, data sources may be received manually at a user interface connected directly with computer system 915. Other embodiments are possible.

Computer system 915 includes a processor 901 and a system memory 904 coupled together via an interconnect bus 908. In other embodiments, processor 901 and system memory 904 can be directly interconnected, or can be connected indirectly through one or more intermediary components or units. Processor 901 and system memory 904 can be any general-purpose or special-purpose components as is known in the art and is not limited to any particular type of processor or memory system. System memory can be configured to store system and control data for use in the embodiments described herein. Computer system 915 may also be coupled with a database 935 (internal or external) to receive data.

Computer system 915 receives input data 903 from the various sources at communications interface 920. Computer system 915 processes the received data and provides resulting data at its output via output module 925. In a preferred embodiment, computer system receives a first set of data values representing baseline antibody levels and provides those values to the comparison engine 930. The computer system can receive a second set of data values representing post-treatment antibody levels and provide those values to the comparison engine 930. Comparison engine 930 can be configured to compare the pre-treatment antibody levels with the post-treatment levels to determine if there has been a change in antibody levels due to the treatment.

Specifically, comparison engine 930 can be configured to compare each value of the baseline antibody levels received in the first set of data values with a corresponding value of the post-treatment antibody levels of the second set of data values to determine whether they are equal or different. In one embodiment, if a difference is determined between the two values by the comparison engine 930, a signal indicating such may be asserted by the comparison engine. Similarly, in an alternate embodiment, if the two values are determined to be equal, a signal indicating such can be asserted by the comparison engine. In another embodiment, the signal is asserted by the comparison engine if the post-treatment antibody level reactive to a predetermined antigen is determined to be greater, or significantly greater, than the baseline antibody level. In yet another embodiment, the signal is asserted by the comparison engine if the post-treatment antibody level reactive to a predetermined antigen is determined not to be greater, or determined not to be significantly greater, than the baseline antibody level. In some cases, the threshold for significance can be a statistical value, e.g., an antibody level is significantly greater if the measured value satisfies a statistical cut-off such as a specified t-value or p value, e.g., $p \leq 0.05$. In other cases, the threshold for significance can be based on an empirically determined value. For example, in some cases, the comparison engine identifies baseline and post-treatment antibody levels as different if they differ by about 1.1, 1.2, 1.5, 2, 2.5, 3, 5, 7, 10-fold or more.

Comparison engine 930 may be implemented using specially designed computer hardware or circuitry or general-purpose computing hardware programmed by specially designed software modules or components; or any combination of hardware and software. The techniques described herein are not limited to any specific combination of hardware circuitry or software. For instance, comparison engine 930 may include off-the-shelf comparator circuitry components or custom-designed comparator circuitry. The comparator circuitry is configured to compare two or more values and to output a result indicating whether the two values are equal or not equal as is well understood by skilled artisans. Alternatively, the comparison functionality may be performed in software stored in memory 904 and executed by the processor 901.

Figure 6B:
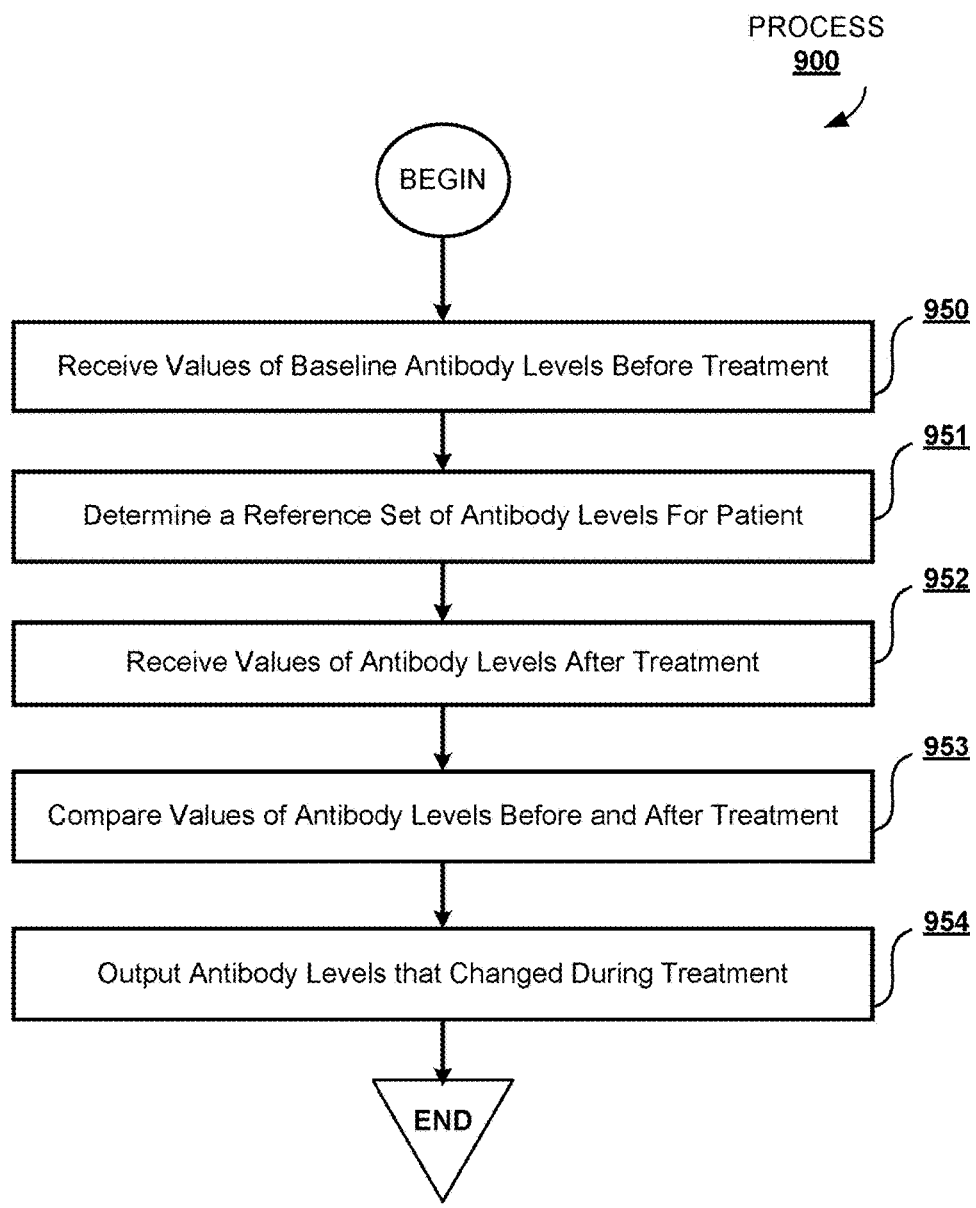

FIG. 6B depicts an example flowchart of a process for determining a cancer patient's therapeutic response to cancer immunotherapy, such as cell specific active immunotherapy, treatment with an immunomodulator, or (CASAI) treatment with a target cancer antigen, according to one embodiment. In the illustrated embodiment, process 900 begins at operation 950 where a first set of electronic data signals are received at a communications interface of a computer system. The first set of electronic data signals represents a set of interrelated pre-treatment values, each pre-treatment value indicative of a baseline antibody level reactive to one or more predetermined biomarker antigens before treatment. In one embodiment, the treatment is CASAI with a target cancer antigen and the predetermined biomarker antigens are selected from (1) a biomarker antigen including the target cancer antigen and one or more other predetermined biomarker antigens or (2) biomarker antigens that do not comprise the target cancer antigen.

Process 900 continues at operation 951 where a reference set of antibody level values can be defined from the set of pre-treatment values indicative of a baseline antibody level reactive to one or more predetermined biomarker antigens before CASAI treatment. The reference set of antibody level values can serve as the baseline antibody level for a particular patient. In one embodiment, the computer system automatically determines the reference set of values from the pre-treatment. In other embodiments, the reference set of values can be entered into the system manually (e.g., by a medical professional). For instance, upon initialization of the computer system, the system can be directed to retrieve the pre-treatment set of values, e.g., from system memory 904 or using a query to database 935, and to provide those values to the comparison engine 930 for analysis. In other embodiments, the computer system receives additional inputs to make the determination of the reference set of values from the pre-treatment set of values. The system can then provide a set of output data signals representing which of the set of post-treatment values have changed from the set of pre-treatment values. For instance, the system can determine which of the pre-treatment values have increased. In at least certain embodiments, an increase in the antibody levels reactive to one or more of the predetermined biomarker antigens over their baseline level can predict a positive therapeutic response to the treatment. In other embodiments, an increase in the antibody levels reactive to one or more of the predetermined biomarker antigens over their baseline level can provide target cancer antigens suitable for use in CASAI treatment.

Process 900 continues by receiving, at the communications interface, a second set of electronic data signals communications interface representing a set of post-treatment values corresponding to the set of pre-treatment values, each of the post-treatment values indicating an antibody level reactive to one or more of the predetermined biomarker antigens from a patient blood sample after treating with cancer immunotherapy. The pre-treatment values can then be compared to the post-treatment values (operation 953) to determine which of the set of post-treatment values have changed from the set of pre-treatment values. Alternatively, if a reference set of values was determined at operation 951, then the reference set can be compared to the post-treatment values. The system can then provide a set of output data signals representing which of the set of post-treatment values have changed from the set of pre-treatment values. For instance, the system can determine which of the pre-treatment values have increased. In another instance, the system can determine which of the pre-treatment values is significantly increased, using for example a statistical cutoff. In at least certain embodiments, an increase in the antibody levels reactive to one or more of the predetermined biomarker antigens over their baseline level can predict a positive therapeutic response to the treatment. In some embodiments, the change in the antibody levels reactive to one or more of the predetermined biomarker antigens relative to their baseline levels can be input into a hazard model, such as the Cox proportional hazard model described herein in equation (1) to predict a therapeutic outcome, or provide a measure of therapeutic response. In some cases, the computation of the proportional hazard is performed on the same system as the comparison between baseline and post-treatment reactive antibody levels. This completes process 900 according to one example embodiment.

It should be appreciated that the specific operations illustrated in FIG. 6B depict a particular embodiment of a process for monitoring events in an IT environment. Other sequences of operations may also be performed in alternative embodiments. For example, alternative embodiments may perform the operations outlined above in a different order. Moreover, the individual operations may include multiple sub-steps that may be performed in various sequences as appropriate and additional operations may be added or removed depending on the particular applications. One of ordinary skill in the art would recognize the many possible variations, modifications, and alternatives.

Figure 7:
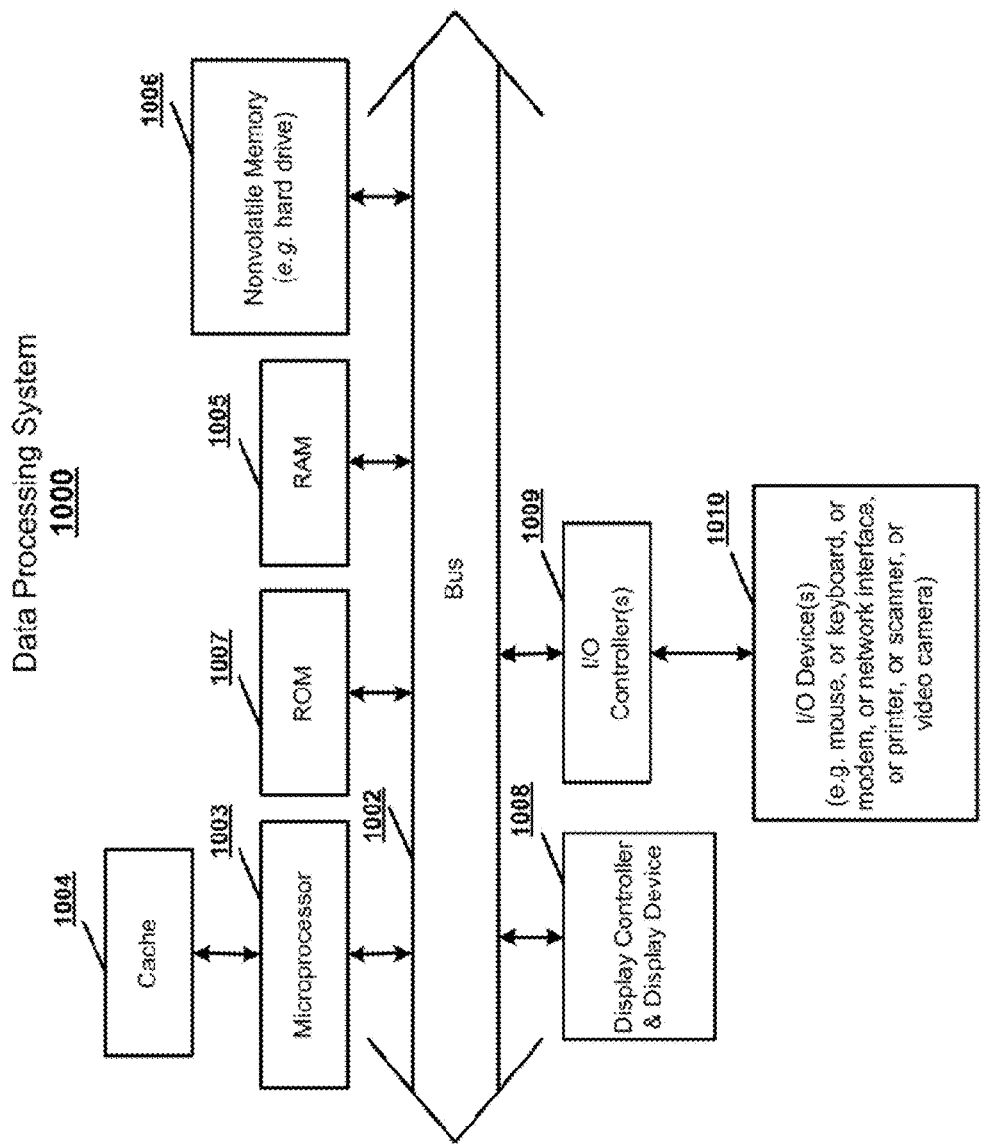
FIG. 7 depicts an example block diagram of a data processing system upon which the disclosed embodiments may be implemented.

FIG. 7 depicts an example block diagram of a data processing system upon which the disclosed embodiments may be implemented. Embodiments of the present invention may be practiced with various computer system configurations such as hand-held devices, microprocessor systems, microprocessor-based or programmable user electronics, minicomputers, mainframe computers and the like. The embodiments can also be practiced in distributed computing environments where tasks are performed by remote processing devices that are linked through a wire-based or wireless network.

FIG. 7 shows one example of a data processing system, such as data processing system 1000, which may be used with the present described embodiments. Note that while FIG. 7 illustrates various components of a data processing system, it is not intended to represent any particular architecture or manner of interconnecting the components as such details are not germane to the techniques described herein. It will also be appreciated that network computers and other data processing systems which have fewer components or perhaps more components may also be used. The data processing system of FIG. 7 may, for example, be a personal computer (PC), workstation, tablet, smartphone or other hand-held wireless device, or any device having similar functionality.

As shown, the data processing system 1001 includes a system bus 1002 which is coupled to a microprocessor 1003, a Read-Only Memory (ROM) 1007, a volatile Random Access Memory (RAM) 1005, as well as other nonvolatile memory 1006. In the illustrated embodiment, microprocessor 1003 is coupled to cache memory 1004. System bus 1002 can be adapted to interconnect these various components together and also interconnect components 1003, 1007, 1005, and 1006 to a display controller and display device 1008, and to peripheral devices such as input/output ("I/O") devices 1010. Types of I/O devices can include keyboards, modems, network interfaces, printers, scanners, video cameras, or other devices well known in the art. Typically, I/O devices 1010 are coupled to the system bus 1002 through I/O controllers 1009. In one embodiment the I/O controller 1009 includes a Universal Serial Bus ("USB") adapter for controlling USB peripherals or other type of bus adapter.

RAM 1005 can be implemented as dynamic RAM ("DRAM") which requires power continually in order to refresh or maintain the data in the memory. The other nonvolatile memory 1006 can be a magnetic hard drive, magnetic optical drive, optical drive, DVD RAM, or other type of memory system that maintains data after power is removed from the system. While FIG. 7 shows that nonvolatile memory 1006 as a local device coupled with the rest of the components in the data processing system, it will be appreciated by skilled artisans that the described techniques may use a nonvolatile memory remote from the system, such as a network storage device coupled with the data processing system through a network interface such as a modem or Ethernet interface (not shown).

With these embodiments in mind, it will be apparent from this description that aspects of the described techniques may be embodied, at least in part, in software, hardware, firmware, or any combination thereof. It should also be understood that embodiments can employ various computer-implemented functions involving data stored in a data processing system. That is, the techniques may be carried out in a computer or other data processing system in response executing sequences of instructions stored in memory. In various embodiments, hardwired circuitry may be used independently, or in combination with software instructions, to implement these techniques. For instance, the described functionality may be performed by specific hardware components containing hardwired logic for performing operations, or by any combination of custom hardware components and programmed computer components. The techniques described herein are not limited to any specific combination of hardware circuitry and software.

Embodiments herein may also be in the form of computer code stored on a computer-readable storage medium embodied in computer hardware or a computer program product. Computer-readable media can be adapted to store computer program code, which when executed by a computer or other data processing system, such as data processing system 1000, is adapted to cause the system to perform operations according to the techniques described herein. Computer-readable media can include any mechanism that stores information in a form accessible by a data processing device such as a computer, network device, tablet, smartphone, or any device having similar functionality. Examples of computer-readable media include any type of tangible article of manufacture capable of storing information thereon such as a hard drive, floppy disk, DVD, CD-ROM, magnetic-optical disk, ROM, RAM, EPROM, EEPROM, flash memory and equivalents thereto, a magnetic or optical card, or any type of media suitable for storing electronic data. Computer-readable media can also be distributed over a network-coupled computer system, which can be stored or executed in a distributed fashion.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1: Sipuleucel-T Treatment of Patients

PA2024 is a proprietary recombinant fusion protein containing PAP and GM-CSF sequences manufactured by Dendreon Corporation (Seattle, Wash.) for the investigational cellular immunotherapy sipuleucel-T. PA2024 is expressed in a baculovirus/Sf21 system.

All subject and healthy donor specimens were collected according to investigator sponsored protocols approved by the appropriate Investigational Review Board. After receiving informed consent, white blood cells were collected by apheresis and prepared for transport and/or processing. The subject's apheresis cells were centrifuged to remove autologous plasma, they are then resuspended in 0.9% sodium chloride USP solution and passed through a buoyant density solution (BDS) of 1.077 g/ml gravity. The interface cells were collected and washed in 0.9% sodium chloride USP solution after which they were then passed over a BDS 1.065 g/ml gravity separation solution. The cells that pass through the density solution were then collected and washed in 0.9% sodium chloride USP solution. These cells, termed BDS65 cells were cultured in AIM-V® culture medium for up to 44 hours with PA2024, a fusion protein comprising human prostatic acid phosphatase fused to human GM-CSF. The cultured cells were then washed out of the culture medium and resuspended in lactated ringers solution and were re-infused back into the subject. This process was performed three times, with each cycle of apheresis and culture being conducted two weeks apart.

Example 2: Profiling Humoral Response to Sipuleucel-T Therapy Using a Protein Microarray A. Samples for the Discovery of IgG Responses Post-Sipuleucel-T Treatment Using ProtoArray Pre- and post-treatment serum samples were available from a total of 224 patients from IMPACT (Kantoff et al., 2010; Sheikh et al., 2013) who provided consent; 155 in the sipuleucel-T arm and 69 in the control arm. Serum samples were collected from patients only up to the time of objective disease progression (Kantoff et al., 2010); consequently, samples were available from more patients at earlier time points than at later time points. In IMPACT, pairs of serum samples were evaluable as follows: (i) pre-treatment and week 2, n=204 (142 sipuleucel-T and 62 control patients); (ii) pre-treatment and week 10, n=132 (93 sipuleucel-T, 39 control); and (iii) pre-treatment and week 22, n=76 (60 sipuleucel-T, 16 control).

At the time of the ProtoArray analysis, serum samples from pre-treatment and all 3 post-treatment time points were available from 47 patients in the sipuleucel-T arm and 13 in the control arm in IMPACT. ProtoArray analyses were performed on samples from all 13 patients from the control arm, and a randomly chosen subset of 28 patients from the sipuleucel-T arm (to ensure successful analysis of roughly 25 samples from each time point). After eliminating failed assays and array quality control, ProtoArray data were available for analysis from the following patients: (i) pre-treatment and 2 weeks, 25 sipuleucel-T and 12 control, (ii) pre-treatment and 10 weeks, 24 sipuleucel-T and 11 control, (iii) pre-treatment and 22 weeks, 24 sipuleucel-T and 13 control.

B. Protein Microarray Profiling, Array Data QC & Normalization

ProtoArray v5.0 (Life Technologies Corporation) (Wolchock et al., 2009; Madan et al., 2010; Kantoff et al., 2010; Hodi et al, 2010; and Hoos et al., 2010) used proteins expressed using a baculovirus/Sf9 expression from Invitrogen's Ultimate™ ORF (open reading frame) collection, or from Gateway® collection of kinase clones developed by Protometrix. All ProtoArray assays were performed by Life Technologies Corporation using the manufacturer's recommended protocols. Microarray slides were blocked in blocking buffer (50 mM HEPES, 200 mM NaCl, 0.01% Triton X-100, 25% glycerol, 20 mM reduced glutathione, 1.0 mM DTT, 1× Synthetic Block) at 4° C. for 1 hour. After blocking, arrays were rinsed once with freshly prepared PBST buffer (1×PBS, 0.1% Tween 20, and 1× Synthetic Block). Arrays were then probed with a 1:500 dilution of each serum sample diluted in 5 mL of PBST buffer. Arrays were incubated for 90 minutes at 4° C. in QuadriPERM 4-well trays (Greiner) with gentle agitation. After incubation, slides were washed five times (5 minutes per wash) in 5 ml PBST Buffer in 4-well trays. An Alexa Fluor®647-conjugated goat anti-human IgG antibody diluted in 5 ml PBST buffer to a 1.0 μg/ml final concentration was added to each array and allowed to incubate with gentle shaking at 4° C. for 90 minutes. After incubation, secondary antibody was removed and arrays were washed as described above. Arrays were dried by spinning in a table top centrifuge equipped with a plate rotor at 200× gravity for 2 minutes, then scanned using the fluorescent microarray Tecan PowerScanner.

GenePix 6.0 software was used to map human proteins in the array list file to each array image with a fixed feature size of 130 μm (diameter). After aligning the arrays using spots from the AlexaFluor-conjugated and murine antibodies printed in each subarray, the features were resized by the GenePix software to best fit the feature. Pixel intensities for each spot on the array were determined from the software and saved to a file. All quantified spot files were processed using the LifeTechnology ProtoArray Prospector software to determine which proteins interacted with the samples. The software performed background correction and Robust Linear Model normalization (RLM) (Hoos et al., 2012) using appropriate control spots on the microarray.

Prior to analyses, signals on the microarray with low intensity across all samples and those from target antigens that did not have a known GenBank identifier (i.e., the target protein was poorly annotated or not annotated) were filtered out. This left IgG measurements to 7,221 protein isoforms on the ProtoArray, corresponding to 6,255 unique target antigens, with which all the subsequent analyses were performed.

C. Statistical Analyses

Statistical analyses were performed in the 'R' computing environment (cran.us.r-project.org/). Statistical tests were two-sided, unless stated otherwise. Changes in serum IgG levels are reported relative to pre-treatment (e.g., "fold-change in IgG level at week 10" refers to the ratio of IgG level at week 10 to that at pre-treatment).

To assess the statistical significance of pre- to post-treatment changes in levels of IgGs, normalized signal intensities ($\log_2$) from ProtoArray assays were tested using a moderated paired t-test (limma, R/Bioconductor) (Smyth G K, 2005). The Benjamini and Hochberg procedure was used to perform multiple testing adjustment of p-values and obtain estimated false discovery rates (FDRs, percent false discoveries estimated at a certain p-value) (Benjamini Y H, 1995).

To evaluate increases in IgG levels after treatment, pre- and post-treatment signal intensities ($\log_2$) from Luminex xMAP were compared using a one-sided paired Wilcoxon signed rank test. To evaluate if the fold-changes in IgG levels after treatment were higher in the sipuleucel-T group than in the control group, the values from the two groups were compared using a one-sided Wilcoxon rank sum test. 'IgG response' to an antigen was defined as ≥2-fold increase in signal intensity post-treatment compared to pre-treatment (ad-hoc threshold).

D. Paired Pre/Post Treatment Comparison to Determine Sipuleucel-T Induced Humoral Response To identify IgG antibodies induced in response to treatment, using protein microarrays the pre- & post-treated serum samples were compared using a moderated paired t-test (Limma) which is frequently used with microarray data (Smyth G K, 2004). Prior to the paired analysis, the antibodies that: (i) were not expressed beyond background signal of an array, with a p-value of 0.05, in at least 5% of the sipuleucel-T arm samples across the three post-treatment time points and (ii) did not have a known Refseq annotation for the target on the microarray (i.e. the target protein is poorly annotated) were eliminated. This left 7,221 antibodies with which all the downstream analyses were performed.

The number of antibodies up-regulated by 2-fold (with Benjamini and Hochberg estimated FDR≤10%) in the post-sipuleucel-T treatment group, relative to the pretreatment group, were 56, 162, and 23 at 6, 14, and 26 weeks respectively. The number of antibodies up-regulated by 3-fold (with Benjamini and Hochberg estimated FDR≤10%) in the post-sipuleucel-T treatment group, relative to the pretreatment group, were 4, 7, and 4 at 6, 14, and 26 weeks respectively. No antibodies were up-regulated post-placebo treatment (with estimated FDR≤10%). The top 30 antibody targets (with highest fold-up-regulation post-treatment relative to pretreatment, with estimated FDR≤10%) for each of the post-treatment time points are given in Table 1. PAP (or ACPP) is one of the top 30 antibody targets in all the post-treatment time points. Several top targets have been demonstrated to have direct roles in prostate cancer disease progression (such as LGALS3 or Galectin-3 (Wang, et al., 2009; Merseburger, et al., 2008; van den Brule, et al., 2000), ECE1 or endothelin converting enzyme 1 (Whyteside, et al., 2010; Lambert, et al., 2008; Dawson, et al., 2006; Kopetz, et al., 2002), ANPEP or aminopeptidase N (Guzman-Rojas, et al., 2012; Larkin, et al., 2012; Pasqualini, et al., 2000)).

TABLE 1A

Top 30 WK 6 up-regulated antibody targets (ACPP is noted in bold). Columns given are: protoArray spot location identifier; gene symbol; gene name; overall fold change post-treatment relative to BASIM in moderated paired t test; t-statistic from paired t test; p-value and adjusted (multiple testing corrected) p-value (Benjamini and Hochberg) in paired t test; and number of individuals in which the antibody is upregulated by 2-fold or more, with an intensity difference of at least 1000.

| Array Spot ID | Gene Symbol | Gene Name | Fold Change | T stat | P Value | Adj. P Value | Num Samples Exp. |
|---|---|---|---|---|---|---|---|
| 24_9_15 | ANPEP | alanyl (membrane) aminopeptidase (aminopeptidase N, aminopeptidase M, microsomal aminopeptidase, CD13, p150) (ANPEP) | 3.31 | 6.38 | 4.04E−07 | 2.54E−04 | 6 |
| 25_19_13 | CACNG1 | calcium channel, voltage-dependent, gamma subunit 1 (CACNG1) | 3.30 | 5.80 | 2.07E−06 | 2.88E−04 | 6 |
| 31_15_3 | LGALS3 | lectin, galactoside-binding, soluble, 3 (LGALS3) | 3.03 | 6.97 | 7.73E−08 | 1.86E−04 | 13 |
| 16_17_9 | FBXO21 | F-box protein 21 (FBXO21) | 3.02 | 5.06 | 1.77E−05 | 3.55E−04 | 4 |
| 20_22_1 | NAT5 | N-acetyltransferase 5 | 2.80 | 6.36 | 4.22E−07 | 2.54E−04 | 4 |
| 25_19_1 | LGALS3 | Galectin-3 | 2.73 | 6.98 | 7.48E−08 | 1.86E−04 | 12 |
| 41_8_17 | ECE1 | endothelin converting enzyme 1 (ECE1) | 2.64 | 5.00 | 2.07E−05 | 3.69E−04 | 8 |
| 19_14_15 | FBXO6 | F-box protein 6 (FBXO6) | 2.56 | 6.37 | 4.18E−07 | 2.54E−04 | 6 |
| 4_17_13 | LGALS3 | lectin, galactoside-binding, soluble, 3 (LGALS3) | 2.44 | 6.65 | 1.85E−07 | 2.23E−04 | 9 |
| 37_8_11 | FNDC3A | fibronectin type III domain containing 3A (FNDC3A), transcript variant 2 | 2.38 | 4.63 | 6.14E−05 | 4.79E−04 | 8 |
| 24_3_21 | CROP | cisplatin resistance-associated overexpressed protein (CROP) | 2.38 | 5.36 | 7.44E−06 | 3.22E−04 | 3 |

TABLE 1A-continued

Top 30 WK 6 up-regulated antibody targets (ACPP is noted in bold). Columns given are: protoArray spot location identifier; gene symbol; gene name; overall fold change post-treatment relative to BASIM in moderated paired t test; t-statistic from paired t test; p-value and adjusted (multiple testing corrected) p-value (Benjamini and Hochberg) in paired t test; and number of individuals in which the antibody is upregulated by 2-fold or more, with an intensity difference of at least 1000.

| Array Spot ID | Gene Symbol | Gene Name | Fold Change | T stat | P Value | Adj. P Value | Num Samples Exp. |
|---|---|---|---|---|---|---|---|
| 19_12_1 | SAAL1 | serum amyloid A-like 1 (SAAL1) | 2.36 | 5.06 | 1.77E−05 | 3.55E−04 | 6 |
| 14_4_3 | FN1 | fibronectin 1 (FN1) | 2.30 | 6.43 | 3.46E−07 | 2.54E−04 | 7 |
| 26_12_5 | WBSCR28 | Williams-Beuren syndrome chromosomal region 28 protein | 2.23 | 4.67 | 5.40E−05 | 4.57E−04 | 4 |
| 46_6_11 | NGLY1 | N-glycanase 1 (NGLY1) | 2.22 | 4.53 | 8.00E−05 | 5.41E−04 | 9 |
| 28_2_15 | VPS35 | vacuolar protein sorting 35 homolog (*S. cerevisiae*) (VPS35) | 2.21 | 5.07 | 1.70E−05 | 3.55E−04 | 4 |
| 23_9_7 | KLK2 | kallikrein-related peptidase 2 (KLK2), transcript variant 3 | 2.20 | 5.88 | 1.68E−06 | 2.88E−04 | 3 |
| 5_9_17 | MKNK2 | MAP kinase-interacting serine/threonine-protein kinase 2 | 2.16 | 5.79 | 2.16E−06 | 2.88E−04 | 5 |
| 40_2_15 | PHF20L1 | PHD finger protein 20-like 1 (PHF20L1) | 2.15 | 4.58 | 6.94E−05 | 5.06E−04 | 5 |
| 1_3_15 | BHMT2 | betaine-homocysteine methyltransferase 2 (BHMT2) | 2.15 | 5.58 | 3.96E−06 | 3.11E−04 | 6 |
| 7_7_3 | ASPH | aspartate beta-hydroxylase (ASPH) | 2.14 | 5.18 | 1.24E−05 | 3.41E−04 | 6 |
| 8_9_17 | STK17B | Serine/threonine-protein kinase 17B | 2.14 | 6.13 | 8.14E−07 | 2.86E−04 | 7 |
| 23_17_21 | KRT8 | keratin 8 (KRT8) | 2.14 | 5.37 | 7.18E−06 | 3.22E−04 | 5 |
| 38_17_13 | ACTN4 | actinin, alpha 4 (ACTN4) | 2.12 | 4.41 | 1.13E−04 | 6.46E−04 | 5 |
| 31_9_21 | VPS35 | vacuolar protein sorting 35 homolog (*S. cerevisiae*) (VPS35) | 2 12 | 5.77 | 2.31E−06 | 2.88E−04 | 4 |
| 3_18_19 | UBL3 | Ubiquitin-like protein 3 | 2.11 | 4.94 | 2.52E−05 | 3.74E−04 | 4 |
| 40_14_9 | ACPP | acid phosphatase, prostate (ACPP) | 2.11 | 6.30 | 4.99E−07 | 2.57E−04 | 3 |
| 11_2_11 | CSRP3 | cysteine and glycine-rich protein 3 (cardiac LIM protein) (CSRP3) | 2.10 | 3.32 | 2.31E−03 | 4.51E−03 | 7 |
| 32_14_7 | ACP6 | acid phosphatase 6, lysophosphatidic (ACP6) | 2.09 | 4.87 | 3.08E−05 | 3.86E−04 | 4 |

TABLE 1B

Top 30 WK 10 up-regulated antibody targets (ACPP is noted in bold). Refer to Table 1A for column definitions.

| Array Spot ID | Gene Symbol | Gene Name | Fold Change | T stat | P Value | Adj. P Value | Num Samples Exp. |
|---|---|---|---|---|---|---|---|
| 31_15_3 | LGALS3 | lectin, galactoside-binding, soluble, 3 (LGALS3) | 4.95 | 9.28 | 2.84E−10 | 2.05E−06 | 17 |
| 25_19_13 | CACNG1 | calcium channel, voltage-dependent, gamma subunit 1 (CACNG1) | 4.83 | 6.51 | 3.60E−07 | 2.69E−04 | 10 |
| 24_9_15 | ANPEP | alanyl (membrane) aminopeptidase (aminopeptidase N, aminopeptidase M, microsomal aminopeptidase, CD13, p150) (ANPEP) | 4.73 | 7.19 | 5.69E−08 | 6.85E−05 | 8 |
| 25_19_1 | LGALS3 | Galectin-3 | 4.13 | 8.59 | 1.54E−09 | 5.57E−06 | 16 |
| 19_14_15 | FBXO6 | F-box protein 6 (FBXO6) | 3.88 | 7.67 | 1.62E−08 | 2.68E−05 | 11 |
| 41_8_17 | ECE1 | endothelin converting enzyme 1 (ECE1) | 3.42 | 5.66 | 3.73E−06 | 3.26E−04 | 11 |
| 16_17_9 | FBXO21 | F-box protein 21 (FBXO21) | 3.34 | 4.96 | 2.68E−05 | 4.97E−04 | 8 |
| 4_17_13 | LGALS3 | lectin, galactoside-binding, soluble, 3 (LGALS3) | 3.24 | 8.23 | 3.83E−09 | 9.23E−06 | 13 |
| 28_2_15 | VPS35 | vacuolar protein sorting 35 homolog (*S. cerevisiae*) (VPS35) | 3.12 | 5.26 | 1.15E−05 | 3.65E−04 | 7 |

TABLE 1B-continued

Top 30 WK 10 up-regulated antibody targets (ACPP is noted in bold). Refer to Table 1A for column definitions.

| Array Spot ID | Gene Symbol | Gene Name | Fold Change | T stat | P Value | Adj. P Value | Num Samples Exp. |
|---|---|---|---|---|---|---|---|
| 37_8_11 | FNDC3A | fibronectin type III domain containing 3A (FNDC3A), transcript variant 2 | 2.91 | 5.55 | 5.18E−06 | 3.27E−04 | 12 |
| 19_12_1 | SAAL1 | serum amyloid A-like 1 (SAAL1) | 2.87 | 4.73 | 5.08E−05 | 6.23E−04 | 8 |
| 3_15_3 | DMRTB1 | Doublesex- and mab-3-related transcription factor B1 | 2.82 | 4.79 | 4.30E−05 | 5.80E−04 | 8 |
| 8_9_17 | STK17B | Serine/threonine-protein kinase 17B | 2.79 | 6.03 | 1.36E−06 | 3.21E−04 | 11 |
| 28_9_15 | PANK4 | pantothenate kinase 4 (PANK4) | 2.79 | 5.02 | 2.30E−05 | 4.66E−04 | 9 |
| 4_3_19 | SGTA | small glutamine-rich tetratricopeptide repeat (TPR)-containing, alpha (SGTA) | 2.76 | 4.57 | 8.05E−05 | 7.76E−04 | 3 |
| 21_21_1 | CSF1 | colony stimulating factor 1 (macrophage) (CSF1), transcript variant 1 | 2.72 | 6.00 | 1.48E−06 | 3.21E−04 | 7 |
| 26_6_21 | ERAS | ES cell expressed Ras (ERAS) | 2.72 | 5.63 | 4.16E−06 | 3.26E−04 | 9 |
| 40_2_15 | PHF20L1 | PHD finger protein 20-like 1 (PHF20L1) | 2.71 | 4.98 | 2.54E−05 | 4.91E−04 | 7 |
| 25_3_17 | TSPAN13 | tetraspanin 13 (TSPAN13) | 2.66 | 5.94 | 1.73E−06 | 3.26E−04 | 8 |
| 48_8_7 | C7orf27 | chromosome 7 open reading frame 27 (C7orf27) | 2.65 | 3.57 | 0.001232 | 4.05E−03 | 7 |
| 34_18_1 | HINT3 | histidine triad nucleotide binding protein 3 (HINT3), mRNA | 2.59 | 6.03 | 1.34E−06 | 3.21E−04 | 8 |
| 24_3_21 | CROP | cisplatin resistance-associated overexpressed protein (CROP) | 2.56 | 4.30 | 0.000169 | 1.15E−03 | 7 |
| 26_5_5 | KYNU | kynureninase (L-kynurenine hydrolase) (KYNU) | 2.55 | 5.63 | 4.15E−06 | 3.26E−04 | 8 |
| 40_14_9 | ACPP | acid phosphatase, prostate (ACPP) | 2.55 | 6.08 | 1.18E−06 | 3.15E−04 | 6 |
| 25_9_15 | DEXI | dexamethasone-induced transcript (DEXI) | 2.52 | 5.88 | 2.04E−06 | 3.26E−04 | 9 |
| 2_6_7 | C11orf48 | Uncharacterized protein C11orf48 | 2.50 | 5.33 | 9.44E−06 | 3.58E−04 | 7 |
| 22_6_7 | ATPBD1B | ATP binding domain 1 family, member B (ATPBD1B) | 2.50 | 4.94 | 2.87E−05 | 5.09E−04 | 8 |
| 15_2_21 | FOXP4 | forkhead box P4 (FOXP4) | 2.50 | 4.29 | 0.000175 | 1.17E−03 | 10 |
| 31_9_21 | VPS35 | vacuolar protein sorting 35 homolog (S. cerevisiae) (VPS35) | 2.49 | 5.55 | 5.20E−06 | 3.27E−04 | 6 |

TABLE 1C

Top 30 WK 22 up-regulated antibody targets (ACPP is noted in bold). Refer to Table 1A for column definitions.

| Array Spot ID | Gene Symbol | Gene Name | Fold Change | T stat | P Value | Adj. P Value | Num Samples Exp. |
|---|---|---|---|---|---|---|---|
| 31_15_3 | LGALS3 | lectin, galactoside-binding, soluble, 3 (LGALS3) | 4.16 | 8.33 | 2.65E−09 | 9.57E−06 | 15 |
| 25_19_1 | LGALS3 | Galectin-3 | 4.13 | 8.62 | 1.27E−09 | 9.20E−06 | 16 |
| 25_19_13 | CACNG1 | calcium channel, voltage-dependent, gamma subunit 1 (CACNG1) | 3.64 | 5.43 | 6.81E−06 | 5.89E−03 | 8 |
| 24_9_15 | ANPEP | alanyl (membrane) aminopeptidase (aminopeptidase N, aminopeptidase M, microsomal aminopeptidase, CD13, p150) (ANPEP) | 3.44 | 5.56 | 4.74E−06 | 4.89E−03 | 6 |
| 19_14_15 | FBXO6 | F-box protein 6 (FBXO6) | 3.24 | 6.75 | 1.75E−07 | 3.16E−04 | 9 |
| 4_17_13 | LGALS3 | lectin, galactoside-binding, soluble, 3 (LGALS3) | 2.91 | 7.30 | 3.91E−08 | 9.40E−05 | 11 |
| 41_8_17 | ECE1 | endothelin converting enzyme 1 (ECE1) | 2.59 | 4.79 | 4.23E−05 | 1.09E−02 | 8 |
| 19_12_1 | SAAL1 | serum amyloid A-like 1 (SAAL1) | 2.41 | 4.23 | 2.01E−04 | 1.42E−02 | 5 |
| 16_17_9 | FBXO21 | F-box protein 21 (FBXO21) | 2.39 | 4.21 | 2.10E−04 | 1.43E−02 | 5 |

TABLE 1C-continued

Top 30 WK 22 up-regulated antibody targets (ACPP is noted
in bold). Refer to Table 1A for column definitions.

| Array Spot ID | Gene Symbol | Gene Name | Fold Change | T stat | P Value | Adj. P Value | Num Samples Exp. |
|---|---|---|---|---|---|---|---|
| 21_21_1 | CSF1 | colony stimulating factor 1 (macrophage) (CSF1), transcript variant 1 | 2.33 | 5.04 | 2.05E−05 | 7.81E−03 | 5 |
| 35_8_21 | GDPD5 | glycerophosphodiester phosphodiesterase domain containing 5 (GDPD5) | 2.29 | 4.34 | 1.47E−04 | 1.40E−02 | 5 |
| 34_18_1 | HINT3 | histidine triad nucleotide binding protein 3 (HINT3), mRNA | 2.17 | 5.17 | 1.44E−05 | 7.78E−03 | 5 |
| 37_8_11 | FNDC3A | fibronectin type III domain containing 3A (FNDC3A), transcript variant 2 | 2.14 | 3.86 | 5.55E−04 | 1.66E−02 | 9 |
| 37_7_13 | MED1 | Mediator of RNA polymerase II transcription subunit 1 | 2.11 | 4.43 | 1.17E−04 | 1.32E−02 | 3 |
| 40_2_15 | PHF20L1 | PHD finger protein 20-like 1 (PHF20L1) | 2.10 | 4.27 | 1.82E−04 | 1.42E−02 | 5 |
| 28_2_15 | VPS35 | vacuolar protein sorting 35 homolog (S. cerevisiae) (VPS35) | 2.10 | 4.77 | 4.40E−05 | 1.09E−02 | 3 |
| 17_5_5 | MGC40405 | family with sequence similarity 133, member B (FAM133B), transcript variant 1 | 2.10 | 2.49 | 1.85E−02 | 6.82E−02 | 3 |
| 22_7_19 | SPAG6 | sperm associated antigen 6 (SPAG6), transcript variant 1 | 2.04 | 3.44 | 1.75E−03 | 2.26E−02 | 3 |
| 25_3_17 | TSPAN13 | tetraspanin 13 (TSPAN13) | 2.01 | 4.44 | 1.11E−04 | 1.32E−02 | 5 |
| 24_3_21 | CROP | cisplatin resistance-associated overexpressed protein (CROP) | 2.00 | 4.28 | 1.77E−04 | 1.42E−02 | 4 |
| 25_9_15 | DEXI | dexamethasone-induced transcript (DEXI) | 1.97 | 4.26 | 1.85E−04 | 1.42E−02 | 5 |
| 47_7_1 | WDFY1 | WD repeat and FYVE domain containing 1 (WDFY1) | 1.96 | 5.13 | 1.62E−05 | 7.78E−03 | 4 |
| 22_6_7 | ATPBD1B | ATP binding domain 1 family, member B (ATPBD1B) | 1.96 | 4.04 | 3.39E−04 | 1.45E−02 | 4 |
| 26_6_21 | ERAS | ES cell expressed Ras (ERAS) | 1.95 | 4.30 | 1.64E−04 | 1.42E−02 | 5 |
| 30_19_19 | KRAS | v-Ki-ras2 Kirsten rat sarcoma viral oncogene homolog (KRAS), transcript variant b, mRNA. | 1.94 | 5.95 | 1.60E−06 | 1.92E−03 | 5 |
| 29_9_5 | CMTM3 | CKLF-like MARVEL transmembrane domain containing 3 (CMTM3), transcript variant 4 | 1.94 | 4.04 | 3.38E−04 | 1.45E−02 | 4 |
| 40_14_9 | ACPP | acid phosphatase, prostate (ACPP) | 1.93 | 5.08 | 1.83E−05 | 7.78E−03 | 5 |
| 27_9_1 | C12orf10 | chromosome 12 open reading frame 10 (C12orf10) | 1.92 | 6.27 | 6.59E−07 | 9.52E−04 | 3 |
| 9_4_17 | STRA13 | stimulated by retinoic acid 13 homolog (mouse) (STRA13) | 1.92 | 3.04 | 4.88E−03 | 3.53E−02 | 5 |

The top targets were not amongst the known family of cancer/testes antigens (Scanlan, et al., 2004) (such as NY-ESO-1, or the MAGE, GAGE, PAGE LAGE families). There may be several reasons for this observation. As noted earlier, studies of auto-antibody responses induced by standard (hormone and radiation (Nesslinger, et al., 2007)) as well as immune-therapies (Nesslinger, et al., 2010; Kwek, et al., 2012; Nguyen, et al., 2010) have shown that immune responses induced post-therapy may be against targets not previously characterized in the literature as cancer antigens. Additionally, most of the well-known cancer/testis antigens were discovered using cDNA libraries and serum samples from cancer patients and not post-treatment settings. It is likely that in therapeutic settings immune responses to novel antigens, not generally identified by screening of cancer patients, are developed. Responses following therapy may develop in the context of increased tumor cell death in an enhanced inflammatory state induced by the treatment, which induce responses to auto-antigens that are typically recognized as self.

Note that of the three most commonly referenced prostate antigens, namely PSA, PSMA and PSCA, PSMA and PSA were not present on the ProtoArray. PSCA was present, but antibodies against PSCA were not significantly up-regulated post-sipuleucel-T treatment.

E. Enrichment of Post-Sipuleucel-T Treatment Antibody Targets within Cancer Signaling Pathways Enrichment for antibodies generated against targets in cancer-related signaling pathways after sipuleucel-T treatment was detected. Such enrichment supports the hypothesis of tumor tissue destruction and priming of immune responses against cancer antigens post-treatment. The KEGG (Kanehisa, et al., 2012) and Ingenuity (IPA) knowledge bases (www.ingenuity.com/products/pathways_analysis.html; www.ingenuity.com/science/knowledge_base.html) were used to examine the enrichment of genes or targets in cancer-related pathways within the top 10% (~720 targets by fold-change, with FDR≤10%) of the up-regulated antibody targets post-treatment. Enrichment was determined empirically (for KEGG pathways, 10,000 bootstrap samplings) or using the Fisher exact test (for pathways in the Ingenuity knowledge base). For the Fisher exact test the background set (or sampling 'universe') was all the genes in the IPA knowledge base that intersected with the target set represented on the ProtoArray platform.

The WK10 antibody targets were enriched for genes in KEGG Prostate Cancer pathway (empirical p-value 0.003, based on 10,000 samplings of random target lists of similar size as the top 10% list, i.e., ~720, from the ProtoArray), KEGG VEGF signaling pathway (empirical p-value 0.005) and KEGG mTOR signaling pathway (empirical p-value 0.006) pathways. VEGF activity known to be associated with prostate cancer growth and osteoblastic bone metastasis (Aragon-Ching J B, et al. 2010; Dai J, et al. 2004). PI3K/Akt/mTOR signaling is up-regulated in 30-50% of prostate cancers, often through loss of PTEN and is associated with increasing tumor stage, grade, and risk of biochemical recurrence (Morgan, et al., 2009).

F. Sipuleucel-T Induced Antibody Targets Show Enrichment Against Prostate Tumor Over-Expressed Genes Genes reported as over-expressed in prostate tumors in the largest reported study of gene expression in prostate tumor and normal tissues (Ribas et al., 2009; Fox et al., 2011) were examined to determine whether reactive IgGs to the antigens encoded by such genes were enriched at week 10. Genes that were over-expressed in at least 33% of prostate tumors (primary and metastatic combined) relative to normal prostate tissues were considered, which gave a list of 678 genes. Of these 678 genes, 152 were represented as protein products on the ProtoArray. The overlap of these 152 proteins with the antigens against which serum IgG levels had increased from pre-treatment levels at week 10 in IMPACT was evaluated. The targets of the 100 and 50 most highly induced IgGs overlapped significantly with these 152 products; 6 targets of the top 100 (p=0.012, hypergeometric test) and 4 targets of the top 50 (p=0.013) overlapped with the 152 products of genes over-expressed in prostate tumors.

Figure 2:
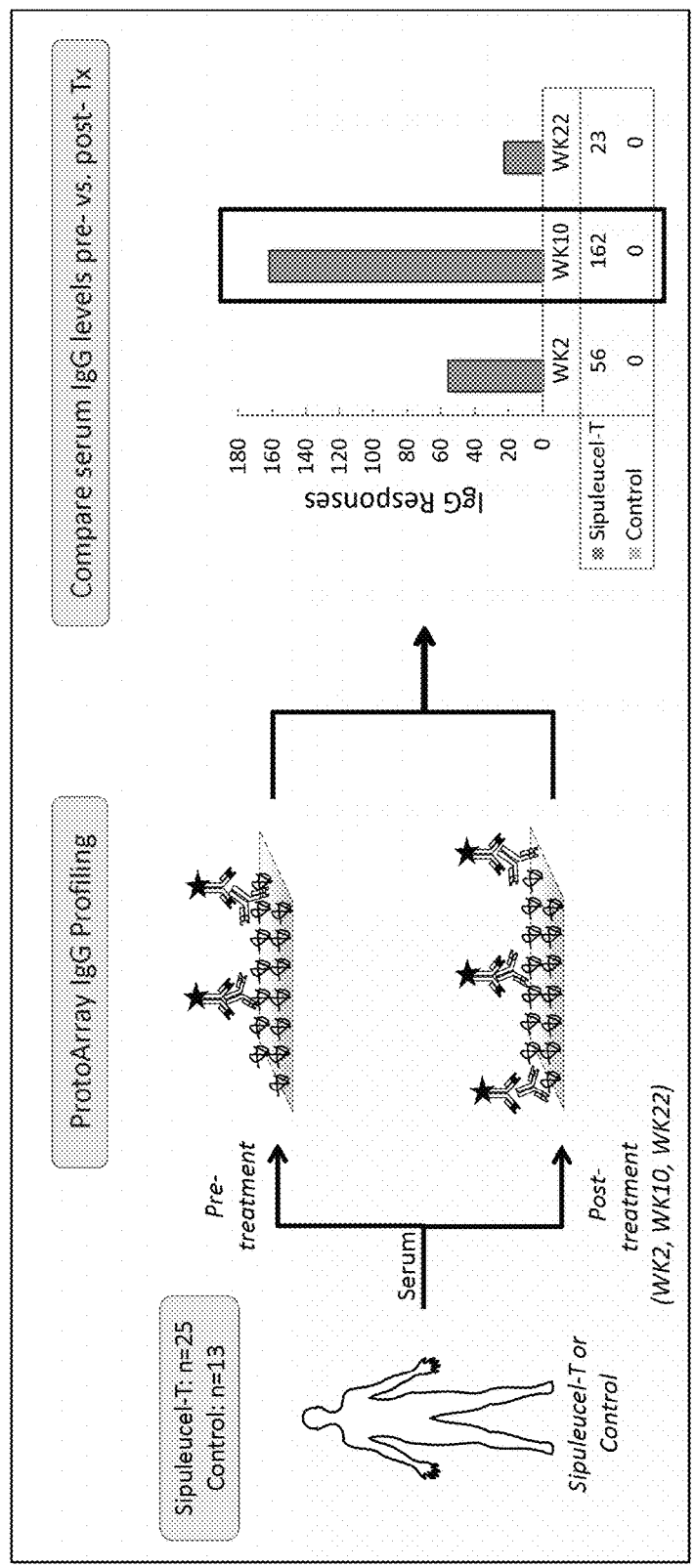
FIG. 2: Schematic for identification of serum IgG responses to secondary antigens in IMPACT, using ProtoArray. IgG levels in pre- and post-treatment serum samples were compared to identify IgG responses against specific proteins (antigens) on the ProtoArray (≥2-fold average increase in serum IgG level post-treatment relative to pre-treatment, with FDR≤10%). The number of antigens against which IgG responses were observed (y-axis) at the three post-treatment time points, namely Wk-2, Wk-10, and Wk-22/PPFU, (x-axis) are shown for patients in the sipuleucel-T and control arms.

Example 3: Validation of Antibody Responses Against Self-Antigens Observed Post-Sipuleucel-T Treatment A. Background In Example 2, the ProtoArray platform was used to broadly evaluate the elevation of IgG levels against self-antigens post-treatment with sipuleucel-T as depicted in FIG. 2. The results showed that antibody responses post-treatment may target proteins involved in the prostate cancer signaling pathways. This Example evaluates several of the antibody targets identified using the ProtoArray platform using an independent platform.

B. Confirmation of Serum IgG Responses to Secondary Antigens with Luminex xMAP

IgG responses to a subset of the secondary antigens identified using ProtoArray were confirmed using an independent analytical platform, Luminex xMAP (Pickering, et al., 2002). We chose Luminex xMAP because of its low sample volume requirements, high reported sensitivity, wide linear range, and capability for multiplex IgG detection. From the 162 secondary antigens to which IgG responses were observed at week 10 with ProtoArray, ten were selected for confirmation (Table 2).

TABLE 2

Non-target Antigen Candidates Identified in Patients from IMPACT using ProtoArray.

| | ProtoArray Data | | | |
|---|---|---|---|---|
| Antigen Symbol | Average Fold-Change | P-value | FDR (%) | Rank by Average Fold-Change |
| LGALS3 | 4.94 | 2.84E−10 | 2.05E−04 | 1 |
| CACNG1 | 4.83 | 3.60E−07 | 2.69E−02 | 2 |
| ANPEP | 4.73 | 5.69E−08 | 6.85E−03 | 3 |
| FBXO6 | 3.88 | 1.62E−08 | 2.68E−03 | 4 |
| ECE1 | 3.42 | 3.73E−06 | 3.26E−02 | 5 |
| ERAS | 2.72 | 4.16E−06 | 3.26E−02 | 15 |
| TSPAN13 | 2.66 | 1.73E−06 | 3.26E−02 | 17 |
| PAP | 2.55 | 1.18E−06 | 3.15E−02 | 23 |
| LGALS8/PCTA-1 | 2.19 | 2.89E−05 | 5.09E−02 | 68 |
| KRAS | 2.10 | 3.20E−06 | 3.26E−02 | 99 |
| KLK2/hK2 | 2.04 | 3.67E−05 | 5.50E−02 | 138 |

FDR, False discovery rate

Of these ten antigens, five corresponded to the IgGs that exhibited the highest-fold increases in level post-treatment (LGALS3, ANPEP, ECE1, FBXO6 and CACNG1); LGALS3 (Newlaczyl, et al., 2011; Califice, et al., 2004; Laderach, et al., 2013), ANPEP (Fukusawa, et al., 2006; Larkin, et al., 2012; Sorensen, et al., 2013), ECE1 (Lambert, et al., 2008; Herrmann, et al., 2006; Nelson, et al., 1995; Nelson, et al., 2005) are known to be expressed at high levels in prostate tumors or to have functional roles in prostate cancer development. We selected the remaining five antigens based on reported functional relevance in cancer and/or increased expression in prostate tumors; viz., KLK2 (Darson, et al., 1999; Williams, et al., 2010; Rittenhouse, et al., 1998), ERAS (Kubota, et al., 2010), KRAS (Taylor, et al., 2010), TSPAN13 (Arencibia, et al., 2009), and LGALS8 (Laderach, et al., 2013; Su, et al., 1996). ProtoArray data showed that levels of IgGs to most of these ten candidate secondary antigens were also elevated at the earlier (week 2) and later (week 22) timepoints (Table 3).

TABLE 3

Increase in levels of IgG against candidate antigens at weeks 2 and 22 in IMPACT as measured with ProtoArray.

| | Week 2 | | | | Week 22 | | | |
|---|---|---|---|---|---|---|---|---|
| Antigen | Average Fold-Change | P-value | FDR (%) | Rank By Fold-Change | Average Fold-Change | P-value | FDR (%) | Rank By Fold-Change |
| LGALS3 | 3.03 | 7.73E−08 | 0.019 | 3 | 4.16 | 2.65E−09 | 0.001 | 1 |
| CACNG1 | 3.30 | 2.07E−06 | 0.029 | 2 | 3.64 | 6.81E−06 | 0.589 | 2 |
| ANPEP | 3.31 | 4.04E−07 | 0.025 | 1 | 3.44 | 4.74E−06 | 0.489 | 3 |
| FBXO6 | 2.56 | 4.18E−07 | 0.025 | 7 | 3.24 | 1.75E−07 | 0.032 | 4 |
| ECE1 | 2.64 | 2.07E−05 | 0.037 | 6 | 2.59 | 4.23E−05 | 1.087 | 5 |
| ERAS | 2.07 | 1.51E−05 | 0.035 | 41 | 1.95 | 1.64E−04 | 1.424 | 34 |
| TSPAN13 | 1.86 | 4.77E−04 | 0.149 | 135 | 2.01 | 1.11E−04 | 1.317 | 22 |

TABLE 3-continued

Increase in levels of IgG against candidate antigens at
weeks 2 and 22 in IMPACT as measured with ProtoArray.

| | Week 2 | | | | Week 22 | | | |
|---|---|---|---|---|---|---|---|---|
| Antigen | Average Fold-Change | P-value | FDR (%) | Rank By Fold-Change | Average Fold-Change | P-value | FDR (%) | Rank By Fold-Change |
| PAP | 2.11 | 4.99E−07 | 0.026 | 30 | 1.93 | 1.83E−05 | 0.778 | 37 |
| LGALS8 | 1.69 | 2.17E−04 | 0.091 | 374 | 1.78 | 6.86E−04 | 1.723 | 78 |
| KRAS | 1.90 | 6.29E−06 | 0.032 | 99 | 1.94 | 1.60E−06 | 0.192 | 35 |
| KLK2 | 2.20 | 1.68E−06 | 0.029 | 19 | 1.49 | 1.23E−03 | 2.006 | 487 |

Fold-change, ratio of serum IgG level at timepoint and at pre-treatment; FDR, False discovery rate.

Antigens were selected from the ProtoArray data (Example 2) based on the following criteria:

i. In a comparison of patients from sipuleucel-T and control arms, higher fold-change in IgG level post-treatment with sipuleucel-T (n=93) than with control (n=39), with p≤0.01 for the comparison.

ii. In sipuleucel-T-treated patients (n=93), a significant increase in IgG levels after treatment compared to pre-treatment (p≤0.01) and ≥10% of patients demonstrating an IgG response (defined as ≥2-fold increase in IgG level post-treatment compared to pre-treatment).

Figure 3A:
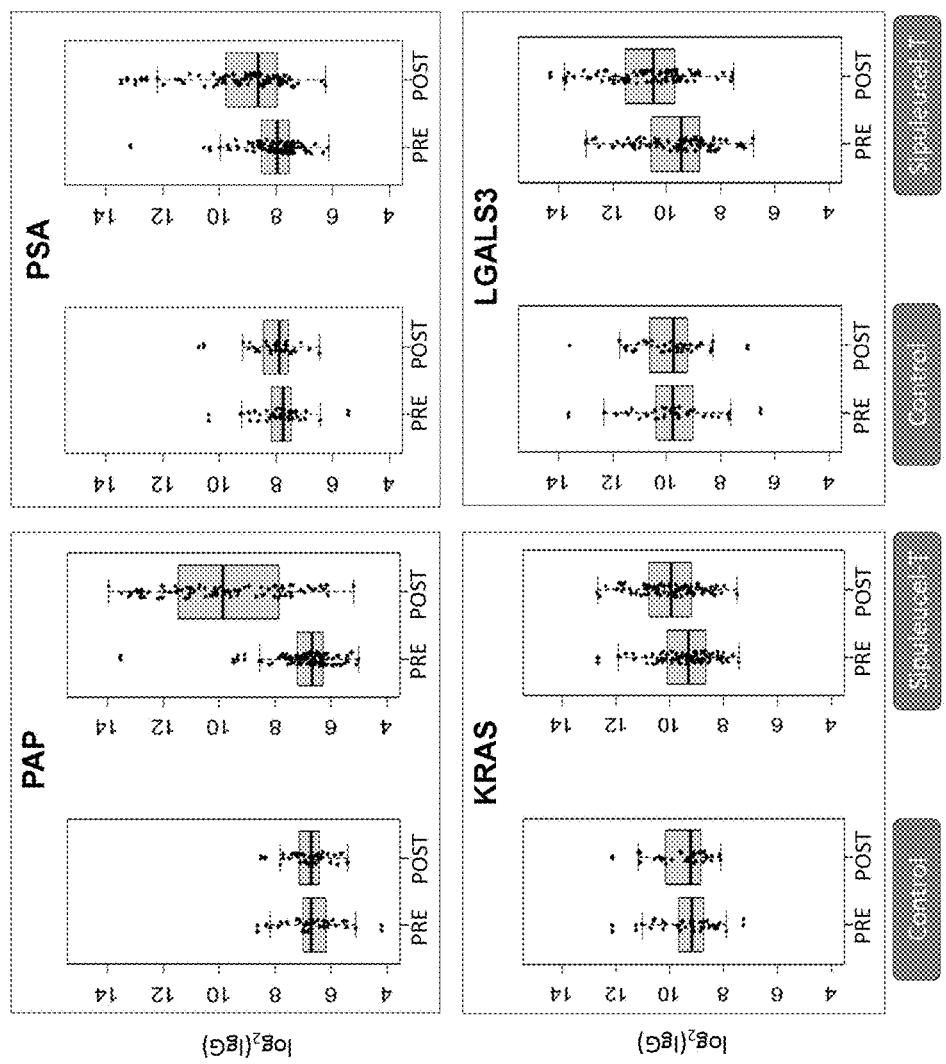
FIG. 3: Confirmation of serum IgG responses to secondary antigens in patients from IMPACT using Luminex xMAP, and analyses of overlaps between IgG responders. (A) Confirmation of IgG responses in IMPACT, 10 weeks after treatment, using Luminex xMAP. $Log_e$ of serum IgG levels (y-axes) pre- and post-treatment in the control and sipuleucel-T arms are shown. Data for three secondary antigens (PSA, KRAS, and LGALS3) are shown. Serum levels of IgG against PAP (primary antigen) are shown for reference. See Table 4 for details. (B) Overlap of IgG responses to different antigens in patients from the sipuleucel-T arm shown using Venn diagrams. The numbers of patients with overlapping IgG responses to different antigens at week 10 are shown. Left: Overlaps include IgG responses to PAP (primary antigen); Right: Overlaps include IgG responses to secondary antigens only. IgG responders are defined as patients with ≥2-fold increase in serum IgG level post-treatment vs. pre-treatment. Representative examples are shown here.

Sipuleucel-T-induced increases in levels of IgGs to the following antigens were confirmed by Luminex xMAP: PSA, KLK2, KRAS, ERAS, LGALS8 and LGALS3 (Table 4 and FIG. 3).

TABLE 4

Confirmation of serum IgG responses to candidate secondary
antigens at week 10 in IMPACT, using Luminex xMAP.

| Antigens Tested | | Sipuleucel-T (n = 93) | | | Control (n = 39) | | | Sipuleucel-T vs Control |
|---|---|---|---|---|---|---|---|---|
| Selection Source | Name or Symbol | P-value (pre vs post) | Patients with ≥2-fold up-reg (%) | Patients with ≥5-fold up-reg (%) | P-value (pre vs post) | Patients with ≥2-fold up-reg (%) | Patients with ≥5-fold up-reg (%) | P-value (fold-change) |
| Controls | PAP | 8.46E−16 | 69 (74.2) | 55 (59.1) | 0.107 | 4 (10.3) | 0 (0) | 2.38E−12 |
| | PA2024 | 2.83E−17 | 86 (92.5) | 75 (80.6) | 0.256 | 10 (25.6) | 2 (5.1) | 4.81E−17 |
| | Tetanus Toxoid | 5.71E−05 | 10 (10.8) | 0 (0) | 0.100 | 6 (15.4) | 1 (2.6) | 1.93E−01 |
| Known PCa antigens | PSA | 1.42E−10 | 36 (38.7) | 13 (14) | 0.066 | 5 (12.8) | 1 (2.6) | 2.15E−04 |
| | PSMA | 1.48E−05 | 18 (19.4) | 4 (4.3) | 0.293 | 4 (10.3) | 2 (5.1) | 2.48E−02 |
| Proto Array Candidates | LGALS3 | 2.83E−10 | 26 (28) | 3 (3.2) | 0.152 | 4 (10.3) | 2 (5.1) | 4.72E−04 |
| | CACNG1 | 4.23E−04 | 9 (9.7) | 3 (3.2) | 0.425 | 2 (5.1) | 0 (0) | 3.07E−02 |
| | ANPEP | 8.14E−06 | 6 (6.5) | 1 (1.1) | 0.753 | 1 (2.6) | 0 (0) | 7.06E−04 |
| | FBXO6 | 4.69E−03 | 12 (12.9) | 4 (4.3) | 0.846 | 1 (2.6) | 0 (0) | 1.36E−02 |
| | ECE1 | 2.22E−04 | 25 (26.9) | 6 (6.5) | 0.302 | 4 (10.3) | 3 (7.7) | 5.22E−02 |
| | ERAS | 2.97E−10 | 39 (41.9) | 11 (11.8) | 0.148 | 5 (12.8) | 2 (5.1) | 1.92E−04 |
| | TSPAN13 | 1.41E−02 | 11 (11.8) | 4 (4.3) | 0.779 | 2 (5.1) | 0 (0) | 4.74E−02 |
| | LGALS8 | 3.57E−11 | 23 (24.7) | 5 (5.4) | 0.034 | 3 (7.7) | 0 (0) | 3.06E−04 |
| | KRAS | 1.82E−10 | 37 (39.8) | 14 (15.1) | 0.208 | 5 (12.8) | 0 (0) | 4.71E−05 |
| | KLK2 | 1.73E−09 | 41 (44.1) | 9 (9.7) | 0.079 | 5 (12.8) | 1 (2.6) | 3.94E−04 |

PCa, Prostate cancer

As expected, increases in levels of IgGs to PAP and PA2024 were also confirmed. IgG responses to several antigens, e.g., PSA, KLK2, KRAS, ERAS, and LGALS3, were observed in ≥25% (range: 28-44%) of the sipuleucel-T-treated patients from IMPACT. A 5-fold increase in anti-PSA, anti-KRAS, or anti-ERAS IgG level was observed in ≥10% (range: 12-15%) of sipuleucel-T-treated patients. Levels of IgGs to these antigens were not significantly elevated after treatment in the control patients (p>0.01, Table 4).

To determine if the IgG responses to secondary antigens observed at the week 10 timepoint in IMPACT also occurred at other timepoints, serum samples from the other available post-treatment timepoints in IMPACT (weeks 2 and 22) were examined (see Tables 5A and 5B).

TABLE 5A

Evaluation of IgG responses against candidate antigens at week 2 in IMPACT using Luminex xMAP.

| | | Week 2 | | | | | | |
|---|---|---|---|---|---|---|---|---|
| | | Sip-T (n = 142) | | | Control (n = 62) | | | Sip-T vs Control |
| Antigen | | P-value | n (%) | n (%) | P-value | n (%) | n (%) | P-value |
| Selection Source | Symbol or Name | (pre vs post) | ≥2-fold up-reg | ≥5-fold up-reg | (pre vs post) | ≥2-fold up-reg | ≥5-fold up-reg | (fold-change, Sip-T vs Control) |
| Controls | PAP | 3.59E−22 | 92 (64.8) | 65 (45.8) | 0.5 | 0 (0) | 0 (0) | 4.05E−19 |
| | PA2024 | 4.82E−25 | 119 (83.8) | 103 (72.5) | 0.559 | 3 (4.8) | 1 (1.6) | 8.97E−25 |
| | Tetanus Toxoid | 2.77E−15 | 23 (16.2) | 1 (0.7) | 0.287 | 1 (1.6) | 0 (0) | 6.80E−07 |
| Known PCa antigen | PSA | 6.58E−16 | 35 (24.6) | 21 (14.8) | 0.428 | 0 (0) | 0 (0) | 2.97E−09 |
| ProtoArray Candidates | LGALS3 | 1.71E−15 | 41 (28.9) | 13 (9.2) | 0.572 | 3 (4.8) | 0 (0) | 3.68E−09 |
| | ERAS | 1.39E−16 | 60 (42.3) | 25 (17.6) | 0.761 | 3 (4.8) | 0 (0) | 6.62E−11 |
| | LGALS8 | 8.43E−17 | 36 (25.4) | 17 (12) | 0.002 | 2 (3.2) | 0 (0) | 1.29E−05 |
| | KRAS | 1.20E−18 | 57 (40.1) | 22 (15.5) | 0.819 | 1 (1.6) | 0 (0) | 3.90E−13 |
| | KLK2 | 6.37E−16 | 52 (36.6) | 18 (12.7) | 0.724 | 2 (3.2) | 1 (1.6) | 8.07E−10 |

PCa, prostate cancer.

TABLE 5B

Evaluation of IgG responses against candidate antigens at week 22 in IMPACT using Luminex xMAP.

| | | Week 22 | | | | | | |
|---|---|---|---|---|---|---|---|---|
| | | Sip-T (n = 60) | | | Control (n = 16) | | | Sip-T vs Control |
| Antigen | | P-value | n (%) | n (%) | P-value | n (%) | n (%) | P-value |
| Selection Source | Symbol or Name | (pre vs post) | ≥2-fold up-reg | ≥5-fold up-reg | (pre vs post) | ≥2-fold up-reg | ≥5-fold up-reg | (fold-change, Sip-T vs Control) |
| Controls | PAP | 4.19E−09 | 35 (58.3) | 23 (38.3) | 0.029 | 3 (18.8) | 0 (0) | 5.41E−04 |
| | PA2024 | 1.18E−10 | 52 (86.7) | 43 (71.7) | 0.088 | 4 (25) | 1 (6.2) | 7.55E−07 |
| | Tetanus Toxoid | 1.07E−02 | 11 (18.3) | 2 (3.3) | 0.281 | 2 (12.5) | 0 (0) | 2.56E−01 |
| Known PCa antigen | PSA | 3.56E−07 | 18 (30) | 8 (13.3) | 0.058 | 1 (6.2) | 0 (0) | 1.86E−02 |
| ProtoArray Candidates | LGALS3 | 1.06E−05 | 8 (13.3) | 1 (1.7) | 0.126 | 1 (6.2) | 0 | 5.08E−02 |
| | ERAS | 2.46E−06 | 23 (38.3) | 6 (10) | 0.096 | 3 (18.8) | 0 (0) | 1.75E−02 |
| | LGALS8 | 2.45E−05 | 13 (21.7) | 1 (1.7) | 0.029 | 0 (0) | 0 (0) | 1.35E−01 |
| | KRAS | 9.71E−07 | 14 (23.3) | 4 (6.7) | 0.106 | 1 (6.2) | 0 (0) | 4.45E−02 |
| | KLK2 | 2.46E−06 | 19 (31.7) | 2 (3.3) | 0.149 | 1 (6.2) | 1 (6.2) | 2.38E−02 |

PCa, prostate cancer.

In IMPACT, significant (p≤0.01) increases in levels of IgGs against PSA, KLK2, KRAS, ERAS, LGALS8 and LGALS3 were observed in the sipuleucel-T group at week 2 (n=142) and week 22 (n=60).

C. Antigen Sourcing and Preparation for Validation Assays

Antigens for validation were obtained from Origene Technologies, Invitrogen and Sino Biological Inc. The list of antigens sourced from each vendor is provided in Table 6, along with the information about the clones used for the protein production and expression cell lines. For the purpose of evaluating the dependence of the assays on the protein expression system or purification tags, several proteins were prepared using multiple expression systems and purification tags (viz., PAP, KRAS, ERAS, KLK2; Table 6).

TABLE 6

Protein reagents used in Luminex xMAP assays.

| Antigen Name or Symbol | Expression System | Protein or Nucleotide ID | Protein Provider | Product Number (if any) | Method of Luminex Conjugation |
|---|---|---|---|---|---|
| PAP | Mammalian (CHO) | P15309 | Dendreon | | Direct |
| PA2024 | Insect (BV/Sf21) | | Dendreon | | Direct |
| Tetanus Toxoid | Inactived Tetanus Toxoid | Tetanus Toxoid from *Clostridium tetani* | List Biological Laboratories, INC | 191B | Direct |

TABLE 6-continued

Protein reagents used in Luminex xMAP assays.

| Antigen Name or Symbol | Expression System | Protein or Nucleotide ID | Protein Provider | Product Number (if any) | Method of Luminex Conjugation |
|---|---|---|---|---|---|
| PSA (KLK3) | Mammalian (HEK293) | P07288 | Sino Biological | 10771-H08H | Direct |
| PSMA | Mammalian (HEK293) | NM_004476 | Origene Technologies | TP318310 | Direct |
| LGALS3 | E. coli | P17931 | Sino Biological | 10289-HNAE | Direct |
| CACNG1 | Mammalian (HEK293 derivative) | NM_000727.2 | LifeTechnologies | NA | GST-Antibody |
| ANPEP | Mammalian (HEK293) | NP_001141.2 | Sino Biological | 10051-H08H | Direct |
| FBXO6 | Mammalian (HEK293 derivative) | NM_018418.2 | LifeTechnologies | NA | GST-Antibody |
| ECE1 | Mammalian (HEK293) | NM_001113349 | Origene Technologies | TP326153 | Direct |
| ERAS | Mammalian (HEK293) | NM_181532.2 | Origene Technologies | TP310965 | Direct |
| TSPAN13 | Mammalian (HEK293 derivative) | NM_014399.2 | LifeTechnologies | NA | GST-Antibody |
| LGALS8 | Mammalian (HEK293) | AAF19370.1 | Sino Biological | 10301-H09E | Direct |
| KRAS | E. coli | AAH13572.1 | Sino Biological | 12259-H07E | Direct |
| KLK2 | Mammalian (HEK293) | NM_005551.3 | Origine Technologies | TP302667 | Direct |

D. Serum Sample Evaluation

For Luminex xMAP assays, pairs of serum samples from the IMPACT clinical study were available from the following patients: (i) pre-treatment and week 2, n=204 (142 sipuleucel-T and 62 control patients); (ii) pre-treatment and week 10, n=132 (93 sipuleucel-T, 39 control); and (iii) pre-treatment and week 22, n=76 (60 sipuleucel-T, 16 control).

E. Assessment of Serum IgG Responses Post-Treatment Using Luminex xMAP®

IgGs levels against candidate antigens were evaluated by Life Technologies Corporation using Luminex xMAP, which uses multiplexed antigen-conjugated, spectrally-distinguishable, fluorescent (Pickering, et al., 2002). All available pre- and post-treatment serum sample pairs from IMPACT patients were evaluated. GST-tagged proteins were conjugated to the beads using an anti-GST antibody bound to the beads, and proteins that were not GST-tagged were directly (covalently) conjugated to the beads. Serum samples (30 mL) were profiled at a 1:200 dilution. A protein signal assay and control assays (negative and positive) were run in parallel with the captured antigens and experimental samples. BSA captured directly to the beads, and GST captured on anti-GST-conjugated beads were used as negative controls. Across the samples evaluated, the median fluorescence intensity of IgGs against BSA was <100 and that against GST was <500, indicating low background signal. Positive controls included anti-human IgG (to indicate the presence of serum in the assayed sample) and human IgG (to indicate the presence of secondary antibody).

All signals from Luminex xMAP were $\log_2$-transformed prior to analyses. A subset of patients' serum samples (n=120) was initially assayed in triplicate to evaluate the technical reproducibility of the platform. Within a batch, the median coefficient of variation (CV) for triplicate samples was low (<5%) for every evaluated antigen. Therefore, the remaining serum samples were assayed in single runs, with controls. To avoid batch effects, the pre- and post-treatment serum samples from patients were run with same lot of antigen-conjugated beads.

F. Overlap Among Serum IgG Responders in the Sipuleucel-T Arm from IMPACT

Figure 3B:
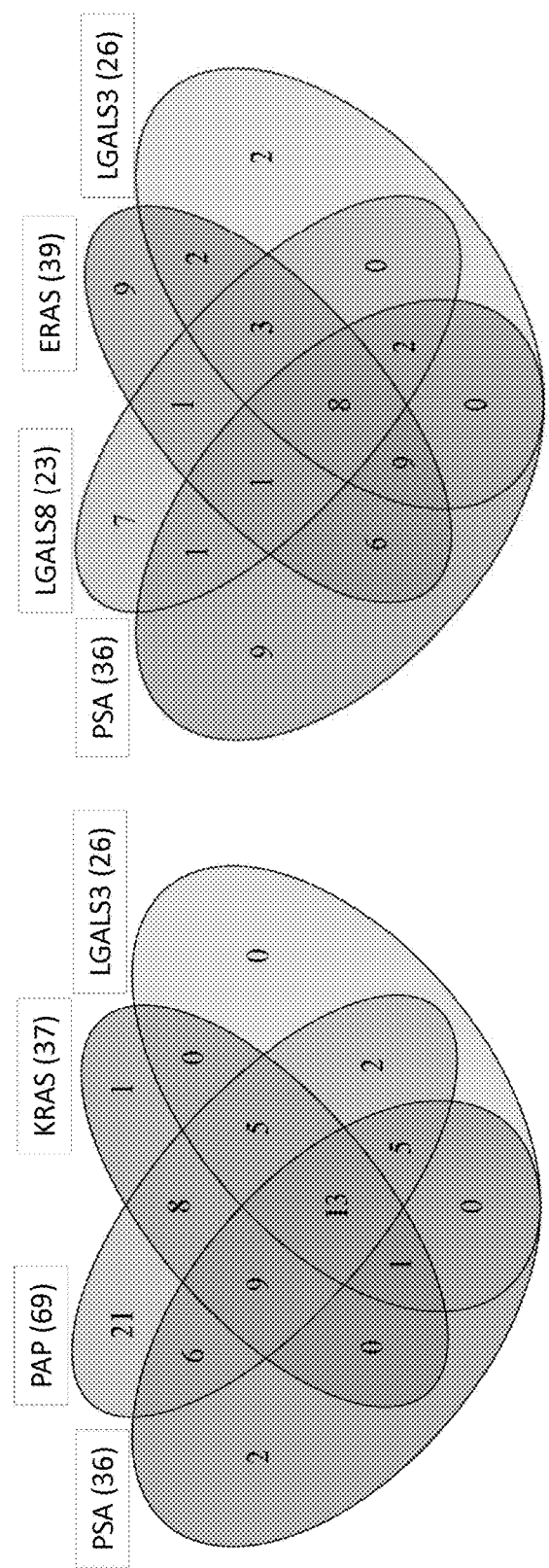

To determine if sipuleucel-T-treated patients shared IgG responses to the same secondary antigens, we evaluated overlaps among IgG responders (see Venn diagrams in FIG. 3B for representative examples, and Table 7 for details). The majority of the sipuleucel-T treated patients who had IgG responses to secondary antigens overlapped with those who had IgG responses to PAP (FIG. 2B, left). Significant overlaps were also observed among IgG responders to a number of different secondary antigens (eg, ERAS and KLK2, or LGALS3 and KRAS, $p \leq 0.01$, hypergeometric test). For example (in FIG. 2B, right), when IgG responses to PSA, ERAS, LGALS8 and LGALS3 were considered, 25% (23/93) of sipuleucel-T-treated patients exhibited responses to three or more of the same antigens, and 9% exhibited responses to all four of these antigens. In this case, depending on the antigen, a minority (<30%) of the IgG responses were unique (ie, did not overlap with IgG responses to other antigens).

TABLE 7

Overlap of the number of patients who were IgG responders to different antigens at week 10 in the sipuleucel-T arm of IMPACT.

| | | PAP (69) | PSA (36) | LGALS3 (26) | ERAS (39) | LGALS8 (23) | KRAS (37) | KLK2 (41) |
|---|---|---|---|---|---|---|---|---|
| | | | | n (p-value) | | | | |
| Antigen (n) | PA2024 (86) | 68 (0.001) | 36 (0.028) | 26 (0.092) | 37 (0.372) | 22 (0.445) | 37 (0.024) | 39 (0.327) |
| | PAP (69) | — | 33 (0.002) | 25 (0.001) | 31 (0.227) | 20 (0.087) | 35 (1.4E−4) | 32 (0.305) |
| | PSA (36) | — | — | 19 (3.26E−05) | 24 (1.0E−4) | 12 (0.101) | 23 (1.8E−4) | 25 (9.6E−05) |
| | LGALS3 (26) | — | — | — | 22 (2.2E−07) | 13 (0.001) | 19 (5.94E−05) | 21 (9.8E−06) |
| | ERAS (39) | — | — | — | — | 13 (0.083) | 21 (0.016) | 37 (5.5E−19) |
| | LGALS8 (23) | — | — | — | — | — | 11 (0.253) | 13 (0.127) |
| | KRAS (37) | — | — | — | — | — | — | 23 (0.004) |

Sipuleucel-T-induced IgG responses were largely consistent across the post-treatment timepoints. Patients from the sipuleucel-T arm in IMPACT with IgG responses to an antigen at week 10 frequently exhibited an IgG response to the same antigen at the earlier (week 2) and later (week 22) timepoints ($p \leq 0.01$, hypergeometric test, Table 8 and 9).

TABLE 8

Overlap of IgG responses across the weeks 2 and 10 post-treatment timepoints.

| Antigens | Wk 2, n | Wk 10, n | Overlap (Wk 2-Wk 10) | P-value |
|---|---|---|---|---|
| PA2024 | 67 | 74 | 63 | 9.54E−02 |
| PAP | 53 | 60 | 46 | 5.23E−04 |
| PSA | 21 | 30 | 17 | 2.33E−06 |
| LGALS3 | 25 | 23 | 13 | 2.35E−03 |
| ERAS | 34 | 35 | 25 | 2.92E−06 |
| LGALS8 | 19 | 17 | 13 | 1.21E−07 |
| KRAS | 32 | 31 | 19 | 1.72E−03 |
| KLK2 | 31 | 36 | 25 | 2.25E−07 |

TABLE 9

Overlap of IgG responses across the weeks 10 and 22 timepoints.

| Antigens | Wk 10, n | Wk 22, n | Overlap (Wk 10-Wk 22) | P-value |
|---|---|---|---|---|
| PA2024 | 47 | 46 | 45 | 2.68E−04 |
| PAP | 37 | 31 | 29 | 2.19E−05 |
| PSA | 24 | 16 | 15 | 3.60E−06 |
| LGALS3 | 17 | 7 | 5 | 3.09E−02 |
| ERAS | 26 | 20 | 17 | 6.86E−05 |
| LGALS8 | 13 | 9 | 9 | 1.94E−07 |
| KRAS | 20 | 13 | 11 | 1.38E−04 |
| KLK2 | 26 | 17 | 14 | 1.27E−03 |

Figure 4:
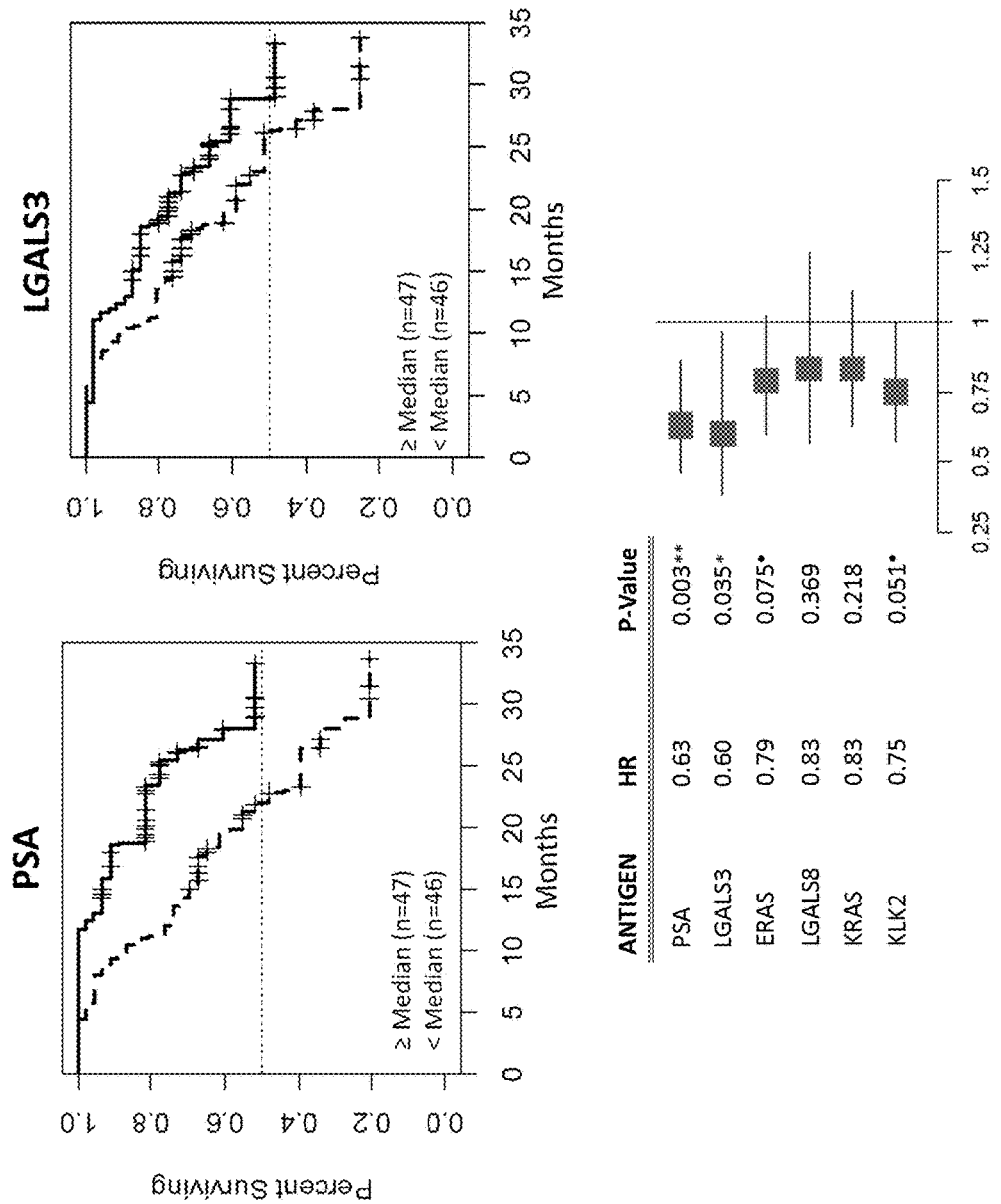
FIG. 4: Association of post-treatment changes in serum levels of IgG ($log_2$) against specified secondary antigens with OS in the sipuleucel-T arm in IMPACT. Kaplan-Meier plots for serum level of IgG to PSA (left) or LGALS3 (right) vs. OS are shown with patients grouped by median fold-change in serum IgG level at week 10 vs. pre-treatment (≥median, solid line, <median, dashed line); the dotted horizontal line indicates estimated median OS. The forest plot below the Kaplan-Meier plots shows HR and 95% CI for the associations of change in serum IgG levels ($log_2$ scale) with OS (adjusted for baseline PSA and LDH) from a multivariate Cox model (See Table 8 for details); boxes in the forest plot indicate HR and whiskers indicate 95% CI. HRs and p-values for each of the IgGs are to the left of the forest plot. p-values are shown to 3 significant digits. ** $p≤0.01$; * $p≤0.05$; • $p≤0.1$.

G. Association of Sipuleucel-T Induced Changes in Serum IgG Levels with OS in IMPACT The association of sipuleucel-T-induced changes in IgG levels at week 10 with OS was evaluated in IMPACT using a multivariate Cox model, adjusted for baseline PSA and LDH levels. Sipuleucel-T-induced changes in levels of anti-PSA IgG (hazard ratio [HR]=0.63, 95% CI 0.46, 0.86; p<0.01) and anti-LGALS3 IgG (HR=0.60, 95% CI 0.38, 0.96; p=0.04) were significantly associated with improved OS (FIG. 4, Table 10). Sipuleucel-T-induced changes in levels of anti-KLK2 IgG and anti-ERAS IgG showed a trend towards association with improved OS (0.05<p<0.1).

TABLE 10

Association of $\log_2$ of fold-change of serum IgG level with OS.

| | Change in IgG Level | | | | | | HR and P-value Multivariate Cox Model | |
|---|---|---|---|---|---|---|---|---|
| | ≥Median | | | <Median | | | | |
| Antigen | n (% of total) | Deaths, n (%) | Median OS (mo) | n (% of total) | Deaths, n (%) | Median OS (mo) | HR (95% CI) | P-value |
| PA2024 | 47-50.54 | 21 (44.68) | 26.3 | 46 (49.46) | 18 (39.13) | 28.04 | 1.07 (0.9-1.28) | 0.446 |
| PAP | 47-50.54 | 16 (34.04) | 26.3 | 46 (49.46) | 23 (50) | 27.12 | 0.94 (0.81-1.1) | 0.442 |
| Tetanus toxoid | 47-50.54 | 21 (44.68) | 27.12 | 46 (49.46) | 18 (39.13) | 26.5 | 0.78 (0.52-1.18) | 0.233 |
| PSA | 47-50.54 | 13 (27.66) | NA | 46 (49.46) | 26 (56.52) | 22.03 | 0.63 (0.46-0.86) | 0.003 |
| LGALS3 | 47-50.54 | 15 (31.91) | 28.9 | 46 (49.46) | 24 (52.17) | 26.3 | 0.6 (0.38-0.96) | 0.035 |
| ERAS | 47-50.54 | 17 (36.17) | 28.9 | 46 (49.46) | 22 (47.83) | 26.3 | 0.79 (0.6-1.02) | 0.075 |
| LGALS8 | 47-50.54 | 19 (40.43) | 26.5 | 46 (49.46) | 20 (43.48) | 27.12 | 0.83 (0.56-1.24) | 0.369 |

TABLE 10-continued

Association of log$_2$ of fold-change of serum IgG level with OS.

| | Change in IgG Level | | | | | | HR and P-value Multivariate Cox Model | |
|---|---|---|---|---|---|---|---|---|
| | ≥Median | | | <Median | | | | |
| Antigen | n (% of total) | Deaths, n (%) | Median OS (mo) | n (% of total) | Deaths, n (%) | Median OS (mo) | HR (95% CI) | P-value |
| KRAS | 47-50.54 | 16 (34.04) | 26.5 | 46 (49.46) | 23 (50) | 26.3 | 0.83 (0.63-1.11) | 0.218 |
| KLK2 | 47-50.54 | 18 (38.3) | 28.9 | 46 (49.46) | 21 (45.65) | 26.5 | 0.75 (0.57-1) | 0.051 |

In the sipuleucel-T arm, IgG responses (≥2 fold increase at week 10) to PSA (responders n=36, non-responders n=57; HR=0.38, 95% CI 0.19, 0.80; p=0.01) and LGALS3 (responders n=26, non-responders n=67; HR=0.25, 95% CI 0.09, 0.72; p=0.01) were also significantly associated with improved OS (Table 11). Relative to patients in the control arm, patients in the sipuleucel-T arm who were anti-PSA IgG responders exhibited significantly improved OS (HR=0.27, 95% CI 0.12, 0.58; p<0.01; FIG. 4, Table 12), whereas OS in patients in the sipuleucel-T arm who were anti-PSA IgG non-responders did not differ significantly from that in patients in the control arm (HR=0.71, 95% CI 0.41, 1.23; p=0.23). Similarly, patients in the sipuleucel-T arm who were anti-LGALS3 IgG responders exhibited significantly improved OS compared to those in the control arm (HR=0.16, 95% CI 0.06, 0.49; p<0.01; FIG. 4), whereas OS in patients in the sipuleucel-T arm who were anti-LGALS3 IgG non-responders did not differ significantly from patients in the control arm (HR=0.66, 95% CI 0.38, 1.12; p=0.12). These results indicate that a relatively moderate increase in levels of IgGs to secondary antigens (≥2-fold) may identify patients who are more likely to have significant survival benefit after sipuleucel-T treatment than patients who do not show increase in these IgGs.

TABLE 11

Association of IgG responses (≥2-fold increase in serum IgG level post-treatment) with OS.

| | Change in IgG Level | | | | | | HR and P-value Multivariate Cox Model | |
|---|---|---|---|---|---|---|---|---|
| | IgG Responder | | | IgG Non-responder | | | | |
| Antigen | n (% of total) | Deaths, n (%) | Median OS (mo) | n (% of total) | Deaths, n (%) | Median OS (mo) | HR (95% CI) | P-value |
| PA2024 | 86-92.47 | 35 (40.7) | 27.12 | 7-7.53 | 4 (57.14) | 28.9 | 1.03 (0.36-2.98) | 0.952 |
| PAP | 69-74.19 | 25 (36.23) | 26.5 | 24-25.81 | 14 (58.33) | 27.12 | 0.77 (0.39-1.52) | 0.454 |
| Tetanus toxoid | 10-10.75 | 4 (40) | 28.9 | 83-89.25 | 35 (42.17) | 26.5 | 0.75 (0.26-2.12) | 0.582 |
| PSA | 36-38.71 | 10 (27.78) | NA | 57-61.29 | 29 (50.88) | 22.98 | 0.38 (0.19-0.8) | 0.01 |
| LGALS3 | 26-27.96 | 4 (15.38) | NA | 67-72.04 | 35 (52.24) | 25.38 | 0.25 (0.09-0.72) | 0.01 |
| ERAS | 39-41.94 | 14 (35.9) | 28.9 | 54-58.06 | 25 (46.3) | 26.3 | 0.55 (0.28-1.08) | 0.085 |
| LGALS8 | 23-24.73 | 7 (30.43) | NA | 70-75.27 | 32 (45.71) | 26.5 | 0.76 (0.33-1.73) | 0.51 |
| KRAS | 37-39.78 | 12 (32.43) | NA | 56-60.22 | 27 (48.21) | 26.5 | 0.77 (0.39-1.55) | 0.466 |
| KLK2 | 41-44.09 | 17 (41.46) | 28.9 | 52-55.91 | 22 (42.31) | 26.5 | 0.73 (0.38-1.4) | 0.348 |

TABLE 12

Comparison of OS in sipuleucel-T-treated IgG responders and IgG non-responders at week 10 with that in control patients in IMPACT.

| | Control | | | Change in IgG Level | | | | | | HR and P-value Multivariate Cox Model | | | |
|---|---|---|---|---|---|---|---|---|---|---|---|---|---|
| | | | | IgG Responder | | | IgG Non-responder | | | Control vs IgG Responder | | Control vs IgG-Non responder | |
| Antigen | n (% of total) | Deaths, n (%) | Median OS (mo) | n (% of total) | Deaths, n (%) | Median OS (mo) | n (% of total) | Deaths, n (%) | Median OS (mo) | HR (95% CI) | P-value | HR (95% CI) | P-value |
| PA2024 | 39 (29.55) | 23 (58.97) | 22.06 | 86 (65.15) | 35 (40.7) | 27.12 | 7 (5.3) | 4 (57.14) | 28.9 | 0.51 (0.3-0.88) | 0.015 | 0.51 (0.17-1.51) | 0.223 |
| PAP | 39 (29.55) | 23 (58.97) | 22.06 | 69 (52.27) | 25 (36.23) | 26.5 | 24 (18.18) | 14 (58.33) | 27.12 | 0.47 (0.26-0.83) | 0.01 | 0.63 (0.32-1.24) | 0.178 |

TABLE 12-continued

Comparison of OS in sipuleucel-T-treated IgG responders and IgG non-responders at week 10 with that in control patients in IMPACT.

| | Control | | | Change in IgG Level | | | | | | HR and P-value Multivariate Cox Model | | | |
| --- | --- | --- | --- | --- | --- | --- | --- | --- | --- | --- | --- | --- | --- |
| | | | | IgG Responder | | | IgG Non-responder | | | Control vs IgG Responder | | Control vs IgG-Non responder | |
| Antigen | n (% of total) | Deaths, n (%) | Median OS (mo) | n (% of total) | Deaths, n (%) | Median OS (mo) | n (% of total) | Deaths, n (%) | Median OS (mo) | HR (95% CI) | P-value | HR (95% CI) | P-value |
| PSA | 39 (29.55) | 23 (58.97) | 22.06 | 36 (27.27) | 10 (27.78) | NA | 57 (43.18) | 29 (50.88) | 22.98 | 0.27 (0.12-0.58) | 7.41E−04 | 0.71 (0.41-1.24) | 0.23 |
| LGALS3 | 39 (29.55) | 23 (58.97) | 22.06 | 26 (19.7) | 4 (15.38) | NA | 67 (50.76) | 35 (52.24) | 25.38 | 0.16 (0.06-0.49) | 1.09E−03 | 0.66 (0.38-1.12) | 0.123 |

Among patients from the sipuleucel-T arm in IMPACT, anti-PA2024 and anti-PAP IgG responders exhibited improved OS relative to control patients, whereas anti-PA2024 and anti-PAP IgG non-responders did not (Table 12). However, the increases in OS observed in the anti-PA2024 and anti-PAP IgG responders were not as significant as those in the anti-PSA or anti-LGALS3 IgG responders. A previous analysis of data from IMPACT, using different methodologies, showed that aggregated humoral (IgG and IgM combined) and cellular immune responses to PAP or PA2024 were associated with improved OS (Sheikh, et al., 2013).

Figure 5:
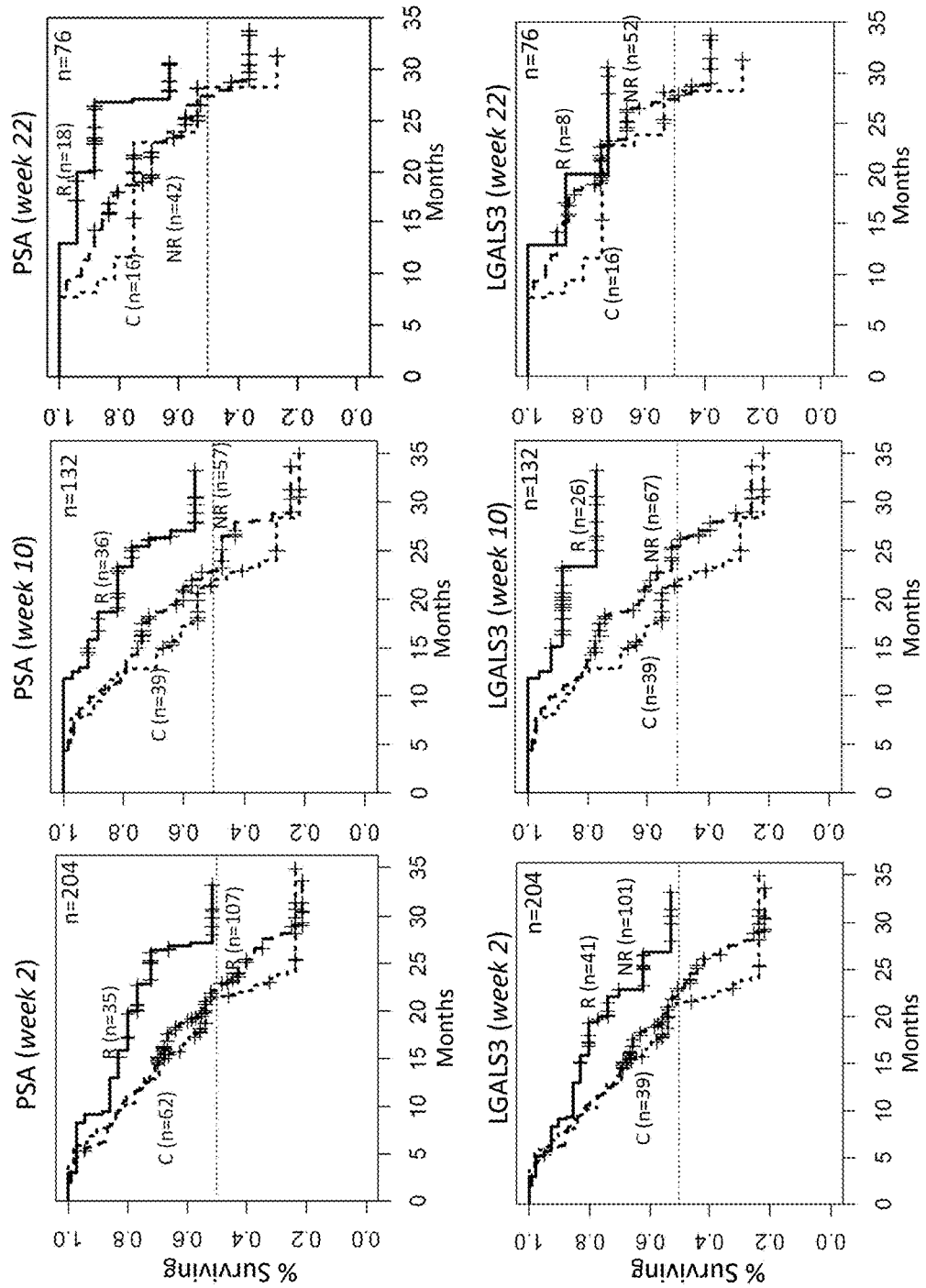
FIG. 5: Kaplan-Meier plots of OS for anti-PSA and anti-LGALS3 IgG responders (R) and non-responders (NR) in the sipuleucel-T arm and patients from the control arm (C) in IMPACT. Data for IgG responses at week 2 (Left), week 10 (Middle) and week 22 (Right) are shown. Top panel: anti-PSA IgG; bottom panel: anti-LGALS3 IgG. IgG responders are defined as patients with ≥2-fold increase in serum IgG level post-treatment relative to pre-treatment. The total number of patients in the analyses is given at the top right of each plot; the numbers of patients in the R (IgG-responders, solid line), NR (IgG non-responders, dashed line), and C (control, dotted line) groups are also shown. Refer to Table 8 for details.

In the sipuleucel-T-treated patients from IMPACT, IgG responses to PSA at week 2 were significantly associated with improved OS (responders n=35, non-responders n=107; HR=0.42, 95% CI 0.22, 0.79; p<0.01; FIG. 5; Table 13), and IgG responses to LGALS3 at week 2 showed a trend towards improved OS (responders n=41, non-responders n=101; HR=0.57, 95% CI 0.31, 1.02; p=0.06). Patients in the sipuleucel-T arm who were anti-PSA or anti-LGALS3 IgG responders at week 2 (but not the corresponding non-responders) exhibited significantly improved OS (p<0.01) relative to the patients in the control arm (FIG. 5; Table 14). Patients in the sipuleucel-T arm with IgG responses to the primary antigen (PAP or PA2024) at week 2 also exhibited improved OS (p<0.05, Table 14) compared to patients in the control arm, whereas OS of patients without the IgG responses were not significantly different from patients in the control arm. IgG responses at week 22 were not significantly associated with OS; however in the sipuleucel-T arm, patients with anti-PSA IgG responses showed a trend towards improved OS relative to non-responders (responders n=18, non-responders n=42; HR=0.35, 95% CI 0.12, 1.05; p=0.06, Table 13).

TABLE 13

Association IgG response (≥2-fold increase in serum IgG level post-treatment) with OS.

| | | Change in IgG Level | | | | | | Multivariate Cox Model | |
| --- | --- | --- | --- | --- | --- | --- | --- | --- | --- |
| | | IgG Responder | | | IgG Non-responder | | | | |
| Time-point | Antigen | n (% of total) | Deaths, n (%) | Median OS (mo) | n (% of total) | Deaths, n (%) | Median OS (mo) | HR (95% CI) | P-value |
| Week 2 | PA2024 | 119 (83.8) | 58 (48.74) | 25.38 | 23 (16.2) | 11 (47.83) | 21.27 | 0.86 (0.44-1.66) | 0.653 |
| | PAP | 92 (64.79) | 40 (43.48) | 26.3 | 50 (35.21) | 29 (58) | 22.03 | 0.66 (0.4-1.07) | 0.091 |
| | PSA | 35 (24.65) | 12 (34.29) | NA | 107 (75.35) | 57 (53.27) | 22.03 | 0.42 (0.22-0.79) | 0.007 |
| | LGALS3 | 41 (28.87) | 14 (34.15) | NA | 101 (71.13) | 55 (54.46) | 22.98 | 0.57 (0.31-1.02) | 0.06 |
| Week 22 | PA2024 | 52 (86.67) | 19 (36.54) | 27.45 | 8 (13.33) | 4 (50) | 28.9 | 1.03 (0.34-3.17) | 0.958 |
| | PAP | 35 (58.33) | 11 (31.43) | 26.76 | 25 (41.67) | 12 (48) | 28.04 | 0.97 (0.41-2.29) | 0.937 |
| | PSA | 18 (30) | 4 (22.22) | NA | 42 (70) | 19 (45.24) | 27.45 | 0.35 (0.12-1.05) | 0.06 |
| | LGALS3 | 8 (13.33) | 2 (25) | NA | 52 (86.67) | 21 (40.38) | 27.45 | 0.39 (0.08-1.82) | 0.23 |

TABLE 14

Comparison of OS in sipuleucel-T-treated IgG responders and IgG non-responders at weeks 2 and 22 with that in control patients in IMPACT.

| | | Control | | | Sipuleucel-T | | | | | | HR and P-value Multivariate Cox Model | | | |
| | | | | | IgG Responder | | | IgG Non-responder | | | Control vs IgG Responder | | Control vs IgG Non-responder | |
| Time-point | Antigen | n (% of total) | Deaths, n (%) | Median OS (mo) | n (% of total) | Deaths, n (%) | Median OS (mo) | n (% of total) | Deaths, n (%) | Median OS (mo) | HR (95% CI) | P-value | HR (95% CI) | P-value |
|---|---|---|---|---|---|---|---|---|---|---|---|---|---|---|
| Week 2 | PA2024 | 62 (30.39) | 39 (62.9) | 21.4 | 119 (58.33) | 58 (48.74) | 25.38 | 23 (11.27) | 11 (47.83) | 21.27 | 0.64 (0.42-0.96) | 0.03 | 0.74 (0.38-1.47) | 0.394 |
| | PAP | 62 (30.39) | 39 (62.9) | 21.4 | 92 (45.1) | 40 (43.48) | 26.3 | 50 (24.51) | 29 (58) | 22.03 | 0.56 (0.36-0.87) | 0.011 | 0.84 (0.52-1.36) | 0.473 |
| | PSA | 62 (30.39) | 39 (62.9) | 21.4 | 35 (17.16) | 12 (34.29) | NA | 107 (52.45) | 57 (53.27) | 22.03 | 0.33 (0.17-0.64) | 0.000955 | 0.8 (0.53-1.21) | 0.298 |
| | LGALS3 | 62 (30.39) | 39 (62.9) | 21.4 | 41 (20.1) | 14 (34.15) | NA | 101 (49.51) | 55 (54.46) | 22.98 | 0.42 (0.23-0.77) | 0.005 | 0.76 (0.5-1.14) | 0.187 |
| Week 22 | PA2024 | 16 (21.05) | 7 (43.75) | 28.34 | 52 (68.42) | 19 (36.54) | 27.45 | 8 (10.53) | 4 (50) | 28.9 | 0.69 (0.28-1.7) | 0.417 | 0.63 (0.17-2.38) | 0.494 |
| | PAP | 16 (21.05) | 7 (43.75) | 28.34 | 3 (46.05) | 11 (31.43) | 26.76 | 25 (32.89) | 12 (48) | 28.04 | 0.69 (0.26-1.83) | 0.459 | 0.67 (0.24-1.82) | 0.431 |
| | PSA | 16 (21.05) | 7 (43.75) | 28.34 | 18 (23.68) | 4 (22.22) | NA | 42 (55.26) | 19 (45.24) | 27.45 | 0.32 (0.09-1.15) | 0.081 | 0.88 (0.35-2.17) | 0.775 |
| | LGALS3 | 16 (21.05) | 7 (43.75) | 28.34 | 8 (10.53) | 2 (25) | NA | 52 (68.42) | 21 (40.38) | 27.45 | 0.29 (0.05-1.59) | 0.154 | 0.73 (0.3-1.78) | 0.491 |

NA, not applicable.

H. Conclusions

Evaluation of IgGs against candidate antigens PSA, KRAS, ERAS, LGALS3, LGALS8, and KLK2 showed significant post-treatment elevation of IgG levels relative to the level measured at the pretreatment timepoint in sipuleucel-T treated subjects. No elevation was observed in the evaluable placebo treated subjects. This result provides evidence for antigen spread against secondary antigens post-sipuleucel-T treatment. Several antigens against which IgG responses are observed show increased expressions or somatic mutations in prostate tumors (KRAS, KLK2, LGALS8 and LGALS3), have prostate specific expression (KLK2), or are known to be a prostate tumor antigen (LGALS8). Therefore, the results indicate in vivo activity against the prostate tumor post-sipuleucel-T therapy. Moreover, KRAS, ERAS, KLK2, LGALS3, LGALS8, and PSA, for example, represent promising targets for future immunotherapies against prostate cancer.

Subjects with IgG responses against individual antigens overlap significantly, indicating several subjects had IgG responses, simultaneously, against multiple antigens. IgG responses against several antigens (e.g., PSA and LGALS3) were associated with OS in the sipuleucel-T treated subjects. IgG responses against the above antigens may therefore be used for the prediction of clinical responders to sipuleucel-T. Since IgG responses against multiple antigens can increase the association with OS, IgGs against multiple antigens may provide an effective, multivariate, post-treatment, pharmacodynamic biomarker for assessing clinical outcome in sipuleucel-T treated subjects.

REFERENCES

Aragon-Ching J B, Madan R A, Dahut W L. Angiogenesis inhibition in prostate cancer: current uses and future promises. Journal of oncology. 2010; 2010: 361836

Arencibia J M, Martin S, Perez-Rodriguez F J, Bonnin A. Gene expression profiling reveals overexpression of TSPAN13 in prostate cancer. International journal of oncology. 2009; 34(2): 457-63

Balan V, Nangia-Makker P, Kho D H, et al: Tyrosine-phosphorylated galectin-3 protein is resistant to prostate-specific antigen (PSA) cleavage. J Biol Chem 287:5192-8, 2012

Benjamini Y H, Y. Controlling the False Discovery Rate: A Practical and Powerful Approach to Multiple Testing. Journal of the Royal Society, Series B (Methodological). 1995; 57(1): 289-300

Butterfield L H, Ribas A, Dissette V B, Amarnani S N, Vu H T, Oseguera D, et al. Determinant spreading associated with clinical response in dendritic cell-based immunotherapy for malignant melanoma. Clin Cancer Res. 2003; 9(3): 998-1008.

Califice S, Castronovo V, Bracke M, van den Brule F. Dual activities of galectin-3 in human prostate cancer: tumor suppression of nuclear galectin-3 vs tumor promotion of cytoplasmic galectin-3. Oncogene. 2004; 23(45): 7527-36

Cardozo T, Pagano M: The SCF ubiquitin ligase: insights into a molecular machine. Nat Rev Mol Cell Biol 5:739-51, 2004

Carducci M A, Padley R J, Breul J, Vogelzang N J, Zonnenberg B A, Daliani D D, et al. Effect of endothelin-A receptor blockade with atrasentan on tumor progression in men with hormone-refractory prostate cancer: a randomized, phase II, placebo-controlled trial. Journal of clinical oncology: official journal of the American Society of Clinical Oncology. 2003; 21(4): 679-89

Catterall W A: Structure and function of voltage-sensitive ion channels. Science 242:50-61, 1988

Corbiere V, Chapiro J, Stroobant V, Ma W, Lurquin C, Lethe B, et al. Antigen spreading contributes to MAGE vaccination-induced regression of melanoma metastases. Cancer research. 2011; 71(4): 1253-62

Dai J, Kitagawa Y, Zhang J, Yao Z, Mizokami A, Cheng S, et al. Vascular endothelial growth factor contributes to the prostate cancer-induced osteoblast differentiation mediated by bone morphogenetic protein. Cancer research. 2004; 64(3): 994-9

Darson M F, Pacelli A, Roche P, Rittenhouse H G, Wolfert R L, Saeid M S, et al. Human glandular kallikrein 2 expression in prostate adenocarcinoma and lymph node metastases. Urology. 1999; 53(5): 939-44

Dawson L A, Maitland N J, Berry P, Turner A J, Usmani B A. Expression and localization of endothelin-converting enzyme-1 in human prostate cancer. Exp Biol Med (Maywood). 2006; 231(6): 1106-10

Disis M L, Goodell V, Schiffman K, Knutson K L. Humoral epitope-spreading following immunization with a HER-2/neu peptide based vaccine in cancer patients. J Clin Immunol. 2004; 24(5): 571-8

Elad-Sfadia G, Haklai R, Balan E, et al: Galectin-3 augments K-Ras activation and triggers a Ras signal that attenuates ERK but not phosphoinositide 3-kinase activity. J Biol Chem 279:34922-30, 2004

Fukasawa K, Fujii H, Saitoh Y, Koizumi K, Aozuka Y, Sekine K, et al. Aminopeptidase N (APN/CD13) is selectively expressed in vascular endothelial cells and plays multiple roles in angiogenesis. Cancer letters. 2006; 243(1): 135-43

Ghosh D, Chinnaiyan A M. Genomic outlier profile analysis: mixture models, null hypotheses, and nonparametric estimation. Biostatistics. 2009; 10(1): 60-9

Guzman-Rojas L, Rangel R, Salameh A, Edwards J K, Dondossola E, Kim Y G, et al. Cooperative effects of aminopeptidase N (CD13) expressed by nonmalignant and cancer cells within the tumor microenvironment. Proc Natl Acad Sci USA. 2012; 109(5): 1637-42

Hardwick N, Chain B. Epitope spreading contributes to effective immunotherapy in metastatic melanoma patients. Immunotherapy. 2011; 3(6): 731-3

Helo P, Cronin A M, Danila D C, Wenske S, Gonzalez-Espinoza R, Anand A, et al. Circulating prostate tumor cells detected by reverse transcription-PCR in men with localized or castration-refractory prostate cancer: concordance with CellSearch assay and association with bone metastases and with survival. Clinical chemistry. 2009; 55(4): 765-73

Herrmann E, Bogemann M, Bierer S, Eltze E, Hertle L, Wulfing C. The endothelin axis in urologic tumors: mechanisms of tumor biology and therapeutic implications. Expert review of anticancer therapy. 2006; 6(1): 73-81 www.cbioportal.org/public-portal/?cancer_type_id=pca
cran.r-project.org/web/packages/survival/index.html
cran.r-project.org/web/packages/survival/survival.pdf
cran.r-project.org/doc/contrib/Fox-Companion/appendix-cox-regression.pdf
www.ingenuity.com/products/pathways_analysis.html.
www.ingenuity.com/science/knowledge_base.html stat.ethz.ch/R-manual/R-patched/library/stats/html/wilcox.test.html James N D, Caty A, Payne H, Borre M, Zonnenberg B A, Beuzeboc P, et al. Final safety and efficacy analysis of the specific endothelin A receptor antagonist zibotentan (ZD4054) in patients with metastatic castration-resistant prostate cancer and bone metastases who were pain-free or mildly symptomatic for pain: a double-blind, placebo-controlled, randomized Phase II trial. BJU international. 2010; 106(7): 966-73

Kanehisa M, Goto S, Sato Y, Furumichi M, Tanabe M. KEGG for integration and interpretation of large-scale molecular data sets. Nucleic acids research. 2012; 40(Database issue): D109-14

Kantoff P W, Higano C S, Shore N D, Berger E R, Small E J, Penson D F, et al. Sipuleucel-T immunotherapy for castration-resistant prostate cancer. N Engl J Med. 2010; 363(5): 411-22

Kopetz E S, Nelson J B, Carducci M A. Endothelin-1 as a target for therapeutic intervention in prostate cancer. Investigational new drugs. 2002; 20(2): 173-82

Kubota E, Kataoka H, Aoyama M, et al: Role of ES cell-expressed Ras (ERas) in tumorigenicity of gastric cancer. Am J Pathol 177:955-63, 2010

Kwek S S, Dao V, Roy R, Hou Y, Alajajian D, Simko J P, et al. Diversity of antigen-specific responses induced in vivo with CTLA-4 blockade in prostate cancer patients. J Immunol. 2012; 189(7): 3759-66

Laderach D J, Gentilini L D, Giribaldi L, Delgado V C, Nugnes L, Croci D O, et al. A unique galectin signature in human prostate cancer progression suggests galectin-1 as a key target for treatment of advanced disease. Cancer research. 2013; 73(1): 86-96

Lambert L A, Whyteside A R, Turner A J, Usmani B A. Isoforms of endothelin-converting enzyme-1 (ECE-1) have opposing effects on prostate cancer cell invasion. Br J Cancer. 2008; 99(7): 1114-20

Larkin S E, Holmes S, Cree I A, Walker T, Basketter V, Bickers B, et al. Identification of markers of prostate cancer progression using candidate gene expression. Br J Cancer. 2012; 106(1): 157-Larsen S L, Pedersen L O, Buus S, et al: T cell responses affected by aminopeptidase N (CD13)-mediated trimming of major histocompatibility complex class II-bound peptides. J Exp Med 184:183-9, 1996

Liu P, Ramachandran S, Ali Seyed M, Scharer C D, Laycock N, Dalton W B, et al. Sex-determining region Y box 4 is a transforming oncogene in human prostate cancer cells. Cancer research. 2006; 66(8): 4011-9

Maecker H T, Todd S C, Levy S: The tetraspanin superfamily: molecular facilitators. FASEB J 11:428-42, 1997

Magklara A, Scorilas A, Stephan C, Kristiansen G O, Hauptmann S, Jung K, et al. Decreased concentrations of prostate-specific antigen and human glandular kallikrein 2 in malignant versus nonmalignant prostatic tissue. Urology. 2000; 56(3): 527-32

Markowska A I, Liu F T, Panjwani N. Galectin-3 is an important mediator of VEGF- and bFGF-mediated angiogenic response. The Journal of experimental medicine. 2010; 207(9): 1981-93

McQuillan G M, Kruszon-Moran D, Deforest A, et al: Serologic immunity to diphtheria and tetanus in the United States. Ann Intern Med 136:660-6, 2002

Merseburger A S, Kramer M W, Hennenlotter J, Simon P, Knapp J, Hartmann J T, et al. Involvement of decreased Galectin-3 expression in the pathogenesis and progression of prostate cancer. The Prostate. 2008; 68(1): 72-7

Mittendorf E A, Gurney J M, Stoner C E, Shriver C D, Ponniah S, Peoples G E. Vaccination with a HER2/neu peptide induces intra- and inter-antigenic epitope spreading in patients with early stage breast cancer. Surgery. 2006; 139(3): 407-18

Morgan T M, Koreckij T D, Corey E. Targeted therapy for advanced prostate cancer inhibition of the PI3K/Akt/mTOR pathway. Current cancer drug targets. 2009; 9(2): 237-49

Nam R K, Zhang W W, Klotz L H, Trachtenberg J, Jewett M A, Sweet J, et al. Variants of the hK2 protein gene (KLK2) are associated with serum hK2 levels and predict the presence of prostate cancer at biopsy. Clin Cancer Res. 2006; 12(21): 6452-8

Nam R K, Zhang W W, Trachtenberg J, Diamandis E, Toi A, Emami M, et al. Single nucleotide polymorphism of the human kallikrein-2 gene highly correlates with serum human kallikrein-2 levels and in combination enhances prostate cancer detection. Journal of clinical oncology: official journal of the American Society of Clinical Oncology. 2003; 21(12): 2312-9

Nelson J B, Hedican S P, George D J, Reddi A H, Piantadosi S, Eisenberger M A, et al. Identification of endothelin-1 in the pathophysiology of metastatic adenocarcinoma of the prostate. Nature medicine. 1995; 1(9): 944-9

Nelson J B, Udan M S, Guruli G, Pflug B R. Endothelin-1 inhibits apoptosis in prostate cancer. Neoplasia. 2005; 7(7): 631-7

Nesslinger N J, Sahota R A, Stone B, Johnson K, Chima N, King C, et al. Standard treatments induce antigen-specific immune responses in prostate cancer. Clin Cancer Res. 2007; 13(5): 1493-502

Nesslinger N J, Ng A, Tsang K Y, Ferrara T, Schlom J, Gulley J L, et al. A viral vaccine encoding prostate-specific antigen induces antigen spreading to a common set of self-proteins in prostate cancer patients. Clin Cancer Res. 2010; 16(15): 4046-56

Newlaczyl A U, Yu L G: Galectin-3—a jack-of-all-trades in cancer. Cancer Lett 313:123-8, 2011

Nguyen M C, Tu G H, Koprivnikar K E, Gonzalez-Edick M, Jooss K U, Harding T C. Antibody responses to galectin-8, TARP and TRAP1 in prostate cancer patients treated with a GM-CSF-secreting cellular immunotherapy. Cancer immunology, immunotherapy: CII. 2010; 59(9): 1313-23

Pasqualini R, Koivunen E, Kain R, Landenranta J, Sakamoto M, Stryhn A, et al. Aminopeptidase N is a receptor for tumor-homing peptides and a target for inhibiting angiogenesis. Cancer research. 2000; 60(3): 722-7

Perillo N L, Marcus M E, Baum L G: Galectins: versatile modulators of cell adhesion, cell proliferation, and cell death. J Mol Med (Berl) 76:402-12, 1998

Pickering J W, Martins T B, Schroder M C, et al: Comparison of a multiplex flow cytometric assay with enzyme-linked immunosorbent assay for auantitation of antibodies to tetanus, diphtheria, and Haemophilus influenzae Type b. Clin Diagn Lab Immunol 9:872-6, 2002

Powers P A, Liu S, Hogan K, et al: Molecular characterization of the gene encoding the gamma subunit of the human skeletal muscle 1,4-dihydropyridine-sensitive Ca2+ channel (CACNLG), cDNA sequence, gene structure, and chromosomal location. J Biol Chem 268:9275-9, 1993

Raaijmakers R, de Vries S H, Blijenberg B G, Wildhagen M F, Postma R, Bangma C H, et al. hK2 and free PSA, a prognostic combination in predicting minimal prostate cancer in screen-detected men within the PSA range 4-10 ng/ml. European urology. 2007; 52(5): 1358-64

Ribas A, Timmerman J M, Butterfield L H, Economou J S. Determinant spreading and tumor responses after peptide-based cancer immunotherapy. Trends Immunol. 2003; 24(2): 58-61

Rittenhouse H G, Finlay J A, Mikolajczyk S D, Partin A W. Human Kallikrein 2 (hK2) and prostate-specific antigen (PSA): two closely related, but distinct, kallikreins in the prostate. Critical reviews in clinical laboratory sciences. 1998; 35(4): 275-368

Sano H, Hsu D K, Yu L, et al: Human galectin-3 is a novel chemoattractant for monocytes and macrophages. J Immunol 165:2156-64, 2000

Santegoets S J. The Induction of Autoantibodies to PSMA, PNPO and NRP2 Correlates with Clinical Outcome in Patients Treated with Prostate GVAX/Anti-CTLA-4 Immunotherapy. Keystone Symposium Cancer Control by Tumor Suppressors and Immune Effectors (J8); Workshop 3: Perspectives on Breaking Tolerance in Cancer Immunotherapy; 2011

Scanlan M J, Simpson A J, Old L J. The cancer/testis genes: review, standardization, and commentary. Cancer immunity. 2004; 4: 1

Shalom-Feuerstein R, Cooks T, Raz A, et al: Galectin-3 regulates a molecular switch from N-Ras to K-Ras usage in human breast carcinoma cells. Cancer Res 65:7292-300, 2005

Sheikh N A, Petrylak D, Kantoff P W, et al: Sipuleucel-T immune parameters correlate with survival: an analysis of the randomized phase 3 clinical trials in men with castration-resistant prostate cancer. Cancer Immunol Immunother 62:137-47, 2013

Sorensen K D, Abildgaard M O, Haldrup C, et al: Prognostic significance of aberrantly silenced ANPEP expression in prostate cancer. Br J Cancer 108:420-8, 2013

Smyth G K. Linear models and empirical bayes methods for assessing differential expression in microarray experiments. Stat Appl Genet Mol Biol. 2004; 3: Article 3

Smyth G K: Limma: linear models for microarray data, in R. Gentleman V C, S. Dudoit, R. Irizarry, W. Huber (ed): Bioinformatics and Computational Biology Solutions Using {R} and Bioconductor. New York, Springer, 2005, pp 397-420

Su Z Z, Lin J, Shen R, Fisher P E, Goldstein N I, Fisher P B. Surface-epitope masking and expression cloning identifies the human prostate carcinoma tumor antigen gene PCTA-1 a member of the galectin gene family. Proc Natl Acad Sci USA. 1996; 93(14): 7252-7

Takahashi K, Mitsui K, Yamanaka S: Role of ERas in promoting tumour-like properties in mouse embryonic stem cells. Nature 423:541-5, 2003

T. C. Harding M N, K. Koprivnikar, G. Haun-Tu, J. Ma, K. Hege, N. Sacks, E. Small, K. Jooss Identification of antibody responses induced in patients with biochemically recurrent and castration-resistant prostate cancer (CRPC) receiving GVAX immunotherapy for prostate cancer. SASCO Meeting, #18: 2008 Meeting on Molecular Markers; 2008

Taylor B S, Schultz N, Hieronymus H, Gopalan A, Xiao Y, Carver B S, et al. Integrative genomic profiling of human prostate cancer. Cancer cell. 2010; 18(1): 11-22

Thakkar S G, Choueiri T K, Garcia J A. Endothelin receptor antagonists: rationale, clinical development, and role in prostate cancer therapeutics. Current oncology reports. 2006; 8(2): 108-13

Tomlins S A, Mehra R, Rhodes D R, Cao X, Wang L, Dhanasekaran S M, et al. Integrative molecular concept modeling of prostate cancer progression. Nat Genet. 2007; 39(1): 41-51 van den Brule F A, Waltregny D, Liu F T, Castronovo V. Alteration of the cytoplasmic/nuclear expression pattern of galectin-3 correlates with prostate carcinoma progression. International journal of cancer Journal international du cancer. 2000; 89(4): 361-7

Vanderlugt C L, Miller S D. Epitope spreading in immune-mediated diseases: implications for immunotherapy. Nat Rev Immunol. 2002; 2(2): 85-95.

Wallace T A, Prueitt R L, Yi M, Howe T M, Gillespie J W, Yfantis H G, et al. Tumor immunobiological differences in prostate cancer between African-American and European-American men. Cancer research. 2008; 68(3): 927-36

Wang Y, Nangia-Makker P, Tait L, Balan V, Hogan V, Pienta K J, et al. Regulation of prostate cancer progression by galectin-3. The American journal of pathology. 2009; 174(4): 1515-23

Whyteside A R, Hinsley E E, Lambert L A, McDermott P J, Turner A J. ECE-1 influences prostate cancer cell invasion via ET-1-mediated FAK phosphorylation and ET-1-independent mechanisms. Canadian journal of physiology and pharmacology. 2010; 88(8): 850-4

Williams S A, Xu Y, De Marzo A M, Isaacs J T, Denmeade S R. Prostate-specific antigen (PSA) is activated by KLK2 in prostate cancer ex vivo models and in prostate-targeted PSA/KLK2 double transgenic mice. The Prostate. 2010; 70(7): 788-96

Yang E, Shim J S, Woo H J, Kim K W, Kwon H J. Aminopeptidase N/CD13 induces angiogenesis through interaction with a pro-angiogenic protein, galectin-3. Biochemical and biophysical research communications. 2007; 363(2): 336-41

Zhang Y W, Brognard J, Coughlin C, You Z, Dolled-Filhart M, Aslanian A, et al. The F box protein Fbx6 regulates Chk1 stability and cellular sensitivity to replication stress. Molecular cell. 2009; 35(4): 442-53

What is claimed is:

1. A method of treating a prostate cancer patient who is responsive to cancer antigen specific active immunotherapy (CASAI) using prostatic acid phosphatase as a target cancer antigen where the method comprises the steps of:
   i. selecting a prostate cancer patient with white blood cells who has been treated with a cancer antigen specific active immunotherapy (CASAI) using prostatic acid phosphatase fused to granulocyte macrophage colony-stimulating factor as a target cancer antigen to activate the patient's white blood cells under ex vivo conditions and who has an increase in reactive antibody levels in two or more non-target predetermined biomarker antigens of prostate cancer where the increase in reactive antibody levels is determined using an immunoassay that detects reactive antibody levels for at least four of the following predetermined biomarker antigens of prostate cancer: PSA, KLK2, KRAS, ERAS, LGALS8, and LGALS3 compared to a baseline antibody level from before CASAI treatment; and,
   ii. treating the prostate cancer patient with CASAI using a target cancer antigen comprising prostatic acid phosphatase fused to granulocyte macrophage colony-stimulating factor to activate the patient's white blood cells under ex vivo conditions.

2. The method of claim 1, wherein the selected patient has elevated post-treatment antibody levels reactive to the target cancer antigen where the elevation is determined by obtaining a baseline and a post-treatment antibody level reactive to the target cancer antigen.

3. The method of claim 1, wherein the baseline reactive antibody levels or the post-treatment reactive antibody levels from the patient are reactive IgG levels.

4. The method of claim 1, wherein the reactive antibody levels are detected using a solid support surface and a fluorescent or enzymatic label.

5. The method of claim 1, wherein the selected patient has an increase in reactive antibody levels of PSA and one or more other non-target predetermined biomarker antigens selected from the group consisting of KLK2, KRAS, ERAS, LGALS8, and LGALS3.

6. The method of claim 1, wherein the selected patient has an increase in reactive antibody levels of ERAS and any one of four markers selected from the group consisting of KLK2, KRAS, LGALS8, LGALS3, and PSA.

7. The method of claim 1, wherein the selected patient has an increase in reactive antibody levels of KRAS and any one of four markers selected from the group consisting of KLK2, ERAS, LGALS8, LGALS3, and PSA.

8. The method of claim 1, wherein the selected patient has an increase in reactive antibody levels of ERAS.

9. The method of claim 1, wherein the selected patient has an increase in reactive antibody levels of KLK2.

10. The method of claim 1, wherein the selected patient has an increase in reactive antibody levels of PSA.

11. The method of claim 1, wherein the CASAI is sipuleucel-T treatment.

* * * * *